United States Patent
Larsen et al.

(10) Patent No.: US 10,851,072 B2
(45) Date of Patent: Dec. 1, 2020

(54) INHIBITORS OF RHO/MRTF/SRF-MEDIATED GENE TRANSCRIPTION AND METHODS FOR USE OF THE SAME

(71) Applicants: THE REGENTS OF THE UNIVERSITY OF MICHIGAN, Ann Arbor, MI (US); BOARD OF TRUSTEES OF MICHIGAN STATE UNIVERSITY, East Lansing, MI (US)

(72) Inventors: Scott D. Larsen, South Lyon, MI (US); Richard Neubig, East Lansing, MI (US); Kim Hutchings, Dexter, MI (US); Dylan Kahl, Ann Arbor, MI (US); Erika Mathes Lisabeth, Howell, MI (US)

(73) Assignees: THE REGENTS OF THE UNIVERSITY OF MICHIGAN, Ann Arbor, MI (US); BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 16/376,349

(22) Filed: Apr. 5, 2019

(65) Prior Publication Data
US 2019/0308947 A1 Oct. 10, 2019

Related U.S. Application Data

(60) Provisional application No. 62/653,869, filed on Apr. 6, 2018.

(51) Int. Cl.
C07D 271/113 (2006.01)
C07D 271/06 (2006.01)
C07D 413/12 (2006.01)
A61P 35/00 (2006.01)

(52) U.S. Cl.
CPC .......... *C07D 271/113* (2013.01); *A61P 35/00* (2018.01); *C07D 271/06* (2013.01); *C07D 413/12* (2013.01)

(58) Field of Classification Search
CPC .................... C07D 271/06; C07D 271/113
See application file for complete search history.

(56) References Cited

U.S. PATENT DOCUMENTS

| | | | |
|---|---|---|---|
| 5,354,308 A | 10/1994 | Simon et al. | |
| 5,674,192 A | 10/1997 | Sahatjian et al. | |
| 5,693,014 A | 12/1997 | Abele et al. | |
| 5,733,303 A | 3/1998 | Israel et al. | |
| 5,755,722 A | 5/1998 | Barry et al. | |
| 5,792,105 A | 8/1998 | Lin et al. | |
| 5,800,391 A | 9/1998 | Kontos | |
| 5,800,508 A | 9/1998 | Goicoechea et al. | |
| 5,800,519 A | 9/1998 | Sandock | |
| 5,843,089 A | 12/1998 | Sahatjian et al. | |
| 5,851,228 A | 12/1998 | Pinheiro | |
| 5,857,998 A | 1/1999 | Barry | |
| 5,866,561 A | 2/1999 | Ungs | |
| 5,868,719 A | 2/1999 | Tsukernik | |
| 5,876,445 A | 3/1999 | Andersen et al. | |
| 5,908,413 A | 6/1999 | Lange et al. | |
| 5,913,894 A | 6/1999 | Schmitt | |
| 5,933,145 A | 8/1999 | Meek | |
| 5,935,114 A | 8/1999 | Jang et al. | |
| 2015/0250769 A1* | 9/2015 | Larsen ............... A61K 31/4245 514/364 |

FOREIGN PATENT DOCUMENTS

WO   WO-2015/138326   9/2015

OTHER PUBLICATIONS

Patani et al. "Bioisosterisnn: A Rational Approach in Drug Design" Chemical Reviews, vol. 96, pp. 3147-3176. (Year: 1996).*
Ramaprasad et al., Synthesis and biological property of some novel 1,3,4-oxadiazoles, Eur. J. Med. Chem., 45(10):4587-93 (Oct. 2010).
International Application No. PCT/US2019/025925, International Search Report and Written Opinion, dated Sep. 30, 2019.
Akhmetshina et al., Rho-associated kinases are crucial for myofibroblast differentiation and production of extracellular matrix in scleroderma fibroblasts, Arthritis Rheum., 58(8):2553-64 (Aug. 2008).
Bartolomé et al., Stromal cell-derived factor-1alpha promotes melanoma cell invasion across basement membranes involving stimulation of membrane-type 1 matrix metalloproteinase and Rho GTPase activities, Cancer Res., 64(7):2534-43 (Apr. 2004).
Bell et al., Optimization of novel nipecotic bis(amide) inhibitors of the Rho/MKL1/SRF transcriptional pathway as potential antimetastasis agents, Bioorg. Med. Chem. Lett., 23(13):3826-32 (Jul. 2013).

(Continued)

*Primary Examiner* — Joseph R Kosack
(74) *Attorney, Agent, or Firm* — Marshall, Gerstein & Borun LLP

(57) ABSTRACT

Disclosed herein are inhibitors of Rho/MRTF/SRF-mediated gene transcription, and methods for their use in treating or preventing diseases such as cancer and fibrosis. In particular, disclosed herein are compounds of Formula (I) and pharmaceutically acceptable salts thereof:

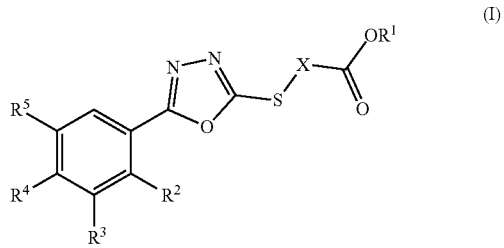

wherein the substituents are as described.

17 Claims, 1 Drawing Sheet

(56) References Cited

OTHER PUBLICATIONS

Benbow et al., The AP-1 site and MMP gene regulation: what is all the fuss about?, Matrix Biol., 15(8-9):519-26 (Mar. 1997).
Bernard et al., [The OTT-MAL fusion oncogene: another Notch in megakaryoblastic leukemia] [Article in French], 25(8-0):676-8 (Aug.-Sep. 2009).
Beyer et al., Animal models of systemic sclerosis: prospects and limitations, Arthritis Rheum., 62(10):2831-44 (Oct. 2010).
Beyer et al., Innovative antifibrotic therapies in systemic sclerosis, Curr. Opin. Rheumatol., 24(3):274-80 (May 2012).
Boukhalfa et al., Relationship between alpha-smooth muscle actin expression and fibrotic changes in human kidney, Exp. Nephrol., 4(4):241-7 (Jul.-Aug. 1996).
Buhl et al., G alpha 12 and G alpha 13 stimulate Rho-dependent stress fiber formation and focal adhesion assembly, J. Biol. Chem., 270(42):24631-4 (Oct. 1995).
Buller et al., Regulation of serum response factor by miRNA-200 and miRNA-9 modulates oligodendrocyte progenitor cell differentiation, Glia, 60(12):1906-14 (Dec. 2012).
Burridge et al., Rho and Rac take center stage, Cell, 116(2):167-79 (Jan. 2004).
Cen et al., Megakaryoblastic leukemia 1, a potent transcriptional coactivator for serum response factor (SRF), is required for serum induction of SRF target genes, Mol. Cell Biol., 23(18):6597-608 (Sep. 2003).
Chaqour et al., Mechanical regulation of the Cyr61/CCN1 and CTGF/CCN2 proteins, FEBS J., 273(16):3639-49 (Aug. 2006).
Charles et al., Systemic sclerosis: hypothesis-driven treatment strategies, Lancet, 367(9523):1683-91 (May 2006).
Chong et al., STARS is essential to maintain cardiac development and function in vivo via a SRF pathway, PLoS One, 7(7):e40966 (2012).
Chrissobolis et al., Recent evidence for an involvement of rho-kinase in cerebral vascular disease, Stroke, 37(8):2174-80 (Aug. 2006).
Clark et al., Genomic analysis of metastasis reveals an essential role for RhoC, Nature, 406(6795):532-5 (Aug. 2000).
Cooper et al., Stromal factors involved in prostate carcinoma metastasis to bone, Cancer, 97(3 Suppl):739-47 (Feb. 2003).
Crider et al., Myocardin-related transcription factors A and B are key regulators of TGF-β1-induced fibroblast to myofibroblast differentiation, J. Invest. Dermatol., 131912):2378-85 (Dec. 2011).
Dietrich et al., Production and characterization of monoclonal antibodies against the hemolysin BL enterotoxin complex produced by Bacillus cereus, Appl. Environ. Microbiol., 65(10):4470-4 (Oct. 1999).
Evelyn et al., CCG-1423: a small-molecule inhibitor of RhoA transcriptional signaling, Mol. Cancer Ther., 6(8):2249-60 (Aug. 2007).
Eveyln et al., Design, synthesis and prostate cancer cell-based studies of analogs of the Rho/MKL1 transcriptional pathway inhibitor, CCG-1423, Bioorg. Med. Chem. Lett., 20(2):665-72 (Jan. 2010).
Fortin Ensign et al., Implications of Rho GTPase Signaling in Glioma Cell Invasion and Tumor Progression, Front. Oncol., 3:241 (Oct. 2013).
Fukuhara et al., A novel PDZ domain containing guanine nucleotide exchange factor links heterotrimeric G proteins to Rho, J. Biol. Chem., 274(9):5868-79 (Feb. 1999).
Fukuhara et al., Leukemia-associated Rho guanine nucleotide exchange factor (LARG) links heterotrimeric G proteins of the G(12) family to Rho, FEBS Lett., 485(2-3):183-8 (Nov. 2000).
Gilbane et al., Scleroderma pathogenesis: a pivotal role for fibroblasts as effector cells, Arthritis Res. Ther., 1593):215 (2013).
Gilles et al., MAL/SRF complex is involved in platelet formation and megakaryocyte migration by regulating MYL9 (MLC2) and MMP9, Blood, 114(19):4221-32 (Nov. 2009).
Gross et al., The pivotal role of RhoA GTPase in the molecular signaling of axon growth inhibition after CNS injury and targeted therapeutic strategies, Cell Transplant., 16(3):245-62 (2007).
Haak et al., Targeting the myofibroblast genetic switch: inhibitors of myocardin-related transcription factor/serum response factor-regulated gene transcription prevent fibrosis in a murine model of skin injury, J. Pharmacol. Exp. Ther., 349(3):480-6 (Jun. 2014).
Hakem et al., RhoC is dispensable for embryogenesis and tumor initiation but essential for metastasis, Genes Dev., 19(17):1974-9 (Sep. 2005).
Hart et al., Direct stimulation of the guanine nucleotide exchange activity of p115 RhoGEF by Galpha13, Science, 280(5372):2112-4 (Jun. 1998).
Hart et al., Identification of a novel guanine nucleotide exchange factor for the Rho GTPase, J. Biol. Chem., 271(41):25452-8 (Oct. 1996).
Heo et al., Indatraline inhibits Rho- and calcium-mediated glioblastoma cell motility and angiogenesis, Biochem. Biophys. Res. Commun., 443(2):749-55 (Jan. 2014).
Hinz et al., Recent developments in myofibroblast biology: paradigms for connective tissue remodeling, Am. J. Pathol., 180(4):1340-55 (Apr. 2012).
Hu et al., Myofibroblasts, Curr. Opin. Rheumatol., 25(1):71-7 (Jan. 2013).
Huang et al., Matrix stiffness-induced myofibroblast differentiation is mediated by intrinsic mechanotransduction, Am. J. Respir. cell Mol. Biol., 4793):340-8 (Sep. 2012).
Ikoma et al., A definitive role of RhoC in metastasis of orthotopic lung cancer in mice, Clin. Cancer Res., 10(3):1192-200 (Feb. 2004).
Iwahara et al., CrkII induces serum response factor activation and cellular transformation through its function in Rho activation, Oncogene, 22(38):5946-57 (Sep. 2003).
Jin et al., Increased SRF transcriptional activity in human and mouse skeletal muscle is a signature of insulin resistance, J. Clin. Invest., 12193):918-29 (Mar. 2011).
Jin et al., RhoA/Rho-kinase in erectile tissue: mechanisms of disease and therapeutic insights, Clin. Sci. (Lond.), 110(2):153-65 (Feb. 2006).
Johnson et al., Novel Rho/MRTF/SRF inhibitors block matrix-stiffness and TGF-β-induced fibrogenesis in human colonic myofibroblasts, Inflamm. Bowel Dis., 20(1):154-65 (Jan. 2014).
Kau et al., Calyculin A sensitive protein phosphatase is required for Bacillus anthracis lethal toxin induced cytotoxicity, Curr. Microbiol., 44(2):106-11 (Feb. 2002).
Kourlas et al., Identification of a gene at 11q23 encoding a guanine nucleotide exchange factor: evidence for its fusion with MLL in acute myeloid leukemia, Proc. Natl. Acad. Sci. USA, 97(5):2145-50 (Feb. 2000).
Kranenburg et al., Activation of RhoA by lysophosphatidic acid and Galpha12/13 subunits in neuronal cells: induction of neurite retraction, Mol. Biol. Cell, 10(6):1851-7 (Jun. 1999).
Kuhlmann et al., Reduction of cisplatin toxicity in cultured renal tubular cells by the bioflavonoid quercetin, Arch. Toxicol., 72(8):536-40 (Jul.-Aug. 1998).
Lu et al., Signaling through Rho GTPase pathway as viable drug target, Curr. Med. Chem., 16(11):1355-65 (2009).
Luchsinger et al., Myocardin-related transcription factor-A complexes activate type I collagen expression in lung fibroblasts, J. Biol. Chem., 286(51):44116-25 (Dec. 2011).
Mae et al., Combination of small molecules enhances differentiation of mouse embryonic stem cells into intermediate mesoderm through BMP7-positive cells, Biochem. Biophys. Res. Commun., 393(4):877-82 (Mar. 2010).
Majumdar et al., A rho exchange factor mediates thrombin and Galpha(12)-induced cytoskeletal responses, J. Biol. Chem., 274(38):26815-21 (Sep. 1999).
Mao et al., Guanine nucleotide exchange factor GEF115 specifically mediates activation of Rho and serum response factor by the G protein alpha subunit Galpha13, Proc. Natl. Acad. Sci. USA, 95(22):12973-6 (Oct. 1998).

(56) References Cited

OTHER PUBLICATIONS

Masszi et al., Central role for Rho in TGF-beta1-induced alpha-smooth muscle actin expression during epithelial-mesenchymal transition, Am. J. Physiol. Renal Physiol., 284(5):F911-24 (May 2003).
Matsui et al., Rho-kinase phosphorylates COOH-terminal threonines of ezrin/radixin/moesin (ERM) proteins and regulates their head-to-tail association, J. Cell Biol., 140(3):647-57 (Feb. 1998).
Medjkane et al., Myocardin-related transcription factors and SRF are required for cytoskeletal dynamics and experimental metastasis, Nat. Cell Biol., 11(3):257-68 (Mar. 2009).
Mercher et al., Recurrence of OTT-MAL fusion in t(1;22) of infant AML-M7, Genes Chromosomes Cancer, 33(1):22-8 (Jan. 2002).
Mercher et al., The OTT-MAL fusion oncogene activates RBPJ-mediated transcription and induces acute megakaryoblastic leukemia in a knockin mouse model, J. Clin. Invest., 119(4):852-64 (Apr. 2009).
Mertsch et al., Opposing signaling of ROCK1 and ROCK2 determines the switching of substrate specificity and the mode of migration of glioblastoma cells, Mol. Neurobiol., 49(2):900-15 (Apr. 2014).
Miralles et al., Actin dynamics control SRF activity by regulation of its coactivator MAL, Cell, 113(3):329-42 (May 2003).
Moravek et al., Determination of the toxic potential of Bacillus cereus isolates by quantitative enterotoxin analyses, FEMS Microbiol. Lett., 257(2):293-8 (Apr. 2006).
Mosmann, Rapid colorimetric assay for cellular growth and survival: application to proliferation and cytotoxicity assays, J. Immunol. Methods, 65(1-2):55-63 (Dec. 1983).
Naeije et al., Expert opinion on available options treating pulmonary arterial hypertension, Expert Opin. Pharmacother., 8(14):2247-65 (Oct. 2007).
Neubig et al., Regulators of G-protein signalling as new central nervous system drug targets, Nat. Rev. Drug Discov., 1(3):187-97 (Mar. 2002).
Ngamwongsatit et al., WST-1-based cell cytotoxicity assay as a substitute for MTT-based assay for rapid detection of toxigenic Bacillus species using CHO cell line, J. Microbiol. Methods, 73(3):211-5 (Jun. 2008).
Noma et al., Physiological role of ROCKs in the cardiovascular system, Am. J. Physiol. Cell Physiol., 290(3):C661-8 (Mar. 2006).
Norman et al., Isolation and properties of cDNA clones encoding SRF, a transcription factor that binds to the c-fos serum response element, Cell, 55(6):989-1003 (Dec. 1988).
Opyrchal et al., Inhibition of Rho-associated coiled-coil-forming kinase increases efficacy of measles virotherapy, Cancer Gene Ther., 20(11):630-7 (Nov. 2013).
Prencipe et al., Identification of transcription factors associated with castration-resistance: is the serum responsive factor a potential therapeutic target?, Prostate, 73(7):743-53 (May 2013).
Psichari et al., High activity of serum response factor in the mesenchymal transition of epithelial tumor cells is regulated by RhoA signaling, J. Biol. Chem., 277(33):29490-5 (Aug. 2002).
Reid et al., Rhotekin, a new putative target for Rho bearing homology to a serine/threonine kinase, PKN, and rhophilin in the rho-binding domain, 271(23):13556-60 (Jun. 1996).
Sah et al., The role of Rho in G protein-coupled receptor signal transduction, Annu. Rev. Pharmacol. Toxicol., 40:459-89 (2000).
Sahai et al., Differing modes of tumour cell invasion have distinct requirements for Rho/ROCK signalling and extracellular proteolysis, Nat. Cell Biol., 5(8):711-9 (Aug. 2003).
Sahai et al., RHO-GTPases and cancer, Nat. Rev. Cancer, 2(2):133-42 (Feb. 2002).
Sakai et al., LPA1-induced cytoskeleton reorganization drives fibrosis through CTGF-dependent fibroblast proliferation, FASEB J., 27(5):1830-46 (May 2013).
Sandbo et al., Critical role of serum response factor in pulmonary myofibroblast differentiation induced by TGF-beta, Am. J. Respir. Cell Mol. Biol., 41(3):332-8 (Sep. 2009).
Sandbo et al., Delayed stress fiber formation mediates pulmonary myofibroblast differentiation in response to TGF-β, Am. J. Physiol. Lung Cell Mol. Physiol., 301(5):L656-66 (Nov. 2011).
Sappino et al., Smooth muscle differentiation in scleroderma fibroblastic cells, Am. J. Pathol., 137(3):585-91 (Sep. 1990).
Sasazuki et al., Identification of a novel transcriptional activator, BSAC, by a functional cloning to inhibit tumor necrosis factor-induced cell death, J. Biol. Chem., 277(32):28853-60 (Aug. 2002).
Sawyer et al., Cancer metastasis therapeutic targets and drug discovery: emerging small-molecule protein kinase inhibitors, Expert Opin. Investig. Drugs, 13(1):1-19 (Jan. 2004).
Schmidt et al., Guanine nucleotide exchange factors for Rho GTPases: turning on the switch, Genes Dev., 16(13):1587-609 (Jul. 2002).
Scobie et al., Human capillary morphogenesis protein 2 functions as an anthrax toxin receptor, Proc. Natl. Acad. Sci. USA, 100(9):5170-4 (Apr. 2003).
Seasholtz et al., Rho as a mediator of G protein-coupled receptor signaling, Mol. Pharmacol., 55(6):949-56 (Jun. 1999).
Selvaraj et al., Megakaryoblastic leukemia-1/2, a transcriptional co-activator of serum response factor, is required for skeletal myogenic differentiation, J. Biol. Chem., 278(43):41977-87 (Oct. 2003).
Shaposhnikov et al., Myocardin related transcription factors are required for coordinated cell cycle progression, Cell Cycle, 12(11):1762-72 (Jun. 2013).
Shaw et al., The Nf2 tumor suppressor, merlin, functions in Rac-dependent signaling, Dev. Cell, 1(1):63-72 (Jul. 2001).
Shikada et al., Higher expression of RhoC is related to invasiveness in non-small cell lung carcinoma, Clin. Cancer Res., 9(14):5282-6 (Nov. 2003).
Small et al., Myocardin-related transcription factor-a controls myofibroblast activation and fibrosis in response to myocardial infarction, Circ. Res., 107(2):294-304 (Jul. 2010).
Small et al., The actin-MRTF-SRF gene regulatory axis and myofibroblast differentiation, J. Cardiovasc. Transl. Res., 5(6):794-804 (Dec. 2012).
Suzuki et al., Galpha 12 activates Rho GTPase through tyrosine-phosphorylated leukemia-associated RhoGEF, Proc. Natl. Acad. Sci. USA, 100(2):733-8 (Jan. 2003).
Tomasek et al., Mechanoregulated expression of smooth muscle alpha-actin in myofibroblasts is mediated by MRTF-A localization and actin dynamics, FASEB J., 22(1 Suppl) (Mar. 2008). [Abstract only].
Tomasek et al., Myofibroblasts and mechano-regulation of connective tissue remodelling, Nat. Rev. Mol. Cell Biol., 3(5):349-63 (May 2002).
Torres et al., Acute megakaryoblastic leukemia with a four-way variant translocation originating the RBM15-MKL1 fusion gene, Pediatr. Blood Cancer, 56(5):846-9 (May 2011).
Wang et al., Thrombin and lysophosphatidic acid receptors utilize distinct rhoGEFs in prostate cancer cells, J. Biol. Chem., 279(28):28831-4 (Jul. 2004).
Whitehead et al., Rho GTPase-dependent transformation by G protein-coupled receptors, Oncogene, 20(13):1547-55 (Mar. 2001).
Wiseman et al., Hemophagocytosis by leukemic megakaryoblasts in acute myeloid leukemia (megakaryoblastic) with t(1;22)(p13;q13);RBM15-MKL1, J. Pediatr. Hematol. Oncol., 34(7):576-80 (Oct. 2012).
Worthylake et al., RhoA is required for monocyte tail retraction during transendothelial migration, J. Cell Biol., 154(1):147-60 (Jul. 2001).
Wu et al., RhoC induces differential expression of genes involved in invasion and metastasis in MCF10A breast cells, Breast Cancer Res. Treat., 84(1):3-12 (Mar. 2004).
Wynn et al., Mechanisms of fibrosis: therapeutic translation for fibrotic disease, Nat. Med., 18(7):1028-40 (Jul. 2012).
Yang et al., Involvement of serum response factor isoforms in myofibroblast differentiation during bleomycin-induced lung injury, Am. J. Respir. Cell Mol. Biol., 29(5):583-90 (Nov. 2003).
Yu-Wai-Man et al., The role of the MRTF-A/SRF pathway in ocular fibrosis, Invest. Ophthalmol. Vis. Sci., 55(7):4560-7 (Jul. 2014).

(56) References Cited

OTHER PUBLICATIONS

Zhang et al., Lung fibroblast alpha-smooth muscle actin expression and contractile phenotype in bleomycin-induced pulmonary fibrosis, Am. J. Pathol., 148(2):527-37 (Feb. 1996).

Zhou et al., Inhibition of mechanosensitive signaling in myofibroblasts ameliorates experimental pulmonary fibrosis, J. Clin. Invest., 123(3):1096-108 (Mar. 2013).

\* cited by examiner

INHIBITORS OF RHO/MRTF/SRF-MEDIATED GENE TRANSCRIPTION AND METHODS FOR USE OF THE SAME

CROSS REFERENCE TO RELATED APPLICATIONS

This application claims the priority benefit of U.S. Provisional Patent Application No. 62/653,869, filed Apr. 6, 2018, hereby incorporated by reference in its entirety.

STATEMENT OF GOVERNMENT SUPPORT

This invention was made with government support under grant numbers AR066049 and GM115459 awarded by the National Institutes of Health. The government has certain rights in the invention.

BACKGROUND

Technical Field

The present disclosure relates to novel, small molecule inhibitors of Rho-, myocardin-related transcription factor-, and/or serum response factor ("Rho/MRTF/SRF")-mediated gene transcription, and methods of using the small molecules to inhibit Rho/MRTF/SRF-mediated gene transcription and to treat diseases, such as cancer and fibrotic disease.

Description of Related Technology

Cell growth, proliferation, migration, and invasion are dependent on many growth factors, mitogens, and chemotactic agents. The medium for growing cells in tissue culture generally contains serum (e.g., fetal bovine serum) and serum also stimulates migration and invasion of cancer cells and fibroblasts. Treatment of cells with serum results in robust activation of gene transcription via the serum response factor ("SRF") (see Norman et al., Cell 55:989-1003 (1988)). SRF is associated with cellular transformation and epithelial-mesenchymal transformation (see Iwahara et al., Oncogene 22:5946-5957 (2003); Psichari et al., J Biol Chem 277:29490-29495 (2002)).

One key mechanism of activation of SRF by serum involves activation of the Rho GTPases (especially RhoA and RhoC) through G protein-coupled receptors ("GPCRs") and possibly other mechanisms. Activation of RhoA and RhoC induces actin polymerization and release of the transcriptional coactivator, myocardin-related transcription factor ("MRTF") (see Cen et al., Mol Cell Biol 23:6597-6608 (2003); Miralles et al., Cell 113:329-342 (2003); Selvaraj and Prywes, J Biol Chem 278:41977-41987 (2003)). MRTF, which is also known as MKL, was first identified as a site of gene translocation in leukemia (megakaryoblastic leukemia), like the leukemia-associated rhoGEF ("LARG", see Mercher et al., Genes Chromosomes Cancer 33:22-28 (2002)). The protein product of the translocated gene is hyperactive compared to the wild-type protein. MRTF and MKL have also been called modified in acute leukemia ("MAL") and BSAC (see Miralles et al., Cell 113:329-342 (2003); Sasazuki et al., J Biol Chem 277:28853-28860 (2002)). There are two MRTF genes (MRTF-A and MRTF-B or MKL1 and MKL2, respectively). Their actions are largely redundant where both proteins are expressed (see Shaposhnikov, Cell Cycle 12:1762-72 (2013)). MRTF was identified in an antiapoptosis screen for genes that abrogate tumor necrosis factor-induced cell death (see Sasazuki et al., J Biol Chem 277:28853-28860 (2002)). As a consequence of rho signaling, MRTF translocates to the nucleus and binds SRF leading to the expression of c-fos which, along with c-jun, forms the transcription factor AP-1. The AP-1 transcription factor promotes the activity of various MMPs and other cell motility genes (see Benbow and Brinckerhoff, Matrix Biol 15:519-526 (1997)). Expression of these genes leads to cancer cell invasion and metastasis. Thus, there is a link between Rho/MRTF-controlled biological processes and cancer metastasis. Similarly, both LARG and MKL are important players in these processes.

Rho GTPase signaling and MRTF-regulated gene transcription have also been implicated in tissue fibrosis in lung (see Sandbo et al, Am J Respir Cell Mol Biol. 41:332-8 (2009); Luchsinger J Biol Chem. 286:44116-25 (2011)), skin (see Haak et al, J Pharmacol Exp Ther. 349:480-6 (2014)), ocular (see Yu-Wai-Man et al, Invest Ophthalmol Vis Sci. 55: 4560-67 (2014)), and intestine (see Johnson et al, Inflamm Bowel Dis. 20:154-65 (2014)). Many genes involved in fibrosis (alpha-smooth muscle actin, CTGF, and collagen itself) are activated by Rho-regulated MRTF/SRF mechanisms (see Haak et al, J Pharmacol Exp Ther. 349: 480-6, (2014)).

Cancer metastasis is a significant medical problem in the United States, where it is estimated that over 500,000 cancer-related deaths in 2003 resulted from metastatic tumors rather than primary tumors (approximately 90% of cancer deaths). Cancer metastasis requires malfunction in several tightly regulated cellular processes controlling cell movement from a primary site to a secondary site. These cellular processes include cell survival, adhesion, migration, and proteolysis resulting in extracellular matrix remodeling, immune escape, angiogenesis and lymphangiogenesis, and target 'homing'. Most existing cancer treatments focus on killing tumor cells; however, such chemotherapeutic intervention leads to substantial toxicity to healthy cells and tissue. Since spread, or metastasis, of cancers is the primary cause of cancer-related mortalities, there is a need for agents that can specifically inhibit or prevent signals that trigger metastasis.

Rho proteins are overexpressed in various tumors, including colon, breast, lung, testicular germ cell, and head and neck squamous-cell carcinoma (see Sawyer, Expert Opin. Investig. Drugs., 13: 1-9 (2004)). The rho family of small GTP binding proteins plays important roles in many normal biological processes and in cancer (see Schmidt and Hall, Genes Dev., 16:1587-1609 (2002); Burridge and Wennerberg, Cell, 116:167-179 (2004)). This family includes three main groups: rho, rac, and cdc42. Rho is activated by numerous external stimuli including growth factor receptors, immune receptors, cell adhesion, and G protein coupled receptors (GPCRs) (see Schmidt and Hall, Genes Dev., 16:1587-1609 (2002), Sah et al., Annu. Rev. Pharmacol. Toxicol., 40:459-489 (2000)).

RhoA and rhoC play roles in metastasis (see Clark et al., Nature 406:532-535 (2000); Ikoma et al., Clin Cancer Res 10:1192-1200 (2004); Shikada et al., Clin Cancer Res 9:5282-5286 (2003); Wu et al., Breast Cancer Res Treat 84:3-12 (2004); Hakem et al, Genes Dev 19:1974-9 (2005). Both rhoA and rac1 can regulate the function of the extracellular matrix (ECM) proteins, ezrin, moesin, and radixin, by the phosphorylation of ezrin via the rhoA pathway and the phosphorylation of the ezrin antagonist, neurofibromatosis 2, by the rac1 pathway (see Shaw et al., Dev Cell 1:63-72 (2001); Matsui et al., J Cell Biol 140:647-657 (1998)). These ECM proteins promote cell movement by utilizing the ECM receptor, CD44, to link the actin cytoskeleton with the plasma membrane. In addition, rhoA and rac1 regulate ECM remodeling by controlling the levels of matrix metalloproteinases (MMPs) or their antagonists, tissue inhibitors of metalloproteinases (TIMPs) (see Bartolome et al., Cancer Res 64:2534-2543 (2004)). RhoA is also required for monocyte tail retraction during transendothelial migration, indicating a role in extravasation, which is a key process in metastasis (see Worthylake et al., J Cell Biol 154:147-160 (2001).

The relative contributions of rho and rac proteins in the metastatic phenotype has been studied (see Sahai and Marshall, Nat Rev Cancer 2:133-142 (2002); Whitehead et al., Oncogene 20:1547-1555 (2001)). Sahai and Marshall (see Nat Cell Biol 5:711-719 (2003)) showed that different tumor cell lines exhibit different mechanisms of motility and invasion. In particular, 375m2 melanoma and LS174T colon carcinoma cell lines showed striking "rounded" and "blebbed" morphology during invasion into Matrigel matrices. This invasion was entirely rho-dependent and was blocked by C3 exotoxin, the N17rho dominant negative protein, and a ROCK kinase inhibitor. In contrast, two other cell lines were blocked instead by a rac dominant negative mutation, but not rho or ROCK inhibitors. These latter two cell lines (BE colon carcinoma and SW962 squamous cell carcinoma) had elongated morphologies. A third line showed a mixed morphology and was blocked partially by both rho and rac inhibitors. Additionally, mice lacking rhoC have greatly reduced metastasis of virally-induced breast tumors to lung (see Hakem et al, Genes Dev 19:1974-9 (2005)). Also, knock-down of SRF or its transcriptional co-activator MKL reduced lung metastases from breast or melanoma xenografts (see Medjkane et al, Nat Cell Biol. 11:257-68 (2009)). Thus, there is important heterogeneity in mechanisms of tumor cell behavior that contributes to metastasis. It is widely recognized that cell growth and apoptosis mechanisms vary greatly among tumors, necessitating customized therapeutic approaches.

Nearly 40% of chronic diseases such as cirrhosis, heart failure, and diabetic nephropathy are characterized by fibrosis or excess deposition of extracellular matrix, including collagen. The poor clinical outcome of several orphan diseases (scleroderma or systemic sclerosis ("SSc"), idiopathic pulmonary fibrosis ("IPF") etc.) is primarily determined by tissue fibrosis.

Systemic sclerosis is an orphan, multisystem autoimmune disorder that can cause fibrosis of the skin and internal organ systems (lungs, heart, kidneys, and gastrointestinal system). It has the highest case fatality rate of any rheumatic disease. SSc predominately affects women (see Beyer et al., Arthritis Rheum 62: 2831-2844 (2010); Boukhalfa G, et al., Exp Nephrol 4: 241-247 (1996); Buhl A M, et al., J Biol Chem 270: 24631-24634 (1995); Chaqour et al., FEBS J 273: 3639-3649 (2006); Charles et al., Lancet 367: 1683-1691 (2006) and increases with age. The precise pathogenesis of SSc is yet to be defined but the major clinical features of SSc-collagen production, vascular damage and inflammation/autoimmunity-require environmental triggers and genetic effects which interact with the three cardinal features of the disease at several points (see Charles et al., Lancet 367: 1683-1691 (2006)). Generally, there is initial inflammation but fibrosis persists even after the inflammation has resolved or has been suppressed by medications (see Beyer et al., Curr Opin Rheumatol 24: 274-280 (2012); Wynn T A, and Ramalingam T R. Nat Med 18: 1028-1040 (2012)).

Therefore, there is a need for new compounds and methods for targeted therapy that can treat and manage diseases, such as cancer and fibrosis.

SUMMARY

One aspect of the disclosure provides a compound of Formula (I), or a pharmaceutically acceptable salt thereof:

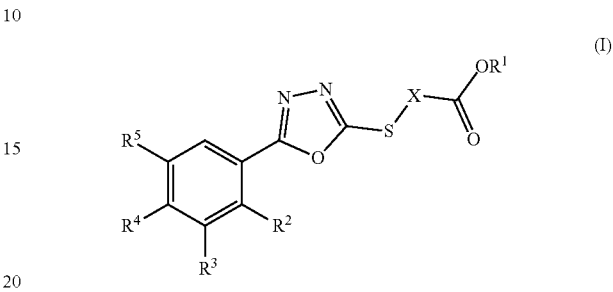

wherein X is —$CH_2CH_2CH_2$— or $C_{3-6}$cycloalkylenyl; $R^1$ is H or $C_{1-3}$alkyl; $R^2$ is H, OH, Cl, F, or $CF_3$; when X is —$CH_2CH_2CH_2$—, then $R^3$, $R^4$, and $R^5$ are each independently selected from the group consisting of H, $C_{1-5}$fluoroalkyl, $OC_{1-5}$fluoroalkyl, $C_{0-3}$alkylene-$C_{3-5}$cycloalkyl, $OC_{0-3}$alkylene-$C_{3-5}$cycloalkyl, $C_{0-3}$alkylene-$C_{2-4}$heterocycloalkyl, and $OC_{0-3}$alkylene-$C_{2-4}$heterocycloalkyl, wherein the cycloalkyl and heterocycloalkyl are each optionally substituted with one or more fluorine atoms, and the heterocycloalkyl comprises one oxygen ring atom, and; when X is $C_{3-6}$cycloalkylenyl, then $R^3$, $R^4$, and $R^5$ are each independently selected from the group consisting of H, halo, $C_{1-7}$alkyl, $OC_{1-7}$alkyl, $C_{3-7}$cycloalkyl, $OC_{3-7}$cycloalkyl, $C_{2-4}$heterocycloalkyl, and $OC_{2-4}$heterocycloalkyl, wherein one or two carbon atoms of the alkyl group can optionally be replaced with oxygen, and the heterocycloalkyl group comprises one oxygen ring atom; and when X is —$CH_2CH_2CH_2$— and $R^2$ is H, OH, or Cl, then at least one of $R^3$, $R^4$, and $R^5$ is not H.

In some embodiments, $R^1$ is H or methyl. In some cases, $R^1$ is H. In various embodiments, $R^2$ is H. In various cases, $R^2$ is OH, F, or $CF_3$. In some cases, $R^2$ is Cl.

In some embodiments, X is —$CH_2CH_2CH_2$—. In some cases, $R^3$ is H. In various cases, $R^3$ is $C_{1-5}$fluoroalkyl or $OC_{1-5}$fluoroalkyl, such as $CH_2F$, $CHF_2$, $CF_3$, $CF(CH_3)_2$, $CH_2CF_3$, $OCH_2F$, $OCHF_2$, $OCF_3$, $OCF(CH_3)_2$, and $OCH_2CF_3$. In some embodiments, $R^3$ is $C_{0-3}$alkylene-$C_{3-5}$cycloalkyl, $OC_{0-3}$alkylene-$C_{3-5}$cycloalkyl, $C_{0-3}$alkylene-$C_{2-4}$heterocycloalkyl, or $OC_{0-3}$alkylene-$C_{2-4}$heterocycloalkyl, wherein the cycloalkyl and heterocycloalkyl are each optionally substituted with one or more fluorine atoms, and the heterocycloalkyl comprises one oxygen ring atom. In some cases, $R^3$ comprises cyclopropyl or oxetanyl. In various cases, $R^3$ is selected from the group consisting of H, $CF_3$, $OCH_2CF_3$, and cyclopropyl. In some embodiments, $R^4$ is H. In various embodiments, $R^4$ is $C_{1-5}$fluoroalkyl or $OC_{1-5}$fluoroalkyl, such as $CH_2F$, $CHF_2$, $CF_3$, $CF(CH_3)_2$, $CH_2CF_3$, $OCH_2F$, $OCHF_2$, $OCF_3$, $OCF(CH_3)_2$, and $OCH_2CF_3$. In various cases, $R^4$ is $C_{0-3}$alkylene-$C_{3-5}$cycloalkyl, $OC_{0-3}$alkylene-$C_{3-5}$cycloalkyl, $C_{0-3}$alkylene-$C_{2-4}$heterocycloalkyl, or $OC_{0-3}$alkylene-$C_{2-4}$heterocycloalkyl, wherein the cycloalkyl and heterocycloalkyl are each optionally substituted with one or more fluorine atoms, and the heterocycloalkyl comprises one oxygen ring atom.

In some cases, $R^4$ comprises cyclopropyl or oxetanyl. In some embodiments, $R^4$ is selected from the group consisting of

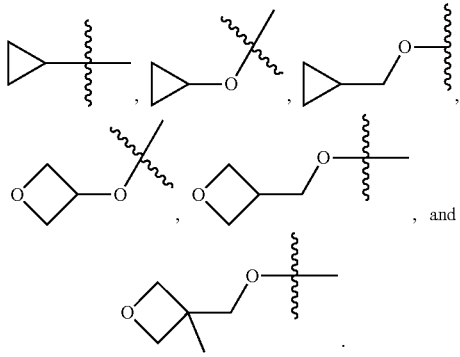

In various cases, $R^4$ is selected from the group consisting of H, $CHF_2$, $CF_3$, $OCF_3$, $OCHF_2$, $OCH_2CF_3$, $CF(CH_3)_2$,

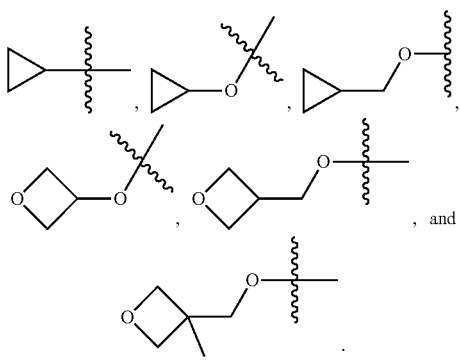

In various embodiments, $R^5$ is H. In some cases, $R^5$ is $C_{1-5}$fluoroalkyl or $OC_{1-5}$fluoroalkyl. In various cases, $R^5$ is $CH_2F$, $CHF_2$, $CF_3$, $CF(CH_3)_2$, $CH_2CF_3$, $OCH_2F$, $OCHF_2$, $OCF_3$, $OCF(CH_3)_2$, and $OCH_2CF_3$. In some embodiments, $R^5$ is $C_{0-3}$alkylene-$C_{3-5}$cycloalkyl, $OC_{0-3}$alkylene-$C_{3-5}$cycloalkyl, $C_{0-3}$alkylene-$C_{2-4}$heterocycloalkyl, or $OC_{0-3}$alkylene-$C_{2-4}$heterocycloalkyl, wherein the cycloalkyl and heterocycloalkyl are each optionally substituted with one or more fluorine atoms, and the heterocycloalkyl comprises one oxygen ring atom. In various cases, $R^5$ comprises cyclopropyl or oxetanyl. In some embodiments, $R^5$ is selected from the group consisting of

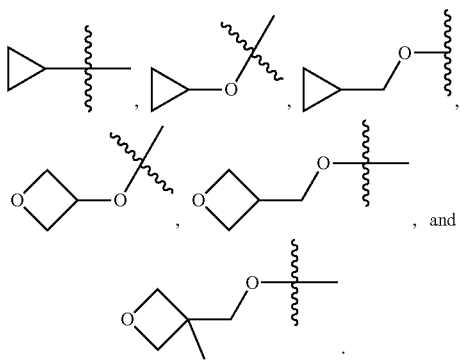

In various cases, $R^5$ is H or

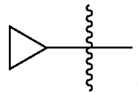

Yet another aspect of the disclosure provides a compound listed in Table A (e.g., A1-A28) or a pharmaceutically acceptable salt thereof. In various embodiments, disclosed herein is compound A9, A24, A26, and A27. In some cases, the compound of Formula (I) is selected from the group consisting of A1-A8, A10-A23, and A25. In various cases, the compound of Formula (I) is selected from the group consisting of A1, A7, A10, and A21.

In some embodiments, X is $C_{3-6}$cycloalkylenyl. In various embodiments, the two ring substituents are trans. In some cases, the two ring substituents are cis. In some cases, the $C_{3-6}$cycloalkylenyl is selected from the group consisting of cyclobutyl, cyclopentyl, and cyclohexyl. In some embodiments, $R^3$ is H. In various embodiments, $R^3$ is halo, such as Cl. In some embodiments, $R^3$ is $C_{1-7}$alkyl or $OC_{1-7}$alkyl, wherein one or two carbon atoms of the alkyl can optionally be replaced with oxygen. In various cases, $R^3$ is $C_{3-7}$cycloalkyl, $OC_{3-7}$cycloalkyl, $C_{2-4}$heterocycloalkyl, or $OC_{2-4}$heterocycloalkyl, wherein the heterocycloalkyl group comprises one oxygen ring atom, such as cyclopropyl, cyclobutyl, oxiranyl, or oxetanyl. In some embodiments, $R^4$ is H. In various embodiments, $R^4$ is halo, such as Cl. In various cases, $R^4$ is $C_{1-7}$alkyl or $OC_{1-7}$alkyl, wherein one or two carbon atoms of the alkyl can optionally be replaced with oxygen. In some cases, $R^4$ is $CHF_2$, $CF_3$, $CH_2CF_3$, or $CF(CH_3)_2$. In various cases, $R^4$ is $C_{3-7}$cycloalkyl, $OC_{3-7}$cycloalkyl, $C_{2-4}$heterocycloalkyl, or $OC_{2-4}$heterocycloalkyl, wherein the heterocycloalkyl group comprises one oxygen ring atom. In some embodiments, $R^4$ comprises cyclopropyl, cyclobutyl, oxiranyl, or oxetanyl. In various embodiments, $R^4$ is selected from the group consisting of Cl, $CF_3$, and cyclopropyl. In various embodiments, $R^5$ is H. In some cases, $R^5$ is $C_{1-5}$fluoroalkyl or $OC_{1-5}$fluoroalkyl. In various cases, $R^5$ is $CH_2F$, $CHF_2$, $CF_3$, $CF(CH_3)_2$, $CH_2CF_3$, $OCH_2F$, $OCHF_2$, $OCF_3$, $OCF(CH_3)_2$, and $OCH_2CF_3$. In some embodiments, $R^5$ is $C_{0-3}$alkylene-$C_{3-5}$cycloalkyl, $OC_{0-3}$ alkylene-$C_{3-5}$cycloalkyl, $C_{0-3}$alkylene-$C_{2-4}$heterocycloalkyl, or $OC_{0-3}$alkylene-$C_{2-4}$heterocycloalkyl, wherein the cycloalkyl and heterocycloalkyl are each optionally substituted with one or more fluorine atoms, and the heterocycloalkyl comprises one oxygen ring atom. In various cases, $R^5$ comprises cyclopropyl or oxetanyl. In some embodiments, $R^5$ is selected from the group consisting of

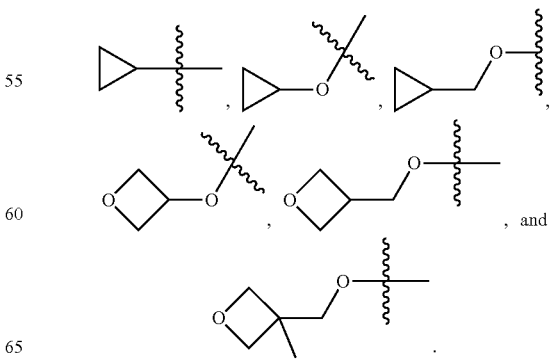

Still another aspect of the disclosure provides a compound listed in Table B or a pharmaceutically acceptable salt thereof, below (e.g., B1-B10). In various cases, the compound of Formula (I) is selected from the group consisting of B2, B3, B5, and B7.

Another aspect of the disclosure relates to a pharmaceutical formulation comprising a compound of Formula (I), a compound listed in Table A (e.g., A1-A27), a compound listed in Table B (e.g., B1-B10), or pharmaceutically acceptable salts of the foregoing, and a pharmaceutically acceptable excipient. In some cases, the pharmaceutical formulation comprises a compound selected from the group consisting of A1-A27 and B1-B10, or pharmaceutically acceptable salts thereof, and combinations thereof, and a pharmaceutically acceptable excipient.

Still another aspect of the disclosure relates to a method of inhibiting Rho/MRTF/SRF-mediated gene transcription in a cell, comprising contacting the cell with a compound of Formula (I), a compound selected from the group consisting of A1-A27, B1-B10, Compound C, and pharmaceutically acceptable salts of the foregoing. In some embodiments, the contacting occurs in vivo. In various embodiments, the contacting comprises administering to a patient in need thereof. In some cases, the patient suffers from a disease associated with dysfunction of Rho/MRTF/SRF-mediated gene transcription.

Yet another aspect of the disclosure relates to a method of treating a disease associated with dysfunction of Rho/MRTF/SRF-mediated gene transcription in a patient comprising administering to the patient a therapeutically effective amount of a compound of Formula (I), a compound selected from the group consisting of A1-A27, B1-B10, Compound C, and pharmaceutically acceptable salts of the foregoing. In some embodiments, the disease is selected from the group consisting of cancer, fibrotic disease, diabetes, insulin sensitivity, hyperactive platelets, metabolic disease, inflammation, inflammatory disease, pulmonary arterial hypertension, axon regeneration following nerve damage, Raynaud's phenomenon, cerebral vascular disease, cardiovascular disease, erectile dysfunction, and combinations thereof.

In some cases, the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, glioblastoma, leukemia, megakaryoblastic leukemia, polycythemia vera, lymphoma, multiple myeloma, Waldenstrom's macroglobulinemia, heavy chain disease, and combinations thereof. For example, the cancer can be megakaryoblastic leukemia, melanoma, breast cancer, prostate cancer, glioblastoma, or combinations thereof. In some cases the melanoma is cutaneous or uveal.

In some cases, the fibrotic disease is systemic sclerosis, pulmonary fibrosis, cardiac fibrosis, liver fibrosis, liver cirrhosis, renal fibrosis, chronic renal failure, diabetic nephropathy, lung fibrosis, nephrogenic systemic fibrosis, graft versus host disease, Dupuytren's contracture, inflammatory bowel disease, Crohn's disease, ocular fibrosis, diabetic retinopathy, age-related macular degeneration, postoperative adhesions, reactive fibrosis, chronic heart failure, glaucoma, post-trabeculectomy fibrosis, corneal fibrosis, pterygia, Graves opthmalopathy, or combinations thereof. For example, the fibrotic disease can be systemic sclerosis or idiopathic pulmonary fibrosis.

In some cases, the metabolic disease is obesity, diabetes (e.g., type II diabetes), insulin resistance, or combinations thereof.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

DETAILED DESCRIPTION

Figure 1:
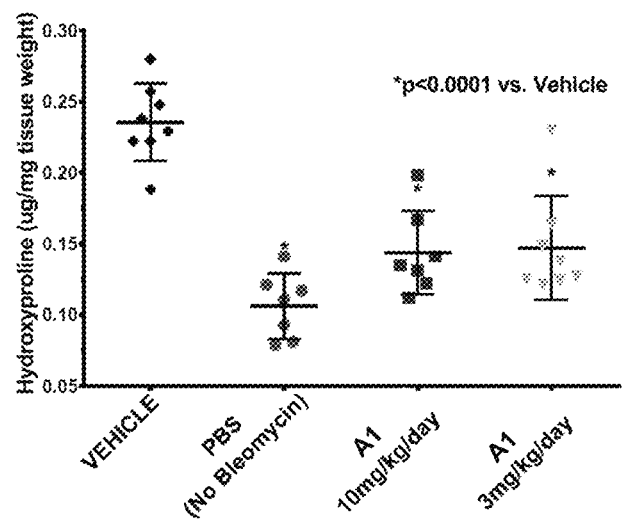
FIG. 1 depicts the reduction in hydroxyproline content in mice treated with compound A1, as further described in the Examples section.

Disclosed herein are compounds that can inhibit Rho-, myocardin-related transcription factor-, and/or serum response factor ("Rho/MRTF/SRF")-mediated gene transcription. The compounds disclosed herein demonstrate potency over other small molecule inhibitors (e.g., up to 100 times more potent than pirfenidone at inhibiting myofibroblast markers in SSc dermal fibroblasts in vitro). The inhibitors disclosed herein can be used to treat or prevent diseases, such as cancer or fibrotic disease.

The inhibitors disclosed herein have a structure of Formula (I), wherein the substituents are described in detail below.

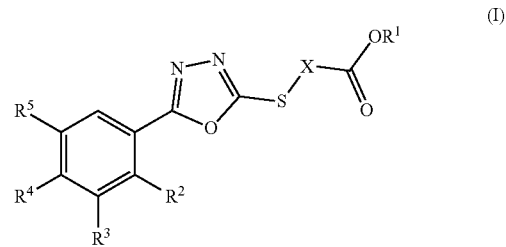

In various cases, the compounds described herein can inhibit the serum response element (SRE) with an $IC_{50}$ up to about 1000 nM, or up to about 750 nM, or up to about 500 nM, or up to about 250 nM, or up to about 100 nM, or up to about 90 nM, or up to about 80 nM, or up to about 70 nM, or up to about 60 nM, or up to about 50 nM, or up to about 40 nM, or up to about 30 nM, or up to about 20 nM, or up to about 10 nM, or up to about 5 nM or up to about 1 nM, or up to about 0.1 nM, or up to about 0.001 nM. In various cases, the $IC_{50}$ value of the compounds described herein is about 0.001 nM to about 1000 nM, 1 nM to about 500 nM, or about 10 nM to about 200 nM, or about 0.1 nM to about 100 nM.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. For example, an alkyl group can be substituted with one or more fluorine atoms to form a fluoroalkyl group (e.g., a methyl group can be substituted with 1 to 3 fluorine atoms to form $CH_2F$, $CHF_2$, or $CF_3$).

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_{2-7}$ alkenyl refers to an alkenyl group having a number of carbon atoms encompassing the entire range (e.g., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkylene" refers to an alkyl group having a substituent. For example, the term "alkylene-aryl" refers to an alkyl group substituted with an aryl group. For example, an alkylene group can be $-CH_2CH_2-$ or $-CH_2-$. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "cycloalkyl" refers to a monovalent aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (e.g., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to eight carbon atoms. Cycloalkyl groups can be saturated or partially unsaturated ring systems optionally substituted with, for example, one to three groups, independently selected alkyl, alkylene-OH, C(O)$NH_2$, $NH_2$, oxo (=O), aryl, haloalkyl, halo, and OH.

As used herein, the term "cycloalkylene" refers to a bivalent cycloalkyl group. For example, the term "cycloalkylene-aryl" refers to an cyclalkylene group substituted with an aryl group. The term $C_n$ means the cycloalkylene group has "n" carbon atoms. For example, $C_{3-6}$cycloalkylene refers to a cycloalkylene group having a number of carbon atoms encompassing the entire range, as well as all subgroups, as previously described for "cycloalkyl" groups.

As used herein, the term "heterocycloalkyl" is defined similarly as cycloalkyl, except the ring contains one to three heteroatoms independently selected from oxygen, nitrogen, or sulfur. In particular, the term "heterocycloalkyl" refers to a ring containing a total of three to eight atoms, of which 1, 2, 3 or three of those atoms are heteroatoms independently selected from the group consisting of oxygen, nitrogen, and sulfur, and the remaining atoms in the ring are carbon atoms. Nonlimiting examples of heterocycloalkyl groups include piperdine, tetrahydrofuran, tetrahydropyran, dihydrofuran, morpholine, and the like. Heterocycloalkyl groups can be saturated or partially unsaturated ring systems optionally substituted with, for example, one to three groups, independently selected alkyl, alkyleneOH, C(O)$NH_2$, $NH_2$, oxo (=O), aryl, haloalkyl, halo, and OH. Heterocycloalkyl groups optionally can be further N-substituted with alkyl, hydroxyalkyl, alkylene-aryl, and alkylene-heteroaryl. The heterocycloalkyl groups described herein can be isolated or fused to another heterocycloalkyl group, a cycloalkyl group, an aryl group, and/or a heteroaryl group. When a heterocycloalkyl group is fused to another heterocycloalkyl group, then each of the heterocycloalkyl groups can contain three to eight total ring atoms, and one to three heteroatoms. In some embodiments, the heterocycloalkyl groups described herein comprise one oxygen ring atom (e.g., oxiranyl, oxetanyl, tetrahydrofuranyl, and tetrahydropyranyl).

As used herein, the term "aryl" refers to a cyclic aromatic group, such as a monocyclic aromatic group, e.g., phenyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a cyclic aromatic ring having five to twelve total ring atoms (e.g., a monocyclic aromatic ring with 5-6 total ring atoms), and containing one to three heteroatoms selected from nitrogen, oxygen, and sulfur atom in the aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Heteroaryl groups can be isolated (e.g., pyridyl) or fused to another heteroaryl group (e.g., purinyl), a cycloalkyl group (e.g., tetrahydroquinolinyl), a heterocycloalkyl group (e.g., dihydronaphthyridinyl), and/or an aryl group (e.g., benzothiazolyl and quinolyl). Examples of heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. When a heteroaryl group is fused to another heteroaryl group, then each ring can contain five or six total ring atoms and one to three heteroatoms in its aromatic ring.

As used herein, the term "halo" refers to a fluoro, chloro, bromo, or iodo group. The term "haloalkyl" refers to an alkyl group that is substituted with at least one halogen.

As used herein, the term "ether" refers to a "alkyl-O-alkyl" group. The ether group can be unsubstituted or substituted.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds that ameliorates, attenuates or eliminates one or more symptoms of a particular disease or condition, or prevents or delays the onset of one of more symptoms of a particular disease or condition.

As used herein, the terms "patient" and "subject" may be used interchangeably and mean animals, such as dogs, cats, cows, horses, and sheep (e.g., non-human animals) and humans. Particular patients or subjects are mammals (e.g., humans). The terms patient and subject includes males and females.

As used herein, the term "pharmaceutically acceptable" means that the referenced substance, such as a compound of the present disclosure, or a formulation containing the compound, or a particular excipient, are safe and suitable for administration to a patient or subject. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment. In some cases, the treating refers to treating a symptom of a disorder or disease as disclosed herein.

As used herein, the term "excipient" means any pharmaceutically acceptable additive, carrier, diluent, adjuvant, or other ingredient, other than the active pharmaceutical ingredient (API).

As used herein the term "rho" or "rho protein" refers to the rho subfamily that includes rhoA, rhoB, rhoC, and others, and is described in Sahai and Marshall Nat. Rev. Cancer 2:133-142 (2002).

As used herein, "Rho/MRTF/SRF-mediated gene transcription" refers to gene transcription that is mediated by the rho protein, myocardin-related transcription factor, and/or serum response factor.

As used herein, the term "dysfunction of Rho/MRTF/SRF-mediated gene transcription" relates to an abnormality or impairment gene transcription that is mediated by Rho, MRTF, and/or SRF.

As used herein, the term "fibrotic disease" relates to diseases involving fibrosis, which may, e.g., be due to chronic inflammation or repair and reorganization of tissues. Fibrosis may involve any organ of the human body (e.g. the skin, lung, pancreas, liver or kidney). Therefore, the disclosure also relates to treatment and/or prevention of fibrotic diseases such as systemic sclerosis, pulmonary fibrosis, cardiac fibrosis, liver fibrosis, liver cirrhosis, renal fibrosis, chronic renal failure, diabetic nephropathy, lung fibrosis, nephrogenic systemic fibrosis, graft versus host disease, Dupuytren's contracture, inflammatory bowel disease, Crohn's disease, ocular fibrosis, diabetic retinopathy, age-related macular degeneration, keloid and other scarring/wound healing abnormalities, postoperative adhesions, reactive fibrosis, chronic heart failure (e.g., after myocardial infarction), glaucoma, post-trabeculectomy fibrosis, corneal fibrosis, pterygia, Graves opthmalopathyor combinations thereof.

Small Molecule Inhibitors of Rho/MRTF/SRF-Mediated Gene Transcription

Provided herein are compounds of Formula (I), or pharmaceutically acceptable salts thereof:

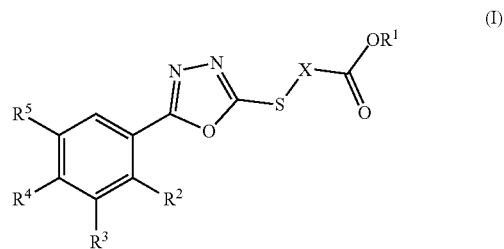

(I)

wherein: X is —CH$_2$CH$_2$CH$_2$— or C$_{3-6}$cycloalkylenyl; R$^1$ is H or C$_{1-3}$alkyl; R$^2$ is H, OH, Cl, F, or CF$_3$; when X is —CH$_2$CH$_2$CH$_2$—, then R$^3$, R$^4$, and R$^5$ are each independently selected from the group consisting of H, C$_{1-5}$fluoroalkyl, OC$_{1-5}$fluoroalkyl, C$_{0-3}$alkylene-C$_{3-5}$cycloalkyl, OC$_{0-3}$alkylene-C$_{3-5}$cycloalkyl, C$_{0-3}$alkylene-C$_{2-4}$heterocycloalkyl, and OC$_{0-3}$alkylene-C$_{2-4}$heterocycloalkyl, wherein the cycloalkyl and heterocycloalkyl are each optionally substituted with one or more fluorine atoms, and the heterocycloalkyl comprises one oxygen ring atom, and; when X is C$_{3-6}$cycloalkylenyl, then R$^3$, R$^4$, and R$^5$ are each independently selected from the group consisting of H, halo, C$_{1-7}$alkyl, OC$_{1-7}$alkyl, C$_{3-7}$cycloalkyl, OC$_{3-7}$cycloalkyl, C$_{2-4}$heterocycloalkyl, and OC$_{2-4}$heterocycloalkyl, wherein one or two carbon atoms of the alkyl group can optionally be replaced with oxygen, and the heterocycloalkyl group comprises one oxygen ring atom; and when X is —CH$_2$CH$_2$CH$_2$— and R$^2$ is H, OH, or Cl, then at least one of R$^3$, R$^4$, and R$^5$ is not H. In some embodiments, when X is —CH$_2$CH$_2$CH$_2$— and R$^2$ is H, OH, or Cl, only one of R$^3$, R$^4$, and R$^5$ is not H.

In some cases, R$^1$ is H. In some embodiments, R$^1$ is C$_{1-3}$alkyl. In various embodiments, R$^1$ is CH$_3$. In various cases, R$^1$ is H or CH$_3$.

In some embodiments, R$^2$ is H. In various embodiments, R$^2$ is OH, F, or CF$_3$. In some embodiments, R$^2$ is Cl. In some cases, R$^2$ is OH. In various cases, R$^2$ is F or CF$_3$.

In some cases, X is —CH$_2$CH$_2$CH$_2$— and R$^3$, R$^4$, and R$^5$ are each independently selected from the group consisting of H, C$_{1-5}$fluoroalkyl, OC$_{1-5}$fluoroalkyl, C$_{0-3}$alkylene-C$_{3-5}$cycloalkyl, OC$_{0-3}$alkylene-C$_{3-5}$cycloalkyl, C$_{0-3}$alkylene-C$_{2-4}$heterocycloalkyl, and OC$_{0-3}$alkylene-C$_{2-4}$heterocycloalkyl, wherein the cycloalkyl and heterocycloalkyl are each optionally substituted with one or more fluorine atoms, and the heterocycloalkyl comprises one oxygen ring atom. The compounds can exhibit desired potency and metabolic stability when X is a propylene group and at least one of R$^3$, R$^4$, and R$^5$ comprises a fluoroalkyl, Ofluoroalkyl, cycloalkyl, or single O-containing heterocycloalkyl group, as described in the Examples section.

In some cases, R$^3$ is H. In some embodiments, R$^3$ is C$_{1-5}$fluoroalkyl or OC$_{1-5}$fluoroalkyl, such as CH$_2$F, CHF$_2$, CF$_3$, CF(CH$_3$)$_2$, CH$_2$CF$_3$, OCH$_2$F, OCHF$_2$, OCF$_3$, OCF(CH$_3$)$_2$, and OCH$_2$CF$_3$. In some embodiments, R$^3$ is CF$_3$ or OCH$_2$CF$_3$. In various embodiments, R$^3$ is C$_{0-3}$alkylene-C$_{3-5}$cycloalkyl, OC$_{0-3}$alkylene-C$_{3-5}$cycloalkyl, C$_{0-3}$alkylene-C$_{2-4}$heterocycloalkyl, or OC$_{0-3}$alkylene-C$_{2-4}$heterocycloalkyl, wherein the cycloalkyl and heterocycloalkyl are each optionally substituted with one or more fluorine atoms, and the heterocycloalkyl comprises one oxygen ring atom. For example, R$^3$ can comprise cyclopropyl or oxetanyl (e.g., oxetanyl or methyloxetanyl). In some cases, R$^3$ is cyclopropyl. In various cases, R$^3$ is selected from the group consisting of H, OH, CF$_3$, OCH$_2$CF$_3$, and cyclopropyl.

In some embodiments, R$^4$ is H. In some cases, R$^4$ is C$_{1-5}$fluoroalkyl or OC$_{1-5}$fluoroalkyl, such as is CH$_2$F, CHF$_2$, CF$_3$, CF(CH$_3$)$_2$, CH$_2$CF$_3$, OCH$_2$F, OCHF$_2$, OCF$_3$, OCF(CH$_3$)$_2$, and OCH$_2$CF$_3$. In various cases, R$^4$ is C$_{0-3}$alkylene-C$_{3-5}$cycloalkyl, OC$_{0-3}$alkylene-C$_{3-5}$cycloalkyl, C$_{0-3}$alkylene-C$_{2-4}$heterocycloalkyl, and OC$_{0-3}$alkylene-C$_{2-4}$heterocycloalkyl, wherein the cycloalkyl and heterocycloalkyl are each optionally substituted with one or more fluorine atoms, and the heterocycloalkyl comprises one oxygen ring atom. In some embodiments, R$^4$ comprises cyclopropyl or oxetanyl (e.g., oxetanyl or methyloxetanyl), such as

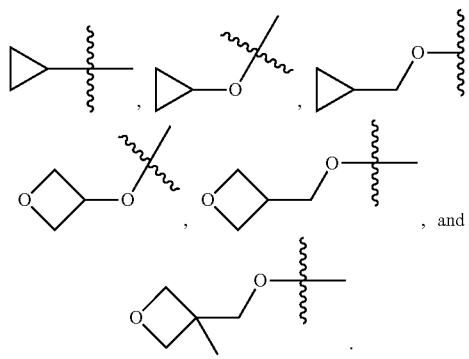

, and

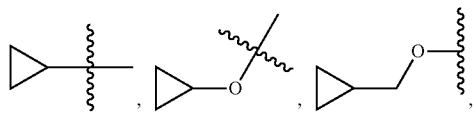

Suitable R$^4$ groups include, for example, H, OH, CHF$_2$, CF$_3$, OCF$_3$, OCHF$_2$, OCH$_2$CF$_3$, CF(CH$_3$)$_2$,

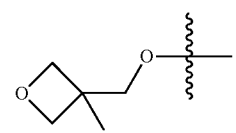

In various embodiments, R$^5$ is H. In some cases, R$^5$ is C$_{1-5}$fluoroalkyl or OC$_{1-5}$fluoroalkyl. In various cases, R$^5$ is CH$_2$F, CHF$_2$, CF$_3$, CF(CH$_3$)$_2$, CH$_2$CF$_3$, OCH$_2$F, OCHF$_2$, OCF$_3$, OCF(CH$_3$)$_2$, and OCH$_2$CF$_3$. In some embodiments, R$^5$ is C$_{0-3}$alkylene-C$_{3-5}$cycloalkyl, OC$_{0-3}$alkylene-C$_{3-5}$cycloalkyl, C$_{0-3}$alkylene-C$_{2-4}$heterocycloalkyl, or OC$_{0-3}$alkylene-C$_{2-4}$heterocycloalkyl, wherein the cycloalkyl and heterocycloalkyl are each optionally substituted with one or more fluorine atoms, and the heterocycloalkyl comprises one oxygen ring atom. In various cases, R$^5$ comprises cyclopropyl or oxetanyl. In some embodiments, R$^5$ is selected from the group consisting of

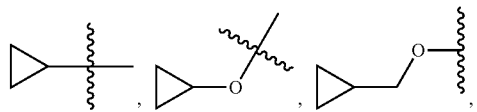

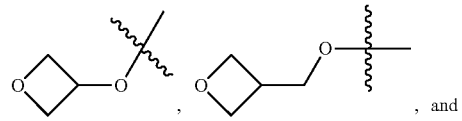

In various cases, R$^5$ is H or

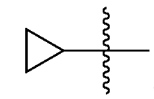

In some embodiments, disclosed herein is a compound listed in Table A or a pharmaceutically acceptable salt thereof (e.g., A1-A27). In various embodiments, disclosed herein are compounds A9, A24, A26, and A27. In some cases, the compound of Formula (I) is selected from the group consisting of A1-A8, A10-A23, and A25. In various cases, the compound of Formula (I) is selected from the group consisting of A1, A7, A10, and A21.

TABLE A

| Compound # | Structure/Name |
|---|---|
| A1 | 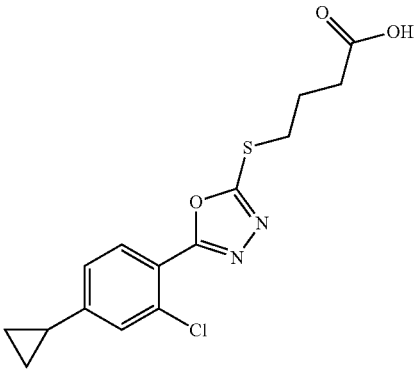<br>4-((5-(2-chloro-4-cyclopropylphenyl)-1,3,4-oxadiazol-2-yl)thio)butanoic acid |
| A2 | 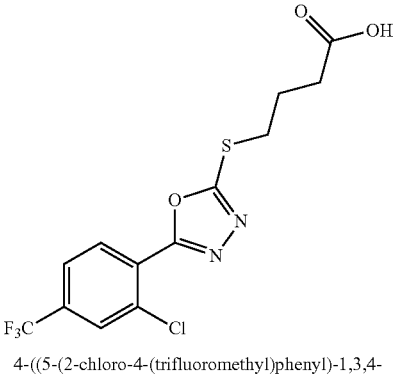<br>4-((5-(2-chloro-4-(trifluoromethyl)phenyl)-1,3,4-oxadiazol-2-yl)thio)butanoic acid |
| A3 | 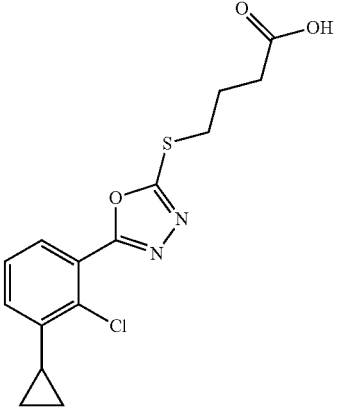<br>4-((5-(2-chloro-3-cyclopropylphenyl)-1,3,4-oxadiazol-2-yl)thio)butanoic acid |
| A4 | 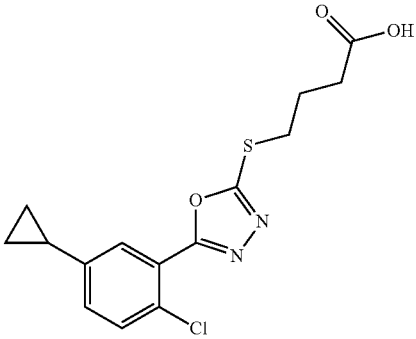<br>4-((5-(2-chloro-5-cyclopropylphenyl)-1,3,4-oxadiazol-2-yl)thio)butanoic acid |
| A5 | 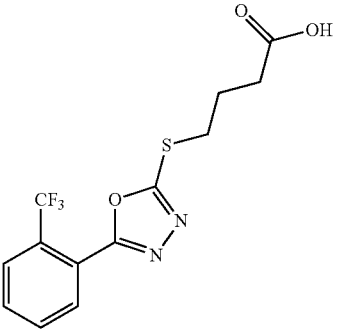<br>4-((5-(2-(trifluoromethyl)phenyl)-1,3,4-oxadiazol-2-yl)thio)butanoic acid |
| A6 | 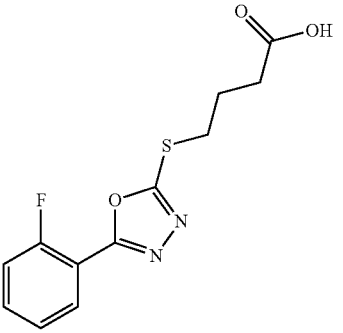<br>4-((5-(2-(fluorophenyl)-1,3,4-oxadiazol-2-yl)thio)butanoic acid |

TABLE A-continued

| Compound # | Structure/Name |
|---|---|
| A7 | 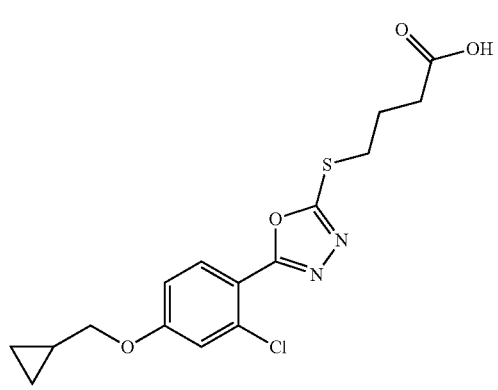
4-((5-(2-chloro-4-(cyclopropylmethoxy)phenyl)-1,3,4-oxadiazol-2-yl)thio)butanoic acid |
| A8 | 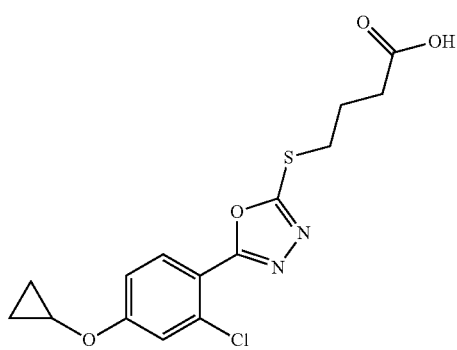
4-((5-(2-chloro-4-cyclopropoxyphenyl)-1,3,4-oxadiazol-2-yl)thio)butanoic acid |
| A9 | 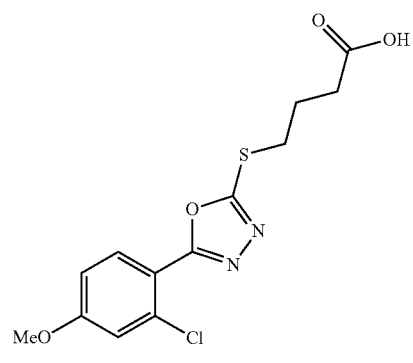
4-((5-(2-chloro-4-methoxyphenyl)-1,3,4-oxadiazol-2-yl)thio)butanoic acid |
| A10 | 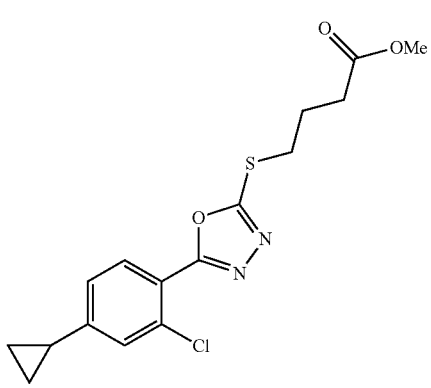
methyl 4-((5-(2-chloro-4-cyclopropylphenyl)-1,3,4-oxadiazol-2-yl)thio)butanoate |
| A11 | 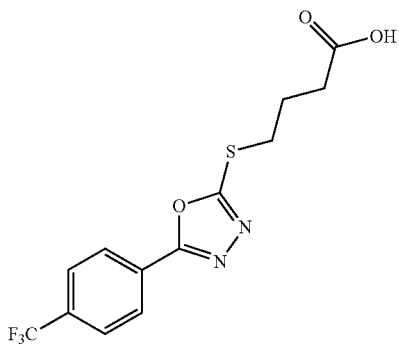
4-((5-(4-(trifluoromethyl)phenyl)-1,3,4-oxadiazol-2-yl)thio)butanoic acid |
| A12 | 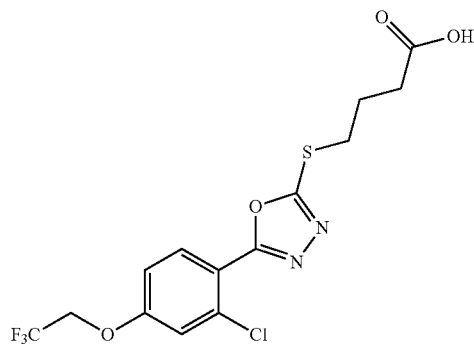
4-((5-(2-chloro-4-(2,2,2-trifluoroethoxy)phenyl)-1,3,4-oxadiazol-2-yl)thio)butanoic acid |

TABLE A-continued

| Compound # | Structure/Name |
|---|---|
| A13 | 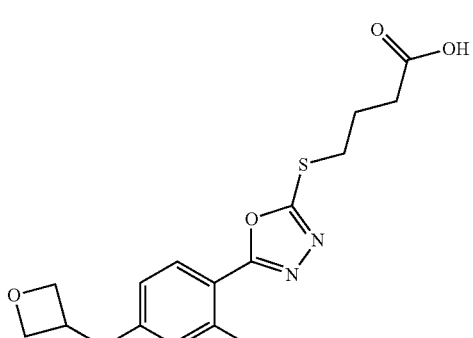<br>4-((5-(2-chloro-4-(oxetan-3-yloxy)phenyl)-1,3,4-oxadiazol-2-yl)thio)butanoic acid |
| A14 | 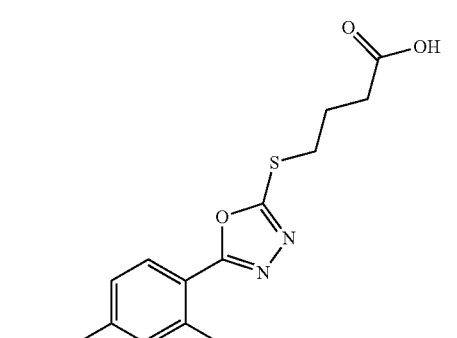<br>4-((5-(2-chloro-4-(trifluoromethoxy)phenyl)-1,3,4-oxadiazol-2-yl)thio)butanoic acid |
| A15 | 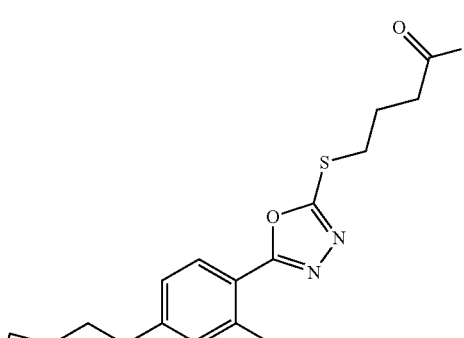<br>4-((5-(2-chloro-4-(oxetan-3-ylmethoxy)phenyl)-1,3,4-oxadiazol-2-yl)thio)butanoic acid |
| A16 | 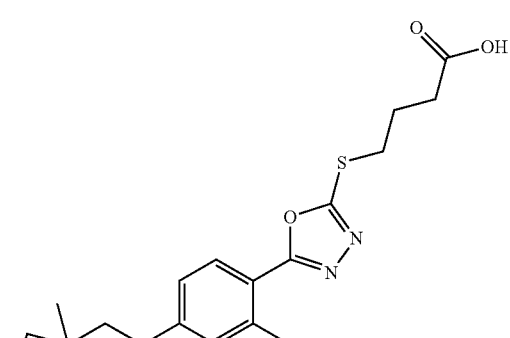<br>4-((5-(2-chloro-4-((3-methyloxetan-3-yl)methoxy)phenyl)-1,3,4-oxadiazol-2-yl)thio)butanoic acid |
| A17 | 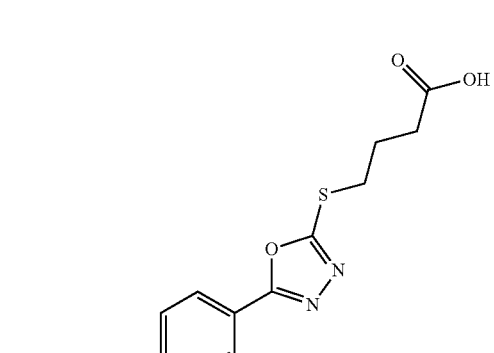<br>4-((5-(4-(2,2,2-trifluoroethoxy)phenyl)-1,3,4-oxadiazol-2-yl)thio)butanoic acid |
| A18 | 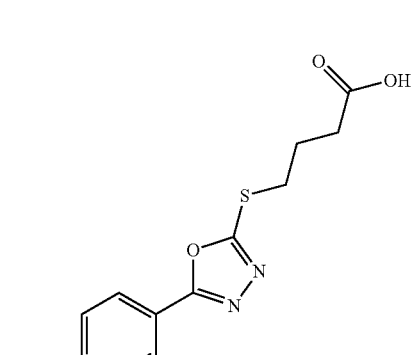<br>4-((5-(4-(difluoromethyl)phenyl)-1,3,4-oxadiazol-2-yl)thio)butanoic acid |

TABLE A-continued

| Compound # | Structure/Name |
|---|---|
| A19 | 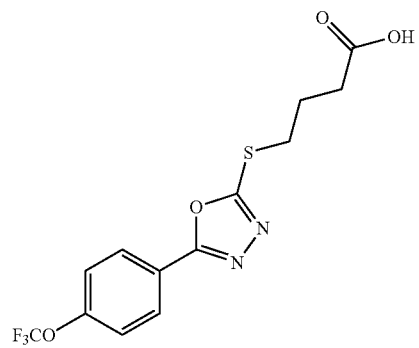 4-((5-(4-(trifluoromethoxy)phenyl)-1,3,4-oxadiazol-2-yl)thio)butanoic acid |
| A20 | 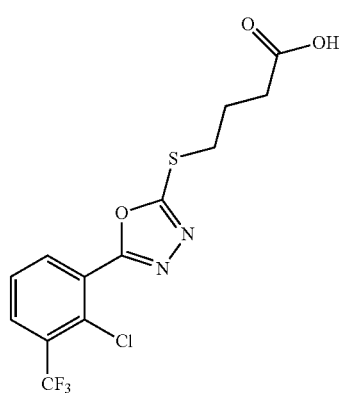 4-((5-(2-chloro-3-(trifluoromethyl)phenyl)-1,3,4-oxadiazol-2-yl)thio)butanoic acid |
| A21 | 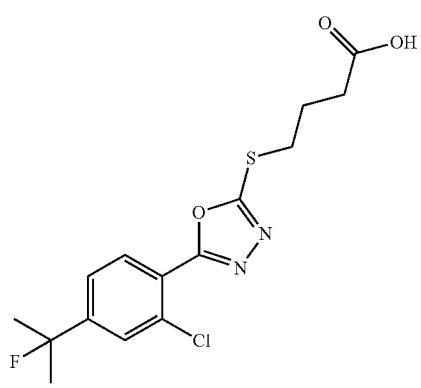 4-((5-(2-chloro-4-(2-fluoropropan-2-yl)phenyl)-1,3,4-oxadiazol-2-yl)thio)butanoic acid |
| A22 | 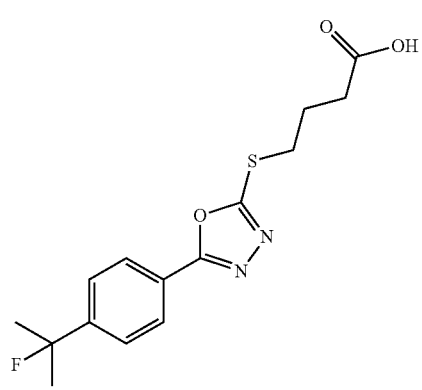 4-((5-(2-chloro-4-(2-fluoropropan-2-yl)phenyl)-1,3,4-oxadiazol-2-yl)thio)butanoic acid |
| A23 | 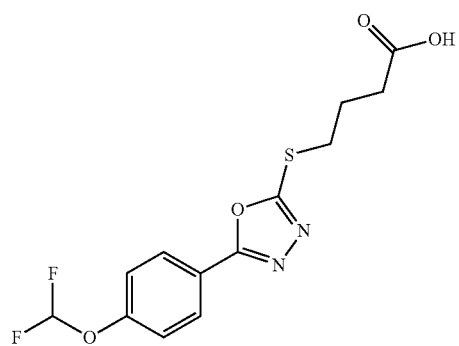 4-((5-(4-(difluoromethoxy)phenyl)-1,3,4-oxadiazol-2-yl)thio)butanoic acid |
| A24 | 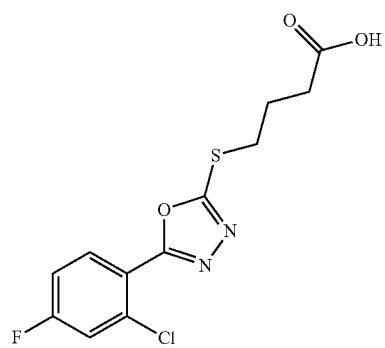 4-((5-(2-chloro-4-fluorophenyl)-1,3,4-oxadiazol-2-yl)thio)butanoic acid |

TABLE A-continued

| Compound # | Structure/Name |
|---|---|
| A25 | 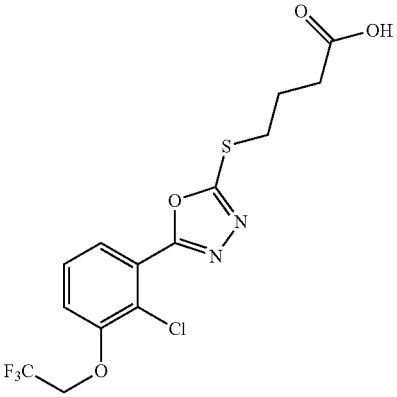<br>4-((5-(2-chloro-3-(2,2,2-trifluoroethoxy)phenyl)-1,3,4-oxadiazol-2-yl)thio)butanoic acid |
| A26 | 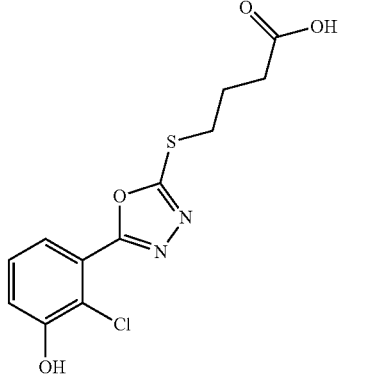<br>4-((5-(2-chloro-3-hydroxyphenyl)-1,3,4-oxadiazol-2-yl)thio)butanoic acid |
| A27 | 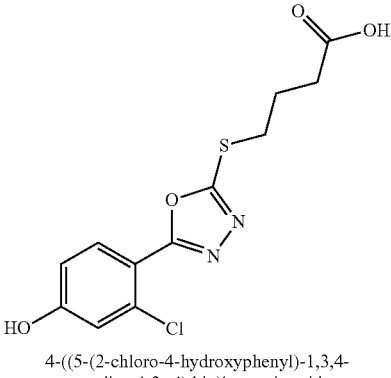<br>4-((5-(2-chloro-4-hydroxyphenyl)-1,3,4-oxadiazol-2-yl)thio)butanoic acid |

In some embodiments, X is $C_{3-6}$cycloalkylenyl, and $R^3$, $R^4$, and $R^5$ are each independently selected from the group consisting of H, halo, $C_{1-7}$alkyl, $OC_{1-7}$alkyl, $C_{3-7}$cycloalkyl, $OC_{3-7}$cycloalkyl, $C_{2-4}$heterocycloalkyl, and $OC_{2-4}$heterocycloalkyl, wherein one or two carbon atoms of the alkyl group can optionally be replaced with oxygen, and the heterocycloalkyl group comprises one oxygen ring atom. The $C_{1-7}$alkyl group can optionally be substituted with, e.g., with one or more fluorine atoms.

In some cases $R^2$ is not H and two of $R^3$, $R^4$, and $R^5$ are H. In some embodiments, the two ring substituents are trans. In various embodiments, the two ring substituents are cis.

In some cases, the $C_{3-6}$cycloalkylenyl is selected from the group consisting of cyclobutyl, cyclopentyl, and cyclohexyl. In various cases, the $C_{3-6}$cycloalkylenyl is cyclobutyl. In some embodiments, the $C_{3-6}$cycloalkylenyl is cyclopentyl. In various embodiments, the $C_{3-6}$cycloalkylenyl is cyclohexyl.

In some cases, $R^3$ is H. In some embodiments, $R^3$ is halo. In various embodiments, halo is Cl. In various cases, $R^3$ is $C_{1-7}$alkyl or $OC_{1-7}$alkyl, wherein one or two carbon atoms of the alkyl can optionally be replaced with oxygen. In some embodiments, $R^3$ is methyl, ethyl, propyl, isopropyl, n-butyl, isobutyl, s-butyl, or t-butyl. In various embodiments, $R^3$ is O-methyl, O-ethyl, O-propyl, O-isopropyl, O-n-butyl, O-isobutyl, O-s-butyl, or O-t-butyl. In some cases, $R^3$ is $C_{3-7}$cycloalkyl, $OC_{3-7}$cycloalkyl, $C_{2-4}$heterocycloalkyl, or $OC_{2-4}$heterocycloalkyl, wherein the heterocycloalkyl group comprises one oxygen ring atom. In some embodiments, $R^3$ comprises cyclopropyl, cyclobutyl, oxiranyl, or oxetanyl (e.g., oxetanyl or methyloxetanyl). In various embodiments, $R^3$ is cyclopropyl.

In some embodiments, $R^4$ is H. In various embodiments, $R^4$ is halo. In some cases, $R^4$ is Cl. In various cases, $R^4$ is $C_{1-7}$alkyl (optionally substituted with fluorine atoms to form $C_{1-7}$fluoroalkyl) or $OC_{1-7}$alkyl, wherein one or two carbon atoms of the alkyl can optionally be replaced with oxygen. In some embodiments, $R^4$ is $CHF_2$, $CF_3$, $CH_2CF_3$, or $CF(CH_3)_2$. In some cases, $R^4$ is $CF_3$. In some embodiments, $R^4$ is $C_{3-7}$cycloalkyl, $OC_{3-7}$cycloalkyl, $C_{2-4}$heterocycloalkyl, or $OC_{2-4}$heterocycloalkyl, wherein the heterocycloalkyl group comprises one oxygen ring atom. In some cases, $R^4$ comprises cyclopropyl, cyclobutyl, oxiranyl, or oxetanyl (e.g., oxetanyl or methyloxetanyl). In some cases, $R^4$ is selected from the group consisting of Cl, $CF_3$, and cyclopropyl.

In various embodiments, $R^5$ is H. In some cases, $R^5$ is $C_{1-5}$alkyl or $OC_{1-5}$alkyl optionally substituted with one or more fluorine atoms. In some cases, $R^5$ is $C_{1-5}$fluoroalkyl or $OC_{1-5}$fluoroalkyl. In various cases, $R^5$ is $CH_2F$, $CHF_2$, $CF_3$, $CF(CH_3)_2$, $CH_2CF_3$, $OCH_2F$, $OCHF_2$, $OCF_3$, $OCF(CH_3)_2$, and $OCH_2CF_3$. In some embodiments, $R^5$ is $C_{0-3}$alkylene-$C_{3-5}$cycloalkyl, $OC_{0-3}$alkylene-$C_{3-5}$cycloalkyl, $C_{0-3}$alkylene-$C_{2-4}$heterocycloalkyl, or $OC_{0-3}$alkylene-$C_{2-4}$heterocycloalkyl, wherein the cycloalkyl and heterocycloalkyl are each optionally substituted with one or more fluorine atoms, and the heterocycloalkyl comprises one oxygen ring atom. In various cases, $R^5$ comprises cyclopropyl or oxetanyl. In some embodiments, $R^5$ is selected from the group consisting of

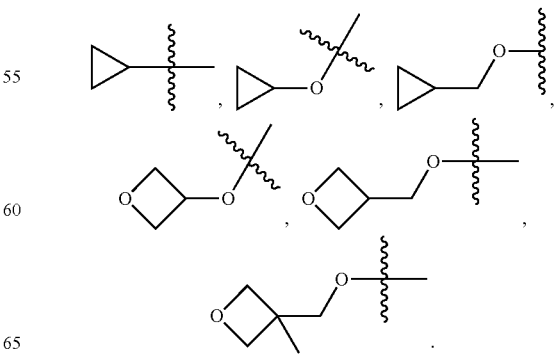

and

In some embodiments, disclosed herein is a compound listed in Table B or a pharmaceutically acceptable salt thereof (e.g., B1-B10). In various cases, the compound of Formula (I) is selected from the group consisting of B2, B3, B5, and B7.

TABLE B

| Compound # | Structure/Name |
|---|---|
| B1 | trans-3-((5-(2,4-dichlorophenyl)-1,3,4-oxadiazol-2-yl)thio)cyclobutanecarboxylic acid |
| B2 | cis-3-((5-(2,4-dichlorophenyl)-1,3,4-oxadiazol-2-yl)thio)cyclobutanecarboxylic acid |
| B3 | cis-3-((5-(2-chloro-4-cyclopropylphenyl)-1,3,4-oxadiazol-2-yl)thio)cyclobutanecarboxylic acid |

TABLE B-continued

| Compound # | Structure/Name |
|---|---|
| B4 | trans-3-((5-(2-chloro-4-cyclopropylphenyl)-1,3,4-oxadiazol-2-yl)thio)cyclobutanecarboxylic acid |
| B5 | cis-3-((5-(2-chloro-4-(trifluoromethyl)phenyl)-1,3,4-oxadiazol-2-yl)thio)cyclobutanecarboxylic acid |
| B6 | trans-3-((5-(2-chloro-4-(trifluoromethyl)phenyl)-1,3,4-oxadiazol-2-yl)thio)cyclobutanecarboxylic acid |
| B7 | cis-3-((5-(2,4-dichlorophenyl)-1,3,4-oxadiazol-2-yl)thio)cyclopentanecarboxylic acid |

TABLE B-continued

| Compound # | Structure/Name |
|---|---|
| B8 | 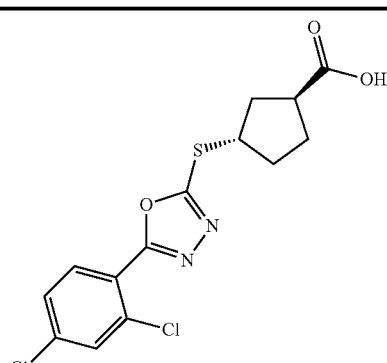<br>trans-3-((5-(2,4-dichlorophenyl)-1,3,4-oxadiazol-2-yl)thio)cyclopentanecarboxylic acid |
| B9 | 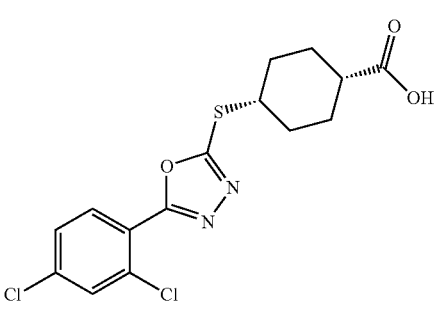<br>cis-4-((5-(2,4-dichlorophenyl)-1,3,4-oxadiazol-2-yl)thio)cyclohexanecarboxylic acid |
| B10 | 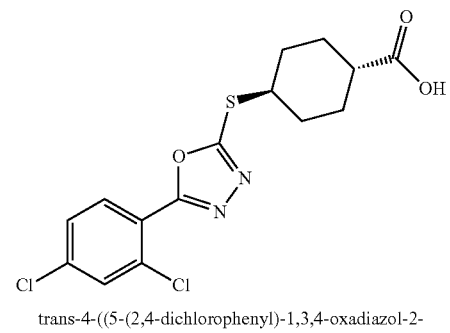<br>trans-4-((5-(2,4-dichlorophenyl)-1,3,4-oxadiazol-2-yl)thio)cyclohexanecarboxylic acid |

Synthesis of Inhibitors of Rho/MRTF/SRF-Mediated Gene Transcription

The inhibitors described herein can be synthesized by any method known to one skilled in the art.

Compounds having a propylene group for X and comprising alkyl or cycloalkyl for $R^3$ and/or $R^4$ can be prepared by protecting the carboxylic acid (e.g., with MeOH, $H_2SO_4$) of a benzoic acid group having bromo at $R^3$ and/or $R^4$ to form a methyl ester, and then reacting the bromo group with a desired boron compound using a palladium-catalyzed Suzuki cross-coupling reaction. The thiol-substituted oxadizole can be formed by reacting the methyl ester with hydrazine and carbon disulfide in two steps. Finally, the butanoic acid group can be installed by reacting the thiol with 4-bromobutanoic acid and deprotecting the terminal methyl ester. For example, A1 can be prepared according to Scheme 1, below.

Scheme 1

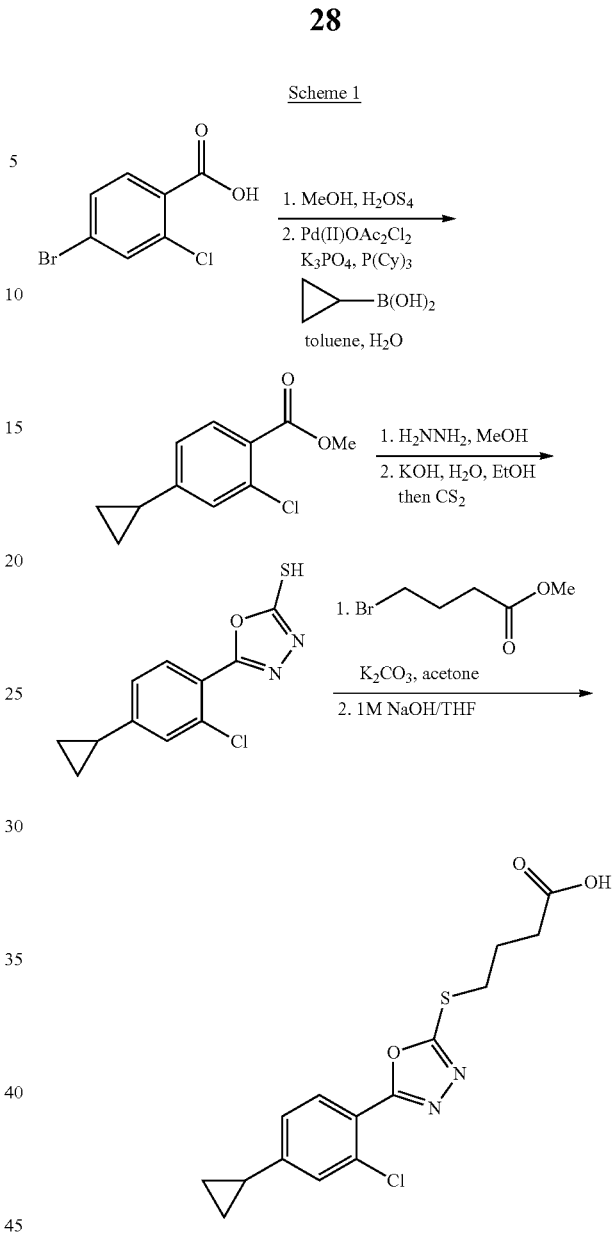

In some embodiments where the aryl group has a hydroxyl substituent, the hydroxyl group can be benzyl-protected before the synthesis of the thiol-substituted oxadiazole, as shown for Compound C in Scheme 2, below.

Scheme 2

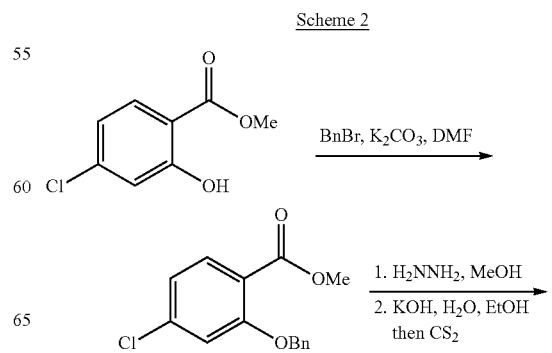

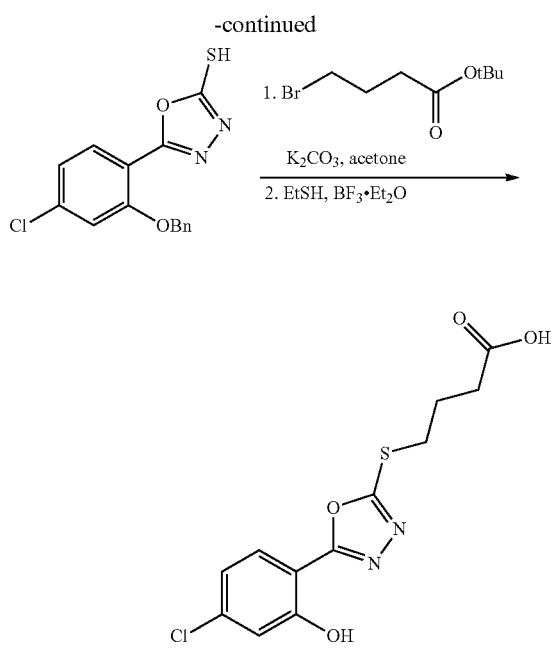

Compounds having a propylene group for X and comprising Oalkyl or Ocycloalkyl for R³ and/or R⁴ can be prepared by protecting the aryl alcohol of a desired methylhydroxybenzoate with 2-propynyl benzesulfonate to form a propynyloxybenzoate, forming the thiol-substituted oxadizole butanoate as previously described, deprotecting the propynyl-substituted alcohol, and then reacting the resulting alcohol with a desired bromo-substituted alkyl or cycloalkyl group, as shown for A7 in Scheme 3, below.

Scheme 3

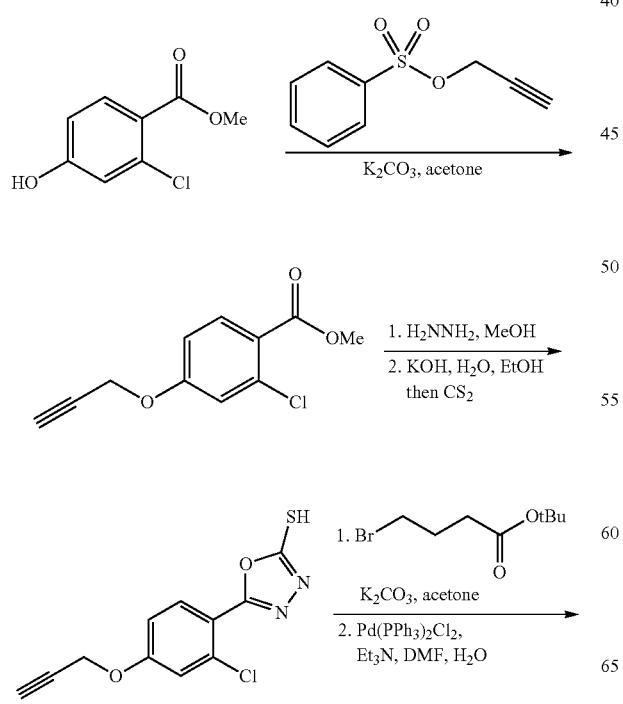

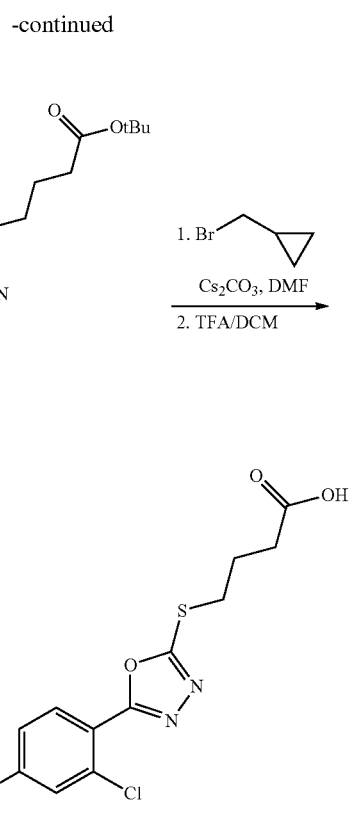

Compounds having a cycloalkylene group for X can be prepared by reacting a desired thiol-substituted oxadiazole with either a cholo- or a methylsulfonyloxy-cycloalkylene-methylester. For example, B1 and B2 can be prepared according to Scheme 4, below, and B7 and B8 can be prepared according to Scheme 5, below Scheme 4

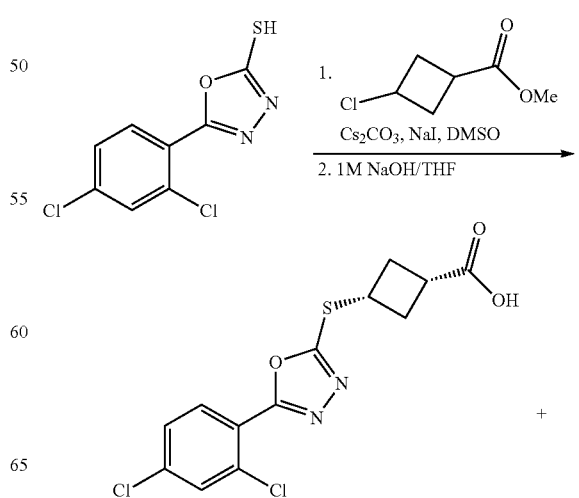

+

-continued

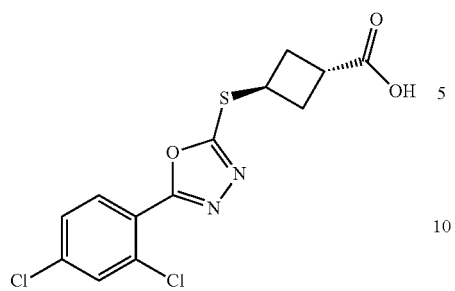

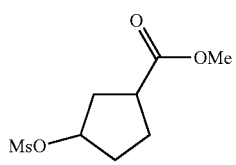

Various starting material methylbenzoates can be formed by methods known to those skilled in the art. For example, see Schemes 7-11, below, for the synthesis of methylbenzoate groups having the following $R^4$ groups: $CF(CH_3)_2$, $OCF_3$, Ocyclopropyl, $OCH_2CH_3$, and $OCH_2$oxetanyl.

Scheme 5

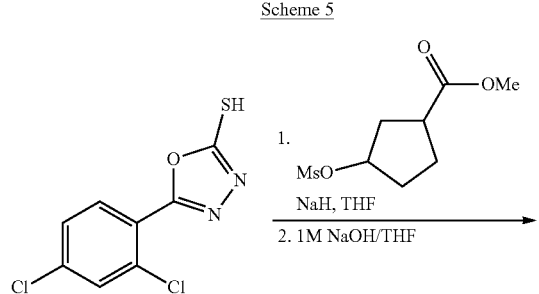

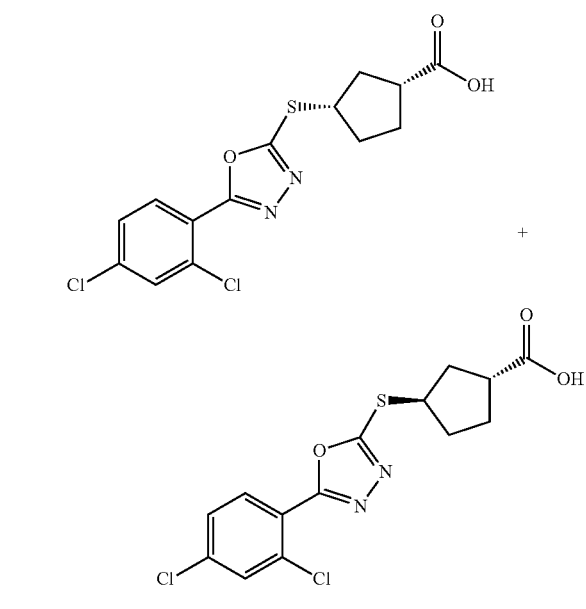

The methylsulfonyloxy-cycloalkylene-methylester compound from Scheme 5 can be prepared by reducing a desired 3-oxocycloalkyene-1-methylester and protecting the resulting alcohol with a methanesulfonyl group, as shown in Scheme 6, below.

Scheme 7

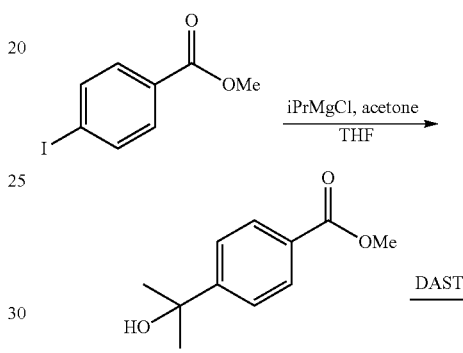

Scheme 8

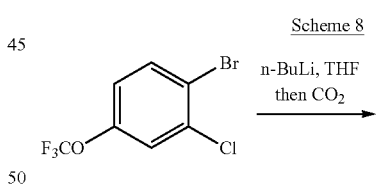

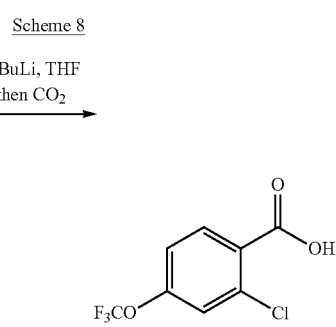

Scheme 6

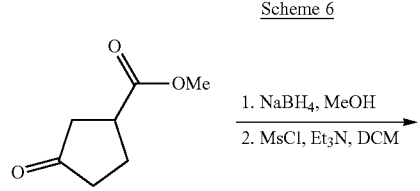

Scheme 9

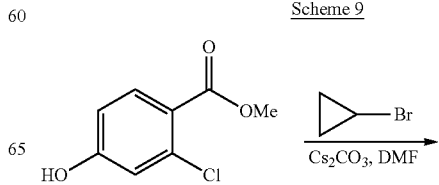

-continued

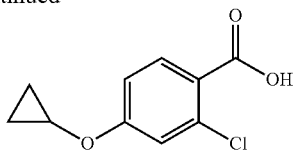

Scheme 10

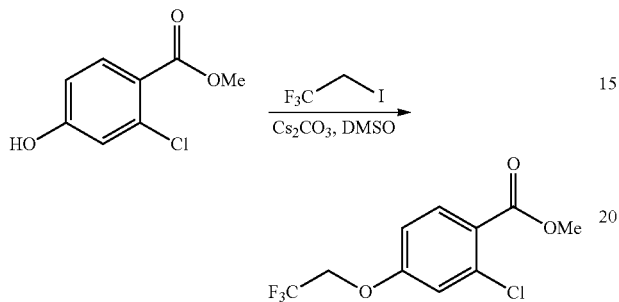

Scheme 11

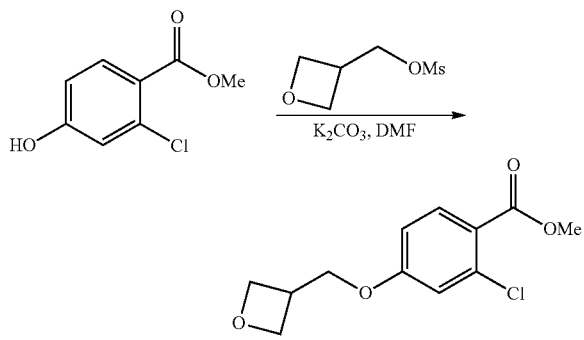

Additional synthetic procedures for preparing the inhibitors disclosed herein can be found in the Examples section.

Methods

The compounds disclosed herein can inhibit Rho/MRTF/SRF-mediated gene transcription, which is useful in preventing or treating diseases related to a dysfunction in Rho/MRTF/SRF-mediated gene transcription.

The rho family of GTPases regulates many aspects of intracellular actin dynamics. Rho signaling causes MRTF to translocate to the cell nucleus and bind to SRF. The binding of MRTF to SRF leads to expression of c-fos, which along with c-jun, forms the transcription factor AP-1. The AP-1 transcription factor promotes the activity of various matrix metalloproteinases ("MMPs") and other cell motility genes, the overexpression of which leads to cancer cell invasion and metastasis. Thus, dysfunction of Rho/MRTF/SRF-mediated gene transcription has been implicated in cancer metastasis.

Dysfunction of Rho/MRTF/SRF-mediated gene transcription also has been implicated in fibrosis. The hallmark of fibrotic disease is the transition of normal fibroblasts into myofibroblasts, which are characterized by the expression of alpha smooth muscle actin ("α-SMA") and the production of extracellular matrix ("ECM"). Fibroblast activation to myofibroblasts results from gene transcription stimulated by a common Rho-mediated signaling pathway that originates from divergent extracellular profibrotic stimuli. Specifically, rho mediates the conversion of G-actin to F-actin, which releases G-actin-bound MRTF. The release of G-actin-bound MRTF results in accumulation of MRTF in the nucleus, where it binds to SRF on the serum response element ("SRE") promoter. Thus, MRTF serves as a regulator of the fibrotic process used in wound healing, and dysregulation and/or overstimulation of it can lead to fibrosis.

As such, further provided are methods of treating or preventing a disease related to dysfunction of Rho/MRTF/SRF-mediated gene transcription using a compound as disclosed herein, such as a compound of Formula (I), a compound listed in Table A (e.g., A1-A27), a compound listed in Table B (e.g., B1-B10),

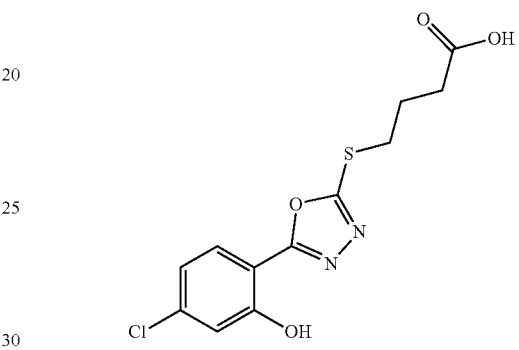

(4-((5-(4-chloro-2-hydroxyphenyl)-1,3,4-oxadiazol-2-yl) thio)butanoic acid ("Compound C"), or a pharmaceutically acceptable salt of the foregoing.

Thus, one aspect of the disclosure relates to a method of inhibiting Rho/MRTF/SRF-mediated gene transcription in a cell, comprising contacting the cell with a compound disclosed herein in an amount effective to inhibit gene transcription. For example, Rho/MRTF/SRF-mediated gene transcription can be inhibited in a cell by contacting the cell with a compound disclosed herein, such as a compound of Formula (I), a compound listed in Table A (e.g., A1-A27), a compound listed in Table B (e.g., B1-B10), Compound C, or a pharmaceutically acceptable salt of the foregoing. The contacting of the cell can occur in vitro or in vivo. In some cases, contacting of the cell occurs in vitro. In other cases, contacting of the cell occurs in vivo. A compound disclosed herein, such as a compound of Formula (I), a compound listed in Table A (e.g., A1-A27), a compound listed in Table B (e.g., B1-B10), Compound C, or a pharmaceutically acceptable salt of the foregoing, can contact a cell in vivo by administering the compound to a subject in need of inhibition of Rho/MRTF/SRF-mediated gene transcription. Therefore, the disclosure includes administering one or more of the compounds disclosed herein, such as a compound of Formula (I), a compound listed in Table A (e.g., A1-A27), a compound listed in Table B (e.g., B1-B10), Compound C, or a pharmaceutically acceptable salt of the foregoing, to a subject, such as a human, in need thereof. In some embodiments, the subject suffers from a disease associated with dysfunction of Rho/MRTF/SRF-mediated gene transcription (e.g., cancer, fibrotic disease, diabetes, insulin sensitivity, hyperactive platelets, metabolic disease, inflammation, inflammatory disease, pulmonary arterial hypertension, axon regeneration following nerve damage, Raynaud's phenomenon, cerebral vascular disease, cardiovascular disease, erectile dysfunction, and combinations thereof).

In various cases, the subject suffers from a cancer. In some embodiments, the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, glioblastoma, leukemia, megakaryoblastic leukemia, polycythemia vera, lymphoma, multiple myeloma, Waldenstrom's macroglobulinemia, heavy chain disease, and combinations thereof. In some cases, the subject suffers from a cancer selected from the group consisting of megakaryoblastic leukemia, melanoma, breast cancer, prostate cancer, glioblastoma, and combinations thereof. In some embodiments, the melanoma is cutaneous or uveal.

In some cases, the subject suffers from a fibrotic disorder. In some cases, the fibrotic disease is systemic sclerosis, pulmonary fibrosis, cardiac fibrosis, liver fibrosis, liver cirrhosis, renal fibrosis, chronic renal failure, diabetic nephropathy, lung fibrosis, nephrogenic systemic fibrosis, graft versus host disease, Dupuytren's contracture, inflammatory bowel disease, Crohn's disease, ocular fibrosis, glaucoma, post-trabeculectomy fibrosis, corneal fibrosis, pterygia, Graves opthmalopathy, diabetic retinopathy, age-related macular degeneration, postoperative adhesions, reactive fibrosis, chronic heart failure, or combinations thereof. In some cases, the subject suffers from systemic sclerosis or idiopathic pulmonary fibrosis.

In some embodiments, the subject suffers from a metabolic disease. In some cases, the metabolic disease is obesity, diabetes, insulin resistance, or combinations thereof. In some cases, the metabolic disease is diabetes, such as type II diabetes.

Use of a compound disclosed herein, such as a compound of Formula (I), a compound listed in Table A (e.g., A1-A27), a compound listed in Table B (e.g., B1-B10), Compound C, or a pharmaceutically acceptable salt of the foregoing, to treat a condition resulting from dysfunction of Rho/MRTF/SRF-mediated gene transcription in a subject, as well as use of the compound in the preparation of a medicament for treating the condition, also are contemplated.

Further guidance for using compounds disclosed herein for inhibiting Rho/MRTF/SRF-mediated gene transcription, such as a compound of Formula (I), a compound listed in Table A (e.g., A1-A27), a compound listed in Table B (e.g., B1-B10), Compound C, or a pharmaceutically acceptable salt of the foregoing, can be found in the Examples section, below.

Pharmaceutical Formulations, Dosing, and Routes of Administration

Also provided herein are pharmaceutical formulations that include a compound of Formula (I), as previously described herein, a compound listed in Table A (e.g., A1-A27), a compound listed in Table B (e.g., B1-B10), or a pharmaceutically acceptable salt of the foregoing, and one or more pharmaceutically acceptable excipients.

The inhibitors described herein can be administered to a subject in a therapeutically effective amount. A inhibitor can be administered alone or as part of a pharmaceutically acceptable composition or formulation. In addition, an inhibitor can be administered all at once, multiple times, or delivered substantially uniformly over a period of time. It is also noted that the dose of the compound can be varied over time.

An inhibitor disclosed herein can be administered in combination with one or more additional pharmaceutically active compounds/agents. The additional pharmaceutically active compounds/agents may be small molecules or can be macromolecules such as a proteins, antibodies, peptibodies, DNA, RNA or fragments of such macromolecules.

An inhibitor disclosed herein and other pharmaceutically active compounds, if desired, can be administered to a patient or subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. enteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

An inhibitor described herein can be administered to a patient or subject at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the patient or subject, the severity of the condition or disease being treated, and the pharmacological activity of the compound being administered. The determination of dosage ranges and optimal dosages for a particular patient or subject is within the ordinary skill in the art.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Kits

Also provided herein are kits that include a pharmaceutical formulation comprising a compound of Formula (I), as previously described herein, a compound listed in Table A (e.g., A1-A27), a compound listed in Table B (e.g., B1-B10), or pharmaceutically acceptable salts of the foregoing, and instructions for administering the pharmaceutical formulation to a patient. In some embodiments the kit is provided with a device for administering the formulation to a patient. The kit may further include a variety of containers, e.g., vials, tubes, bottles, and the like. In some cases, the device of the kit is an aerosol dispensing device, wherein the formulation is prepackaged within the aerosol device. In various embodiments, the kit comprises a syringe and a needle, wherein the formulation is optionally prepackaged within the syringe.

EXAMPLES

The following examples are provided for illustration and are not intended to limit the scope of the invention.

All reagents were received from commercial sources unless otherwise noted. $^1H$ and $^{13}C$ spectra were obtained in DMSO-$d_6$, MeOD-$d_4$, or CDCl$_3$ at RT, unless otherwise noted, on Varian Inova 400 MHz or Varian Inova 500 MHz. Chemical shifts for the $^1H$ and $^{13}C$ spectra were recorded in parts per million (ppm) on the b scale from an internal standard of residual tetramethylsilane (0 ppm). Mass spectroscopy data were obtained on a Waters Corporation LCT. Purity of tested compounds was assessed by HPLC using an Agilent 1100 Series with an Agilent Zorbax Eclipse Plus-C18 column (254 nm detection) with the gradient: 10% ACN/water (1 min), 10-90% ACN (6 min), and 90% ACN/water (2 min). HPLC retention times (Ret) were recorded in minutes (min).

SRE.L-Luciferase Reporter Assay

Biological activity of the compounds disclosed herein were assessed in the SRE.L luciferase reporter assay. HEK-293T cells were co-transfected with 2 ng of the Gα12Q231L expression plasmid along with 50 ng of the SRE.L and 7 ng of the pRL-TK luciferase reporter plasmids, as described in the Materials and Methods section. Cells were treated with 0 (vehicle, DMSO alone), 1, 3, 10, 30, and 100 μM of a compound disclosed herein for 19 hrs after transfection before lysis. Luminescence was determined as described in the Materials and Methods section. Just before cell lysis, the viability of the cells was measured using the WST-1 cell proliferation reagent as described in the Materials and Methods section. Data are expressed as percentage of inhibition (DMSO alone=0%). The experiments were performed three separate times to achieve n=3 in triplicate.

Results of SRE.L-Luciferase assay are shown in the Tables C, D, and E, below.

TABLE C

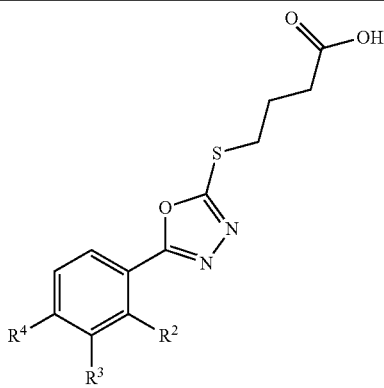

| Compound No. | $R^2$ | $R^3$ | $R^4$ | $IC_{50}$ (nM) |
|---|---|---|---|---|
| CCG-232120 | Cl | H | Cl | 1.8 |
| A11 | H | H | $CF_3$ | 46 |
| A18 | H | H | difluoromethyl | 160 |
| A5 | $CF_3$ | H | H | 6,200 |
| A24 | Cl | H | F | NT |
| A6 | F | H | H | 211 |
| A2 | Cl | H | $CF_3$ | 0.06 |
| A20 | Cl | $CF_3$ | H | 330 |
| A22 | H | H | 1-fluoroisopropyl | 9.5 |
| A21 | Cl | H | 1-fluoroisopropyl | 0.5 |
| A19 | H | H | $OCF_3$ | 78 |
| A23 | H | H | difluoromethoxy | 130 |
| A17 | H | H | 1,1,1-trifluoroethoxy | 240 |
| A14 | Cl | H | $OCF_3$ | 3.6 |
| A12 | Cl | H | 1,1,1-trifluoroethoxy | 0.8 |
| A25 | Cl | 1,1,1-trifluoroethoxy | H | NT |
| Compound C | OH | H | Cl | 0.02 |
| A26 | Cl | OH | H | NT |
| A27 | Cl | H | OH | NT |

TABLE D

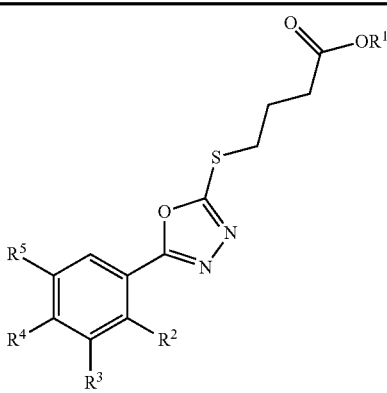

| Compound No. | $R^1$ | $R^2$ | $R^3$ | $R^4$ | $R^5$ | $IC_{50}$ (nM) |
|---|---|---|---|---|---|---|
| A1 | H | Cl | H | cyclopropyl | H | 0.0012 |
| A10 | Me | Cl | H | cyclopropyl | H | 3 |
| A3 | H | Cl | cyclopropyl | H | H | 0.019 |
| A4 | H | Cl | H | H | cyclopropyl | 11 |
| A8 | H | Cl | H | cyclopropoxy | H | 1.3 |
| A7 | H | Cl | H | cyclopropylmethoxy | H | 0.02 |
| A13 | H | Cl | H | oxetanyl | H | 370 |
| A15 | H | Cl | H | oxetanylmethyl | H | 35 |
| A16 | H | Cl | H | 1-methyl oxetanylmethyl | H | 42 |

TABLE E

| Compound No. | $R^4$ | n | stereochemisty | $IC_{50}$ (nM) |
|---|---|---|---|---|
| B2 | Cl | 1 | cis | 4.9 |
| B1 | Cl | 1 | trans | 140 |
| B7 | Cl | 2 | cis | 15 |
| B8 | Cl | 2 | trans | >100,000 |
| B9 | Cl | 3 | cis | >100,000 |
| B10 | Cl | 3 | trans | >100,000 |
| B3 | Cyclopropyl | 1 | cis | 0.46 |
| B4 | Cyclopropyl | 1 | trans | 2.6 |
| B5 | $CF_3$ | 1 | cis | 42 |
| B6 | $CF_3$ | 1 | trans | 1000 |

Compounds (1 µM) were incubated with MLM in the presence of beta-NADPH (1 mM) for 60 min. The remaining drug concentration was measured using LC-MS using multiple reaction monitoring (MRM) mode. Both initial and overall disappearance rate and half-lives were calculated. It has been found that a half-life of 5 min in this MLM assay corresponds to about 2 hrs in vivo in mice. Verapamil was run as a positive control in every assay; its half-life could not exceed 4 min or the assay was considered invalid. Results are reported as half-lives in minutes (min) and are summarized in Table F below.

TABLE F

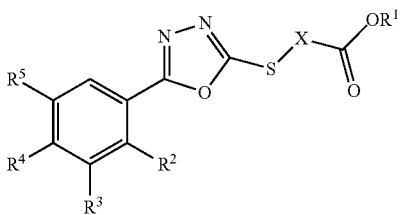

| Compound No. | MLM T$_{1/2}$ (min) | X | R$^1$ | R$^2$ | R$^3$ | R$^4$ | R$^5$ |
|---|---|---|---|---|---|---|---|
| CCG-232922 | 28 | propylene | H | Cl | H | CH$_3$ | H |
| A1 | 47 | propylene | H | Cl | H | cyclopropyl | H |
| A2 | >60 | propylene | H | Cl | H | CF$_3$ | H |
| B2 | >60 | cyclobutylene | H | Cl | H | Cl | H |
| CCG-262687 | 19 | propylene | H | Cl | H | OCH$_2$CH$_3$ | H |
| A8 | >60 | propylene | H | Cl | H | O-cyclopropyl | H |
| A12 | >60 | propylene | H | Cl | H | O-oxetanyl | H |

The compounds can exhibit desired potency and metabolic stability when X is a propylene group and at least one of R$^3$, R$^4$, and R$^5$ comprises a fluoroalkyl, Ofluoroalkyl, cycloalkyl, or single O-containing heterocycloalkyl group. For example, bulkier alkyl R$^3$, R$^4$, and R$^5$ moieties (e.g. CCG-232120 vs. A1) generally improve activity, and cycloalkyl (e.g. CCG-232922 vs. A1 and CCG-262687 vs A8) and fluoroalkyl (e.g. CCG-232922 vs. A2) R$^3$, R$^4$, and R$^5$ moieties generally improve metabolic stability. Without being bound by any particular theory, bulkier alkyl R$^3$, R$^4$, and R$^5$ groups likely provide a better fit when bound to the biological target, while cycloalkyl and fluoroalkyl R$^3$, R$^4$, and R$^5$ groups provide protection from metabolic oxidation by CYPs. Also, when X is cycloalkylenyl (e.g. CCG-232120 in Table C vs. B2 and A1 vs B3), the activity decreases slightly (perhaps as a result of a poorer fit in the active site of the biological target) but the metabolic stability improves significantly (e.g. A1 vs B2 in Table F), likely resulting from superior stability of the ring carbons to oxidative metabolism compared to the propylene metabolic hot spot.

In Vivo Testing for Antifibrotic Effects

C57BL/6J mice were ordered from Jackson labs for delivery at 15-16 weeks of age. Mice were preconditioned with supplemental chow for two weeks prior to start of experiment. Mice were randomized by weight into four groups (vehicle, A1 (3 mg/kg), A1 (10 mg/kg), PBS). Each group consisted of two cages with four mice per cage. Drug stock solutions were aliquoted and stored at 4° C. for the duration of the study. Aliquots were warmed to 37° C. and briefly vortexed prior to filling the gavage syringes. Vehicle and A1 groups received daily bleomycin injections (0.1 mL, ID) each afternoon in a defined area of shaved dorsal skin. PBS control group received daily injections (0.1 mL, ID) of PBS in the afternoon. Mice were anesthetized with ketamine/xylazine for ID injections. A1 (3 or 10 mg/kg) and the vehicle (20% DMSO/50% PEG-400/30% PBS) were administered (PO) in the morning by the University of Michigan's Unit for Laboratory Animal Medicine In-Vivo Animal Core. Mice were weighed daily to determine gavage dosage volume. Mice were euthanized after fourteen days of treatment by CO$_2$ inhalation/thoracotomy. Skin from the defined area was excised for biochemical and histological analysis. A portion of the skin was fixed in neutral buffered formalin (10%), washed in 70% ethanol, and paraffin embedded for Masson's trichrome histological staining. Another portion of the skin was snap frozen for hydroxyproline measurement.

Figure 2:
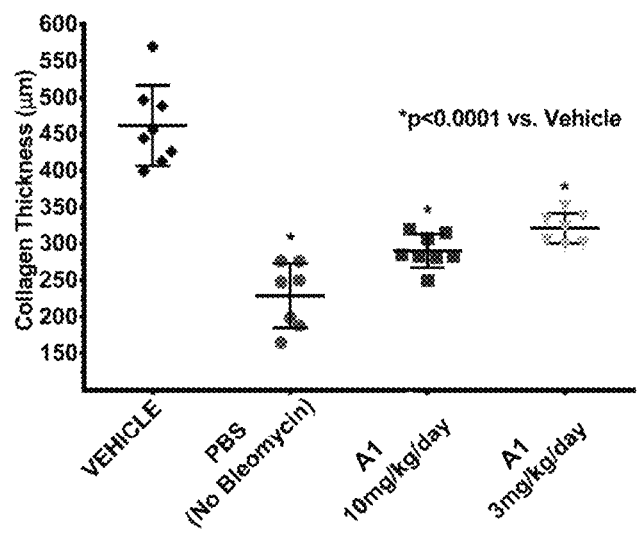
FIG. 2 depicts the reduction in collagen thickness in mice treated with compound A1, as further described in the Examples section.

Fixed skin was paraffin embedded and sectioned at the University of Michigan Comprehensive Cancer Center Histology Core. Skin sections were stained with Masson's trichrome (Sigma-Aldrich). Stained sections were analyzed with an Olympus BX51\DP72 microscope. Dermal thickness was determined by measuring the maximal distance between the epidermal-dermal junction and the dermal-subcutaneous fat junction. Three measurements were averaged from each skin section. The measurement was performed using the measurement tool in the cellSens imaging software package (Olympus). Results are summarized in FIG. 2.

Skin sections were weighed and hydrolyzed in 6M HCl at 120° C. for three hours. Hydrolyzed skin supernatant and hydroxyproline standards (Sigma-Aldrich) were transferred to a microplate and dried at 60° C. Samples and standards were oxidized with Chloramine T oxidation buffer for 5 minutes at room temperature. 4-(Dimethylamino) benzaldehyde was added to the wells and incubated at 60° C. until the standard was well defined. Absorbance was measured at 560 nm using a Synergy HT microplate reader (BioTek Instruments). Hydroxyproline values were normalized to tissue weight. Results are summarized in FIG. 1.

Preparation 1: 2-chloro-4-(trifluoromethoxy)benzoic acid

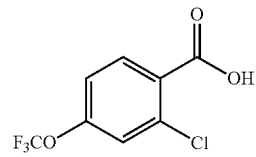

1-bromo-2-chloro-4-(trifluoromethoxy)benzene (0.25 g, 0.91 mmol) was added to an flame dried 50 mL round-bottomed flask charged with a stir bar containing tetrahydrofuran (4.0 mL). The solution was placed under Ar$_2$, cooled to −78° C. and n-butyllithium in hexanes (1.1 M, 0.83 mL) was added dropwise. The reaction proceeded for 5 min at −78° C. and then was quickly poured over dry ice. The solvents were evaporated in vacuo and the subsequent oil was partitioned between H$_2$O and hexanes. The aqueous was washed with hexanes (3×10 mL) and then the aqueous was acidified with 1N HCl (10 mL). The product was extracted with EtOAc (3×20 mL), washed with brine (3×10 mL), dried over MgSO$_4$, and concentrated in vacuo. $^1$H NMR (500 MHz, CDCl$_3$-d) δ ppm 8.11 (d, J=8.7 Hz, 1H) 7.39 (d, J=1.7 Hz, 1H) 7.22 (dd, J=8.8, 1.7 Hz, 1H); HPLC Ret: 6.65 min.

Preparation 2: 2-Chloro-4-cyclopropoxybenzoic acid

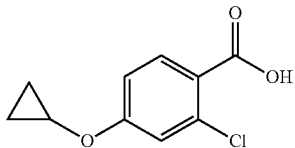 [SMILES: O=C(O)c1ccc(OC2CC2)cc1Cl]

Methyl 2-chloro-4-hydroxybenzoate (0.25 g, 1.34 mmol) was dissolved in 2.0 mL DMA. Bromocyclopropane (0.54 g, 4.42 mmol) along with Cs$_2$CO$_3$ (1.4 g, 4.42 mmol) were added and the reaction was stirred at 155° C. for 24 hr. The reaction was diluted with 10 mL H$_2$O and washed with EtOAc (3×10 mL). The aqueous layer was acidified to pH 1 with 1N HCl and the product was extracted with EtOAc (3×15 mL). The organic layers were combined, washed with brine (3×10 mL), dried with MgSO$_4$, and evaporated in vacuo. The subsequent oil was subjected to silica gel chromatography eluting with 45% EtOAc: 55% Hex: 0.1% AcOH. The fractions containing product were concentrated in vacuo. $^1$H NMR (500 MHz, DMSO-d$_6$) δ ppm 13.00 (br. s, 1H) 7.84 (d, 8.7 Hz, 1H) 7.20 (d, J=2.5 Hz, 1H) 6.99 (dd, J=8.8, 2.5 Hz, 1H) 3.98 (tt, J=6.1, 2.9 Hz, 1H) 0.87-0.79 (m, 2H) 0.70 (tdd, J=5.9, 3.0, 1.5, 2H); TOF ES$^+$ MS: (M+H) 213.03; HPLC Ret: 6.33 min.

Preparation 3: Methyl 4-bromo-2-chlorobenzoate

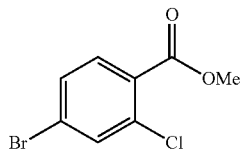 [SMILES: COC(=O)c1ccc(Br)cc1Cl]

4-bromo-2-chlorobenzoic acid (1.0 g, 4.25 mmol) was dissolved in 20 mL MeOH. Sulfuric acid (0.54 g, 0.3 mL, 5.52 mmol) was added dropwise and the reaction mixture was stirred at reflux (85° C.) for 16 hr. MeOH was removed in vacuo and the residue was diluted in 15 mL H$_2$O. The reaction was quenched with K$_2$CO$_3$ (pH 5-6), and the product was extracted with DCM (3×10 mL), washed with brine (3×10 mL), dried with MgSO$_4$, and concentrated in vacuo. $^1$H NMR (500 MHz, CDCl$_3$-d) δ ppm 7.72 (d, J=8.4 Hz, 1H) 7.64 (d, J=1.5 Hz, 1H) 7.46 (dd, J=8.4, 1.6 Hz, 1H) 3.93 (s, 3H); TOF ES+ MS: (M+H) 248.9; HPLC Ret: 7.71 min.

Other derivatives were made in an analogous fashion:

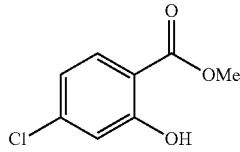

Tet. Lett. 2014, 4484-4488

Methyl 4-chloro-2-hydroxybenzoate $^1$H NMR (500 MHz, CDCl$_3$-d) δ ppm 7.78 (dd, J=8.6, 1.0 Hz, 1H) 6.96 (dd, J=2.0, 1.0 Hz, 1H) 6.93-6.84 (m, 1H) 3.94 (s, 3H); TOF ES+ MS: (M+H) 187.4; HPLC Ret: 7.63 min.

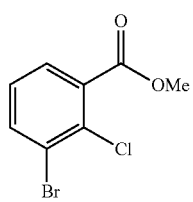 [SMILES: COC(=O)c1cccc(Br)c1Cl]

Methyl 3-bromo-2-chlorobenzoate $^1$H NMR (500 MHz, CDCl$_3$-d) δ ppm 7.77 (dd, J=8.0, 0.8 Hz, 1H) 7.68 (dd, J=7.7, 0.8, 1H) 7.19 (td, J=7.9, 0.8 Hz, 1H) 3.94 (s, 3H); TOF ES+ MS: (M+H) 250.9; HPLC Ret: 7.44 min.

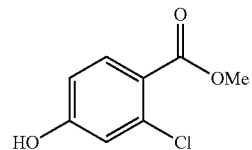

Methyl 2-chloro-4-hydroxybenzoate

HPLC Ret: 5.72 min.

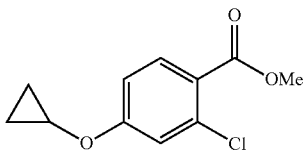 [SMILES: COC(=O)c1ccc(OC2CC2)cc1Cl]

Methyl 2-chloro-4-cyclopropoxybenzoate $^1$H NMR (500 MHz, CDCl$_3$-d) δ ppm 7.86 (d, 8.5 Hz, 1H) 7.14 (d, J=2.5 Hz, 1H) 6.94 (dd, J=8.8, 2.4 Hz, 1H) 3.90 (s, 3H) 3.77 (tt, J=6.4, 3.0 Hz, 1H) 0.88-0.75 (m, 4H); TOF ES$^+$ MS: (M+H) 226.14; HPLC Ret: 7.67 min.

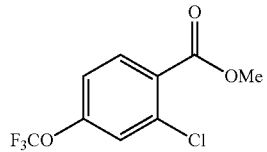

Methyl 2-chloro-4-(trifluoromethoxy)benzoate

Column: 5% EtOAc: 95% Hex. $^1$H NMR (500 MHz, CDCl$_3$-d) δ ppm 7.92 (d, J=8.7 Hz, 1H) 7.33 (d, J=2.3 Hz, 1H) 7.18 (dd, J=8.7, 2.4 Hz, 1H) 3.94 (s, 3H); HPLC Ret: 7.90 min. *CF$_3$ group may be unstable to refluxing acid.

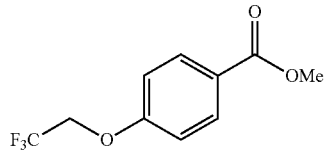 [SMILES: COC(=O)c1ccc(OCC(F)(F)F)cc1]

Methyl 4-(2,2,2-trifluoroethoxy)benzoate $^1$H NMR (500 MHz, CDCl$_3$-d) δ ppm 8.03 (d, J=8.6 Hz, 2H) 6.97 (d, J=8.6 Hz, 2H) 4.41 (q, 8.0 Hz, 2H) 3.90 (s, 3H); HPLC Ret: 7.23 min.

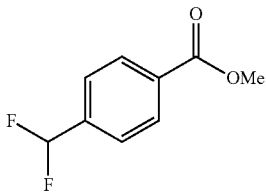 [SMILES: COC(=O)c1ccc(C(F)F)cc1]

Methyl 4-(difluoromethyl)benzoate $^1$H NMR (500 MHz, CDCl$_3$-d) δ ppm 8.13 (d, J=8.0 Hz, 2H) 7.59 (d, J=8.0 Hz, 2H) 6.69 (t, 56.1 Hz, 1H) 3.95 (s, 3H); HPLC Ret: 6.79 min.

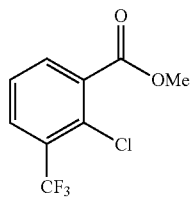

Methyl 2-chloro-3-(trifluoromethyl)benzoate $^1$H NMR (500 MHz, CDCl$_3$-d) δ ppm 7.91-7.80 (m, 2H) 7.44 (t, J=7.9 Hz, 1H) 3.97 (s, 3H); HPLC Ret: 7.47 min.

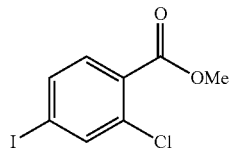 [SMILES: COC(=O)c1ccc(I)cc1Cl]

Methyl 2-chloro-4-iodobenzoate $^1$H NMR (500 MHz, CDCl$_3$-d) δ ppm 7.85 (d, 1.6 Hz, 1H) 7.67 (dd, J=8.2, 1.7 Hz, 1H) 7.55 (d, J=8.2 Hz, 1H) 3.91 (s, 3H); HPLC Ret: 7.88 min.

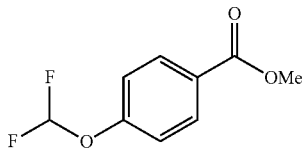 [SMILES: COC(=O)c1ccc(OC(F)F)cc1]

Methyl 4-(difluoromethoxy)benzoate $^1$H NMR (500 MHz, CDCl$_3$-d) δ ppm 8.06 (d, J=8.4 Hz, 2H) 7.16 (d, J=8.4 Hz, 2H) 6.59 (t, 73.2 Hz, 1H) 3.92 (s, 3H).

Preparation 4: Methyl 2-chloro-4-cyclopropylbenzoate

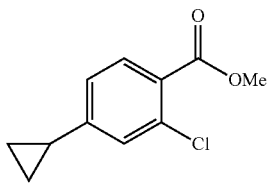

Tet. Lett. 2002, 6987-6990

Methyl 4-bromo-2-chlorobenzoate (0.27 g, 1.08 mmol) was dissolved in 5 mL of toluene (degassed) under inert atmosphere. H$_2$O (0.20 g, 0.20 mL, 10.8 mmol), potassium phosphate dibasic (0.66 g, 3.79 mmol), cyclopropyl boronic acid (0.12 g, 1.41 mmol), tricyclohexylphosphine (0.03 g, 0.11 mmol), and palladium (II) acetate (0.036 g, 0.16 mmol) were added. The mixture was heated at reflux (100° C.) for 3 hr under N$_2$. The mixture was cooled to 25° C. and 10 mL H$_2$O was added. The product was extracted with EtOAc (3×, 15 mL), washed with brine (2×15 mL), dried with MgSO$_4$, and concentrated in vacuo. The yellow residue was subjected to silica gel chromatography eluting with 2.5% EtOAc: 97.5% Hex. The fractions containing product were concentrated in vacuo. $^1$H NMR (500 MHz, CDCl$_3$-d) δ ppm 7.81-7.70 (m, 1H) 7.15-7.12 (m, 1H) 7.03-6.94 (m, 1H) 3.90 (s, 3H) 1.95-1.84 (m, 1H) 1.11-1.00 (m, 2H) 0.81-0.70 (m, 2H); TOF ES+ MS: (M+H) 211.0; HPLC Ret: 7.29 min.

Other derivatives were made in an analogous fashion:

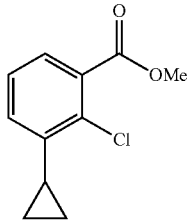 [SMILES: COC(=O)c1cccc(C2CC2)c1Cl]

Methyl 2-chloro-3-cyclopropylbenzoate $^1$H NMR (500 MHz, CDCl$_3$-d) δ ppm 7.51 (dd, J=7.7, 1.7 Hz, 1H) 7.21 (t, J=7.7 Hz, 1H) 7.10 (dd, J=7.8, 1.6 Hz, 1H) 3.94 (s, 3H) 2.29-2.21 (m, 1H) 1.09-0.96 (m, 2H) 0.71-0.66 (m, 2H); TOF ES+ MS: (M+H) 211.0; HPLC Ret: 7.31 min.

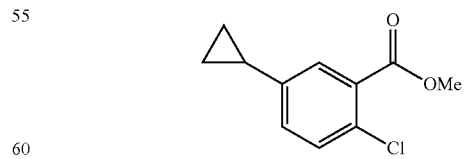

Methyl 2-chloro-5-cyclopropylbenzoate $^1$H NMR (500 MHz, CDCl$_3$-d) δ ppm 7.51 (d, J=1.6 Hz, 1H) 7.33 (d, J=8.2 Hz, 1H) 7.11 (dd, J=7.9, 1.5 Hz, 1H) 3.93

(s, 3H) 1.93-1.86 (m, 1H) 1.05-0.98 (m, 2H) 0.73-0.68 (m, 2H); TOF ES+ MS: (M+H) 211.0; HPLC Ret: 7.31 min.

Preparation 5: Methyl 2-(benzyloxy)-4-chlorobenzoate

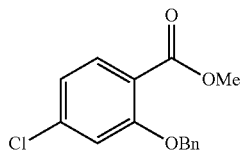 [SMILES: COC(=O)c1ccc(Cl)cc1OCc1ccccc1]

Methyl 4-chloro-2-hydroxybenzoate (1.0 g, 5.36 mmol) was dissolved in 15 mL DMF. $K_2CO_3$ (1.48 g, 10.7 mmol) and benzyl bromide (1.10 g, 6.43 mmol, 0.77 mL) were added and the mixture was stirred at 90° C. for 4 hr. The reaction was diluted with brine and extracted with DCM (3×20 mL). The organic layers were combined, dried with $MgSO_4$, and evaporated in vacuo. The subsequent oil was subjected to silica gel chromatography eluting with 10% EtOAc: 90% Hex. The fractions containing product were concentrated in vacuo $^1$H NMR (500 MHz, $CDCl_3$-d) δ ppm 7.78 (d, J=8.3, 1H) 7.52-7.45 (m, 2H) 7.43-7.36 (m, 2H) 7.32 (t, J=7.4 Hz, 1H) 7.03-6.94 (m, 2H) 5.15 (s, 2H) 3.88 (s, 3H); TOF ES+ MS: (M+Na) 298.9; HPLC Ret: 8.17 min.

Preparation 6: Methyl 2-chloro-4-(prop-2-yn-1-yloxy)benzoate

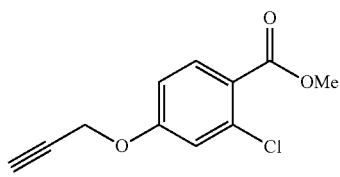

In a 250 mL round bottomed flask methyl 2-chloro-4-hydroxybenzoate (1.83 g, 9.81 mmol) was dissolved in anhydrous acetone (30 mL) and placed under inert atmosphere. $K_2CO_3$ (1.76 g, 12.75 mmol) and prop-2-yn-benzenesulfonate (2.89 g, 14.7 mmol, 2.3 mL) were added and the reaction proceeded at reflux (60° C.) for 3 hr under inert atmosphere. The acetone was evaporated in vacuo and the residue was taken up in water (30 mL). The product was extracted with EtOAc (3×30 mL), washed with brine (2×15 mL), dried with $MgSO_4$, and the evaporated in vacuo. The oil was subjected to silica gel chromatography eluting with 15% EtOAc: 85% Hex. The fractions containing product were concentrated in vacuo $^1$H NMR (400 MHz, $CDCl_3$-d) δ ppm 7.89 (d, J=8.8, 1H) 7.06 (d, J=2.5 Hz, 1H) 6.91 (dd, J=8.8, 2.5 Hz, 1H) 4.73 (d, J=2.4 Hz, 2H) 3.90 (s, 3H) 2.58 (t, J=2.4 Hz, 1H); TOF ES+ MS: (M+H) 224.9; HPLC Ret: 6.99 min.

Other derivatives were made in an analogous fashion:

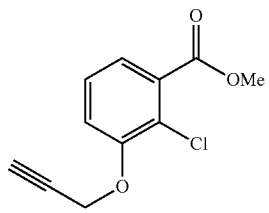

Methyl 2-chloro-3-(prop-2-yn-1-yloxy)benzoate (DJK-2-98). Yield=76%. Pale yellow oil. $^1$H NMR (500 MHz, $CDCl_3$-d) δ ppm 7.40 (dd, J=7.7, 1.6 Hz, 1H) 7.29 (t, 8.3 Hz, 1H) 7.23 (dd, J=8.3, 1.5 Hz, 1H) 4.81 (d, J=2.4 Hz, 2H) 3.93 (s, 3H) 2.55 (t, J=2.4 Hz, 1H); TOF ES+ MS: (M+H) 225.0; HPLC Ret: 6.74 min.

Preparation 7: Methyl 2-chloro-4-(2,2,2-trifluoroethoxy)benzoate

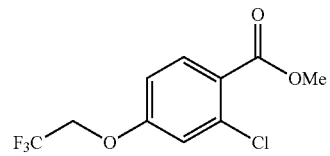 [SMILES: COC(=O)c1ccc(OCC(F)(F)F)cc1Cl]

In a 50 mL round-bottomed flask methyl 2-chloro-4-hydroxybenzoate (0.3 g, 1.60 mmol) was dissolved in 6 mL anhydrous DMSO. $Cs_2CO_3$ (0.68 g, 2.09 mmol) and 1,1,1-trifluoro-2-iodoethane (0.44 g, 0.21 mL, 2.09 mmol) were added and the reaction was heated at 105° C. for 16 hr. The reaction was cooled, diluted with $H_2O$, and extracted with EtOAc (3×20 mL). The organic layers were combined, washed with brine (2×15 mL), and concentrated in vacuo. The yellow residue was subjected to silica gel chromatography eluting with 5% EtOAc: 95% Hex. The fractions containing product were concentrated in vacuo. $^1$H NMR (500 MHz, $CDCl_3$-d) δ ppm 7.91 (d, J=8.8 Hz, 1H) 7.03 (d, J=2.6 Hz, 1H) 6.88 (dd, J=8.8, 2.6 Hz, 1H) 4.39 (q, J=7.8 Hz, 2H) 3.91 (s, 3H); TOF ES+ MS: (M+H) 269.1; HPLC Ret: 7.50 min.

Other derivatives were made in an analogous fashion:

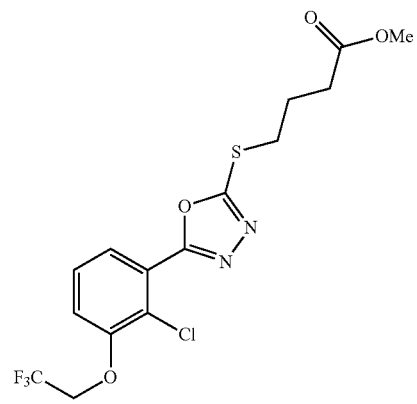 [SMILES: COC(=O)CCCSc1nnc(-c2cccc(OCC(F)(F)F)c2Cl)o1]

Methyl 4-((5-(2-chloro-3-(2,2,2-trifluoroethoxy)phenyl)-1,3,4-oxadiazol-2-yl)thio)butanoate

*note: methyl 4-((5-(2-chloro-3-hydroxyphenyl)-1,3,4-oxadiazol-2-yl)thio)butanoate used as starting material; silica gel chromatography eluting with 35% EtOAc: 65% Hex. $^1$H NMR (500 MHz, CDCl$_3$-d) δ ppm 7.67 (dt, 7.9, 1.2 Hz, 1H) 7.38 (t, J=8.1 Hz, 1H) 7.16 (dd, J=8.3, 1.4 Hz, 1H) 4.51-4.41 (m, 2H) 3.70 (s, 3H) 3.38 (t, J=7.2 Hz, 2H) 2.54 (t, J=7.1 Hz, 2H) 2.22 (p, J=7.0 Hz, 2H); TOF ES+ MS: (M+H) 411.04; HPLC Ret: 7.46 min.

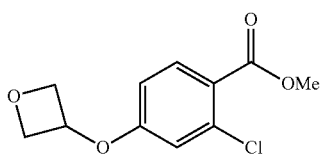 [SMILES: COC(=O)c1ccc(OC2COC2)cc1Cl]

Methyl 2-chloro-4-(oxetan-3-yloxy)benzoate

*8 hr rxn time and 25% EtOAc:75% Hex to 35%: EtOAc:65% Hex chromatography. $^1$H NMR (500 MHz, CDCl$_3$-d) δ ppm 7.87 (d, J=8.7 Hz, 1H) 6.76 (d, J=2.5 Hz, 1H) 6.64 (dd, J=8.8, 2.5 Hz, 1H) 5.28-5.20 (m, 2H) 5.02-4.95 (m, 2H) 4.78-4.72 (m, 2H) 3.90 (s, 3H); HPLC Ret: 6.39 min.

Preparation 8: Methyl 2-chloro-4-(oxetan-3-ylmethoxy)benzoate

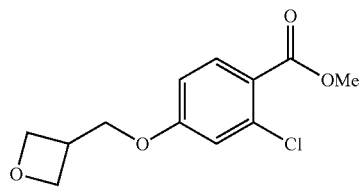 [SMILES: COC(=O)c1ccc(OCC2COC2)cc1Cl]

Methyl 2-chloro-4-hydroxybenzoate (0.16 g, 0.88 mmol) was dissolved in 3.0 mL DMF. oxetan-3-ylmethyl methanesulfonate (0.19 g, 1.14 mmol) along with K$_2$CO$_3$ (0.16 g, 1.14 mmol) were added and the reaction was stirred at 90° C. for 1.5 hr. The reaction was diluted with 10 mL brine and extracted with DCM (3×15 mL). The organic layers were combined, dried with MgSO$_4$, and evaporated in vacuo. The subsequent oil was subjected to silica gel chromatography eluting with 30% EtOAc: 70% Hex. The fractions containing product were concentrated in vacuo. $^1$H NMR (500 MHz, CDCl$_3$-d) δ ppm 7.89 (d, J=8.8 Hz, 1H) 6.99 (d, J=2.5 Hz, 1H) 6.84 (dd, J=8.8, 2.5 Hz, 1H) 4.89 (dd, J=7.8, 6.3 Hz, 2H) 4.56 (t, J=6.1 Hz, 2H) 4.24 (d, J=6.7 Hz, 2H) 3.90 (s, 3H) 3.50-3.40 (m, 1H); HPLC Ret: 6.38 min.

Similar analogs were made in an analogous fashion:

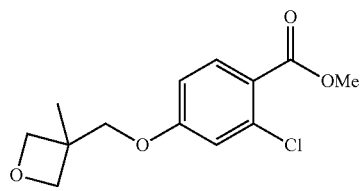 [SMILES: COC(=O)c1ccc(OCC2(C)COC2)cc1Cl]

Methyl 2-chloro-4-(oxetan-3-ylmethoxy)benzoate

Column: 40% EtOAc: 60% Hex. Yellow oil. Yield=92%. $^1$H NMR (500 MHz, CDCl$_3$-d) δ ppm 7.89 (d, J=8.8 Hz, 1H) 7.02 (d, J=2.5 Hz, 1H) 6.86 (dd, J=8.8, 2.5 Hz, 1H) 4.60 (d, J=6.0 Hz, 2H) 4.47 (d, J=6.0 Hz, 2H) 4.07 (s, 2H) 3.90 (s, 3H) 1.44 (s, 3H); HPLC Ret: 6.91 min.

Preparation 9: Methyl 4-(2-hydroxypropan-2-yl)benzoate

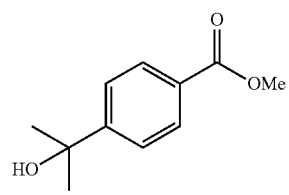

WO2006013048

In a 100 mL round-bottomed flask, methyl 4-iodobenzoate (1.0 g, 3.8 mmol) was dissolved in 10 mL THF and cooled to 0° C. 2M iPrMgCl in THF (2.0 mL, 4.01 mmol) was added dropwise and the reaction was stirred at −40° C. for 1.5 hr. Acetone (0.33 g, 0.42 mL, 5.7 mmol) was then added and the reaction was stirred at 25° C. for 1 hr. The reaction was quenched with MeOH and then diluted with H$_2$O. The product was extracted with EtOAc (3×15 mL), and the organic layers were combined, washed with brine (2×15 mL), dried with MgSO$_4$, and concentrated in vacuo. The subsequent oil was subjected to silica gel chromatography eluting with 20% EtOAc: 80% Hex. The fractions containing product were concentrated in vacuo. $^1$H NMR (500 MHz, CDCl$_3$-d) δ ppm 8.00 (d, J=7.4 Hz, 2H) 7.56 (d, J=7.4 Hz, 2H) 3.91 (s, 3H) 1.60 (s, 6H); HPLC Ret: 5.60 min.

Similar derivatives were made in an analogous fashion:

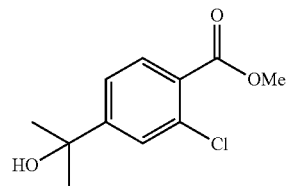

Methyl 2-chloro-4-(2-hydroxypropan-2-yl)benzoate

Column: 30% EtOAc: 70% Hex. $^1$H NMR (500 MHz, CDCl$_3$-d) δ ppm 7.81 (d, J=8.2 Hz, 1H) 7.59 (d, J=1.7 Hz, 1H) 7.41 (dd, J=8.2, 1.8 Hz, 1H) 3.93 (s, 3H) 1.58 (s, 6H); HPLC Ret: 6.09 min.

Preparation 10: Methyl 2-chloro-4-(2-fluoropropan-2-yl)benzoate

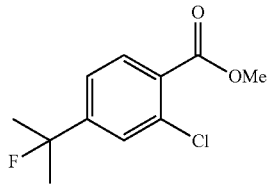

In a flame dried 25-mL round bottomed flask, methyl 2-chloro-4-(2-hydroxypropan-2-yl)benzoate (0.11 g, 0.48 mmol) was dissolved in DCM (2 mL) and cooled to −78° C. DAST (0.08 g, 0.06 mL, 0.48 mmol) was added and the solution was stirred at 25° C. for 2 hr. The reaction was diluted with $H_2O$, and the product was extracted with DCM (3×20 mL). The organic layers were combined, washed with brine (2×15 mL), dried with $MgSO_4$, and concentrated in vacuo. The oil was subjected to silica gel chromatography eluting with 2.5% EtOAc: 97.5% Hex to 5% EtOAc: 95% Hex. The fractions containing product were concentrated. $^1$H NMR (500 MHz, $CDCl_3$-d) δ ppm 7.83 (d, J=8.2 Hz, 1H) 7.47 (d, J=1.7 Hz, 1H) 7.30 (dd, J=8.2, 1.7 Hz, 1H) 3.93 (s, 3H) 1.70 (d, J=1.5 Hz, 3H) 1.65 (d, J=1.5 Hz, 3H); $^{19}$F NMR (500 MHz, $CDCl_3$-d) δ ppm −139.4 (hept., 1H); HPLC Ret: 8.02 min.

Similar derivatives were made in an analogous fashion:

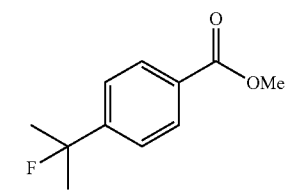

Methyl 4-(2-fluoropropan-2-yl)benzoate. $^1$H NMR (500 MHz, $CDCl_3$-d) δ ppm 8.03 (d, J=8.4 Hz, 2H) 7.45 (d, J=8.4 Hz, 2H) 3.92 (s, 3H) 1.72 (d, J=1.3 Hz, 3H) 1.67 (d, J=1.3 Hz, 3H); $^{19}$F NMR (500 MHz, $CDCl_3$-d) δ ppm −138.9 (hept., 1H); HPLC Ret: 7.74 min.

Preparation 11: 2-chloro-4-cyclopropylbenzohydrazide

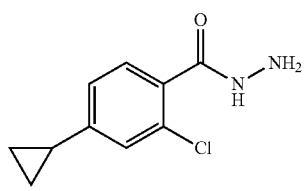 [SMILES: NNC(=O)c1ccc(C2CC2)cc1Cl]

Methyl 2-chloro-4-cyclopropylbenzoate (0.12 g, 0.56 mmol) was dissolved in 4 mL MeOH, hydrazine (0.37 g, 0.35 mL, 11.1 mmol) was added, and the mixture was refluxed at 85° C. for 16 hr. MeOH was evaporated and the remaining oil was partitioned between $H_2O$ (10 mL) and DCM (10 mL). The product was extracted with DCM (3×10 mL), washed with brine (2×15 mL), dried with $MgSO_4$, and concentrated in vacuo $^1$H NMR (500 MHz, $CDCl_3$-d) δ ppm 7.63-7.52 (m, 1H) 7.09 (s, 1H) 7.02-7.00 (m, 1H) 4.12 (br. s., 2H) 1.93-1.84 (m, 1H) 1.05 (dtd, J=6.4, 4.8, 1.3 Hz, 2H) 0.74 (dtd, J=6.4, 4.8, 1.3 Hz, 2H); TOF ES+ MS: (M+H) 211.0; HPLC Ret: 4.64 min.

Similar derivatives were made in an analogous fashion:

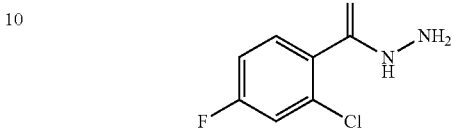

2-Chloro-4-fluorobenzohydrazide $^1$H NMR (401 MHz, DMSO-$d_6$) δ ppm 9.58 (s, 1H) 7.54-7.41 (m, 2H) 7.30-7.25 (m, 1H) 4.50 (br. s., 2H); HPLC Ret: 3.43 min.

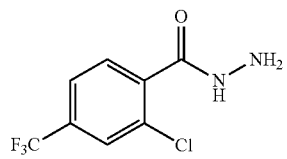 [SMILES: NNC(=O)c1ccc(C(F)(F)F)cc1Cl]

2-Chloro-4-(trifluoromethyl)benzohydrazide $^1$H NMR (500 MHz, $CDCl_3$-d) δ ppm 7.75 (d, J=8.1 Hz, 1H) 7.70 (d, J=1.7 Hz, 1H) 7.60 (dd, J=8.0, 1.7 Hz, 1H) 7.50 (br. s., 1H) 3.94 (br. s., 2H); TOF ES+ MS: (M+H) 239.0; HPLC Ret: 4.48 min.

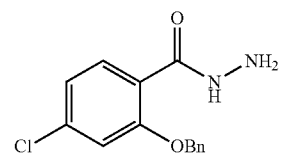 [SMILES: NNC(=O)c1ccc(Cl)cc1OCc1ccccc1]

Methyl 2-(benzyloxy)-4-chlorobenzoate $^1$H NMR (500 MHz, DMSO-$d_6$) δ ppm 9.22 (s, 1H) 7.62 (d, J=8.2 Hz, 1H) 7.50-7.43 (m, 2H) 7.45-7.36 (m, 2H) 7.37-7.30 (m, 1H) 7.27 (d, J=1.9 Hz, 1H) 7.08 (dd, J=8.3, 1.9 Hz, 1H) 5.26 (s, 2H); HPLC Ret: 5.76 min.

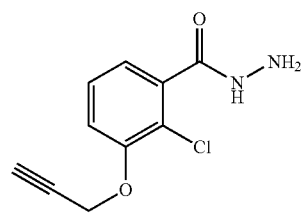

2-Chloro-3-(prop-2-yn-1-yloxy)benzohydrazide

¹H NMR (500 MHz, DMSO-d₆) δ ppm 9.52 (br. s., 1H) 7.35 (dd, J=8.4, 7.5 Hz, 1H) 7.26 (dd, 8.4, 1.4 Hz, 1H) 6.97 (dd, J=8.4, 1.4 Hz, 1H) 4.95 (d, J=2.4 Hz, 2H) 4.47 (br. s., 2H) 3.63 (t, J=2.4 Hz, 1H); TOF ES+MS: (M+H) 225.0; HPLC Ret: 6.39 min.

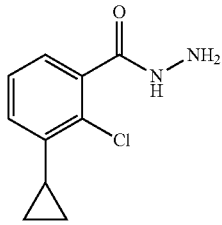 [SMILES: NNC(=O)c1cccc(C2CC2)c1Cl]

2-Chloro-3-cyclopropylbenzohydrazide (DJK-5-25). White solid. Yield=95%. ¹H NMR (500 MHz, CDCl₃-d) δ ppm 7.33 (dd, J=7.3, 1.4 Hz, 1H) 7.24 (t, J=7.5 Hz, 1H) 7.06 (dd, J=7.8, 1.6 Hz, 1H) 4.14 (d, J=4.2 Hz, 2H) 2.20 (tt, J=8.6, 5.3 Hz, 1H) 1.09-0.96 (m, 2H) 0.74-0.63 (m, 2H); TOF ES+ MS: (M+H) 211.0; HPLC Ret: 4.55 min.

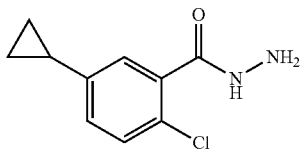 [SMILES: NNC(=O)c1cc(C2CC2)ccc1Cl]

2-Chloro-5-cyclopropylbenzohydrazide (DJK-5-26). White solid. Yield=96%. ¹H NMR (500 MHz, CDCl₃-d) δ ppm 7.41 (br. s., 1H) 7.36 (d, J=2.3 Hz, 1H) 7.28 (dd, J=8.3, 0.8 Hz, 1H) 7.08 (dd, J=8.3, 2.3 Hz, 1H) 1.89 (tt, J=8.6, 5.0 Hz, 1H) 1.08-0.94 (m, 2H) 0.76-0.64 (m, 2H); TOF ES+ MS: (M+H) 211.0; HPLC Ret: 4.59 min.

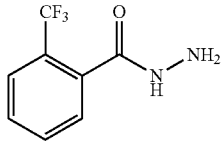 [SMILES: NNC(=O)c1ccccc1C(F)(F)F]

2-(Trifluoromethyl)benzohydrazide

¹H NMR (500 MHz, CDCl₃-d) δ ppm 7.73 (dd, J=7.7, 1.3 Hz, 1H) 7.65-7.48 (m, 3H) 6.98 (br. s, 1H) 4.12 (br. s, 2H); TOF ES+ MS: (M+H) 205.1; HPLC Ret: 3.25 min.

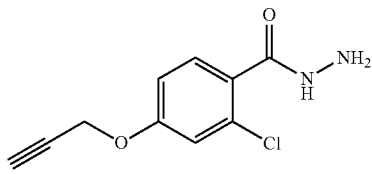

2-Chloro-4-(prop-2-yn-1-yloxy)benzohydrazide

¹H NMR (400 MHz, CDCl₃-d) δ ppm 7.77 (br. s., 1H) 7.64 (d, 8.7 Hz, 1H) 7.00 (d, J=2.5 Hz, 1H) 6.92 (dd, J=8.7, 2.5 Hz, 1H) 4.72 (d, J=2.4 Hz, 2H) 4.16 (br. s., 2H) 2.59 (t, J=2.4 Hz, 1H); TOF ES+ MS: (M+H) 224.9; HPLC Ret: 4.28 min.

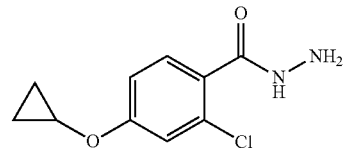 [SMILES: NNC(=O)c1ccc(OC2CC2)cc1Cl]

2-Chloro-4-cyclopropoxybenzohydrazide

¹H NMR (500 MHz, CDCl₃-d) δ ppm 7.69 (d, 8.7 Hz, 1H) 7.54 (br. s, 1H) 7.09 (d, J=2.4 Hz, 1H) 6.99 (dd, J=8.7, 2.4 Hz, 1H) 4.13 (br. s, 2H) 3.80-3.72 (m, 1H) 0.88-0.73 (m, 4H); TOF ES' MS: (M+H) 227.06; HPLC Ret: 4.57 min.

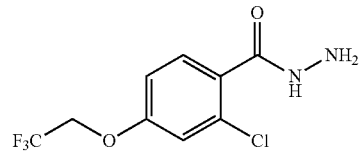 [SMILES: NNC(=O)c1ccc(OCC(F)(F)F)cc1Cl]

2-Chloro-4-(2,2,2-trifluoroethoxy)benzohydrazide

¹H NMR (500 MHz, CDCl₃-d) δ ppm 7.74 (d, 8.7 Hz, 1H) 7.50 (br. s, 1H) 7.01 (d, J=2.6 Hz, 1H) 6.92 (dd, J=8.7, 2.6 Hz, 1H) 4.39 (q, J=7.9 Hz, 2H) 4.13 (d, J=4.3 Hz, 2H); TOF ES' MS: (M+H) 269.03; HPLC Ret: 4.81 min.

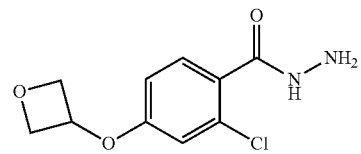 [SMILES: NNC(=O)c1ccc(OC2COC2)cc1Cl]

2-Chloro-4-(oxetan-3-yloxy)benzohydrazide

¹H NMR (500 MHz, CDCl₃-d) δ ppm 7.69 (d, 8.7 Hz, 1H) 7.51 (br. s, 1H) 6.74 (d, J=2.5 Hz, 1H) 6.67 (dd, J=8.7, 2.5 Hz, 1H) 5.22 (pd, 6.0, 1.0 Hz, 1H) 4.98 (t, J=7.1 Hz, 2H) 4.74 (dd, J=7.3, 5.1 Hz, 2H) 4.12 (d, J=4.1 Hz, 2H); TOF ES⁺ MS: (M+H) 243.05; HPLC Ret: 3.10 min.

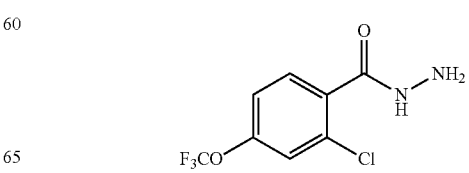

2-Chloro-4-(trifluoromethoxy)benzohydrazide

¹H NMR (500 MHz, CDCl₃-d) δ ppm 7.73 (d, 8.6 Hz, 1H) 7.39 (br. s, 1H) 7.31 (d, J=2.1 Hz, 1H) 7.22 (dd, J=8.8, 2.1 Hz, 1H) 4.15 (br. s, 2H); TOF ES⁺ MS: (M+H) 255.01; HPLC Ret: 4.97 min.

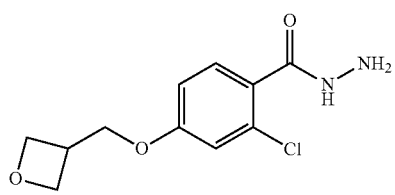 [SMILES: NNC(=O)c1ccc(OCC2COC2)cc1Cl]

2-Chloro-4-(oxetan-3-ylmethoxy)benzohydrazide

¹H NMR (500 MHz, CDCl₃-d) δ ppm 7.73 (d, 8.6 Hz, 1H) 7.54 (br. s, 1H) 6.96 (d, J=2.4 Hz, 1H) 6.89 (dd, J=8.8, 2.4 Hz, 1H) 4.89 (td, 6.1, 3.0 Hz, 2H) 4.56 (td, J=6.1, 3.0 Hz, 2H) 4.23 (dd, J=6.7, 3.0 Hz, 2H) 4.13 (br. s, 2H) 3.48-3.41 (m, 1H); TOF ES⁺ MS: (M+H) 257.07; HPLC Ret: 3.65 min.

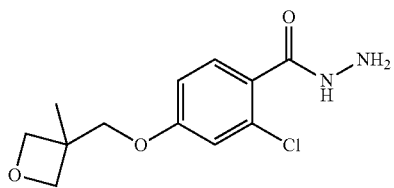 [SMILES: CC1(COc2ccc(C(=O)NN)c(Cl)c2)COC1]

2-Chloro-4-((3-methyloxetan-3-yl)methoxy)benzohydrazide

¹H NMR (500 MHz, CDCl₃-d) δ ppm 7.73 (d, 8.6 Hz, 1H) 7.56 (br. s, 1H) 6.99 (d, J=2.4 Hz, 1H) 6.91 (dd, J=8.8, 2.4 Hz, 1H) 4.60 (dd, J=6.1, 3.3 Hz, 2H) 4.47 (dd, J=6.1, 3.4 Hz, 2H) 4.13 (br. s, 2H) 4.06 (s, 2H) 1.44 (s, 3H); TOF ES⁺ MS: (M+H) 271.08; HPLC Ret: 4.21 min.

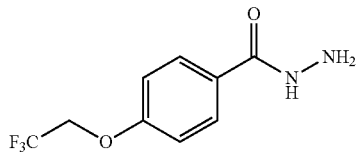 [SMILES: NNC(=O)c1ccc(OCC(F)(F)F)cc1]
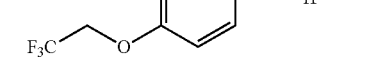

4-(2,2,2-Trifluoroethoxy)benzohydrazide

¹H NMR (500 MHz, CDCl₃-d) δ ppm 7.75 (d, 8.8 Hz, 2H) 7.26 (br. s, 1H) 7.00 (d, J=8.8 Hz, 2H) 4.40 (q, J=8.0 Hz, 2H) 4.09 (d, J=3.8 Hz, 2H); TOF ES⁺ MS: (M+H) 235.07; HPLC Ret: 4.65 min.

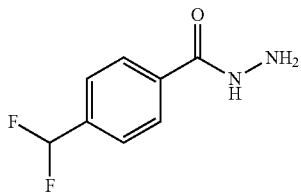 [SMILES: NNC(=O)c1ccc(C(F)F)cc1]

4-(difluoromethyl)benzohydrazide

¹H NMR (500 MHz, CDCl₃-d) δ ppm 7.84 (d, 7.8 Hz, 2H) 7.61 (d, J=7.8 Hz, 2H) 7.37 (br. s, 1H) 6.69 (t, J=56.2 Hz, 1H) 4.12 (br. s, 2H); TOF ES⁺ MS: (M+H) 187.07; HPLC Ret: 3.84 min.

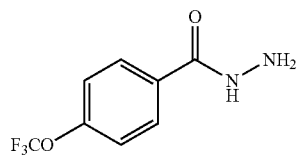 [SMILES: NNC(=O)c1ccc(OC(F)(F)F)cc1]

4-(Trifluoromethoxy)benzohydrazide

¹H NMR (500 MHz, CDCl₃-d) δ ppm 7.80 (d, J=8.0 Hz, 2H) 7.36 (br. s, 1H) 7.33-7.25 (m, 2H) 4.11 (br.s, 2H); TOF ES⁺ MS: (M+H) 221.05; HPLC Ret: 4.71 min.

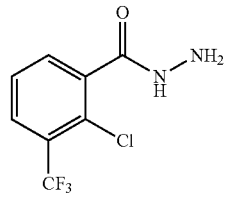 [SMILES: NNC(=O)c1cccc(C(F)(F)F)c1Cl]

2-Chloro-3-(trifluoromethyl)benzohydrazide

¹H NMR (500 MHz, CDCl₃-d) δ ppm 7.80 (d, 8.1 Hz, 1H) 7.69 (d, J=8.1 Hz, 1H) 7.46 (t, J=7.7 Hz, 1H) 7.20 (br. s, 1H) 4.16 (br. s, 2H); TOF ES⁺ MS: (M+H) 239.02; HPLC Ret: 4.71 min.

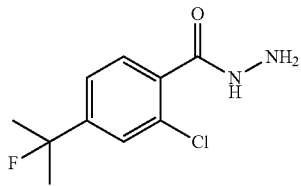
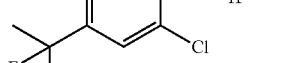

2-Chloro-4-(2-fluoropropan-2-yl)benzohydrazide

¹H NMR (500 MHz, CDCl₃-d) δ ppm 7.67 (d, 8.1 Hz, 1H) 7.47-7.42 (m, 2H) 7.32 (dd, J=8.1, 1.7 Hz, 1H) 4.15 (d, J=4.3 Hz, 2H) 1.69 (s, 3H) 1.65 (s, 3H); TOF ES⁺ MS: (M+H) 231.07; HPLC Ret: 4.76 min.

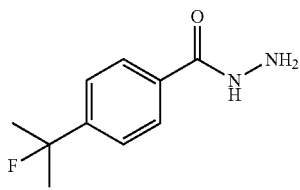

4-(2-Fluoropropan-2-yl)benzohydrazide $^1$H NMR (500 MHz, CDCl$_3$-d) δ ppm 7.74 (d, 8.0 Hz, 2H) 7.46 (d, J=8.0 Hz, 2H) 7.30 (br. s, 1H) 4.10 (br. s, 2H) 1.71 (s, 3H) 1.67 (s, 3H); TOF ES$^+$ MS: (M+H) 197.11; HPLC Ret: 4.51 min.

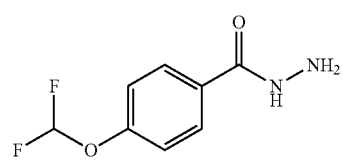 [SMILES: NNC(=O)c1ccc(OC(F)F)cc1]

4-(Difluoromethoxy)benzohydrazide $^1$H NMR (400 MHz, CDCl$_3$-d) δ ppm 7.77 (d, J=8.5 Hz, 2H) 7.30 (br. s, 1H) 7.19 (d, J=8.5 Hz, 2H) 6.58 (t, J=73.1 Hz, 1H) 4.10 (br. s, 2H); TOF ES$^+$ MS: (M+H) 203.06; HPLC Ret: 4.19 min.

Preparation 12: 5-(2-Chloro-4-cyclopropylphenyl)-1,3,4-oxadiazole-2-thiol

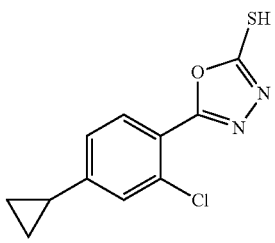 [SMILES: Sc1nnc(-c2ccc(C3CC3)cc2Cl)o1]

In a 50 mL round-bottomed flask 2-chloro-4-cyclopropylbenzohydrazide (0.1 g, 0.48 mmol) was dissolved in a solution of KOH (0.03 g, 0.48 mmol) in EtOH/H$_2$O (4.0 mL/0.09 mL, 4.8 mmol). Carbon disulfide (0.04 g, 0.03 mL, 0.48 mmol) was added and the reaction was stirred at reflux (95° C.) for 16 hr. Upon completion, most of the EtOH was evaporated in vacuo and the product was acidified to pH 1 with 1 N HCl (15 mL). The subsequent precipitate was filtered and dried under vacuum. $^1$H NMR (500 MHz, CDCl$_3$-d) δ ppm 10.53 (br. s., 1H) 7.81-7.73 (m, 1H) 7.23 (s, 1H) 7.08 (dd, J=8.2, 1.8 Hz, 1H) 1.96-1.91 (m, 1H) 1.12 (dt, J=6.8, 4.8, Hz, 2H) 0.81 (dt, J=6.8, 4.8, Hz, 2H); TOF ES+ MS: (M+H) 253.0; HPLC Ret: 7.14 min.

Other derivatives were made in the same fashion:

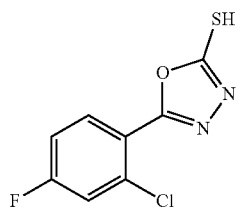 [SMILES: Fc1ccc(-c2nnc(S)o2)c(Cl)c1]

5-(2-Chloro-4-fluorophenyl)-1,3,4-oxadiaole-2-thiol $^1$H NMR (401 MHz, DMSO-d$_6$) δ ppm 7.98 (dd, J=8.9, 6.0 Hz, 1H) 7.76 (dd, J=8.9, 2.6 Hz, 1H) 7.45 (t, J=8.0 Hz, 1H); HPLC Ret: 6.42 min.

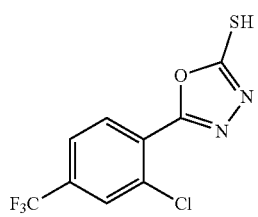 [SMILES: FC(F)(F)c1ccc(-c2nnc(S)o2)c(Cl)c1]

5-(2-Chloro-4-((trifluoromethyl)phenyl)-1,3,4-oxadiazole-2-thiol $^1$H NMR (500 MHz, DMSO-d$_6$) δ ppm 8.16-8.09 (m, 2H) 7.95-7.89 (m, 1H); TOF ES+ MS: (M+H) 280.1 HPLC Ret: 7.14 min.

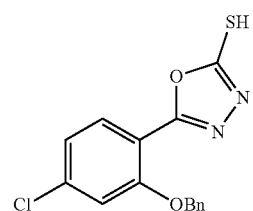 [SMILES: Sc1nnc(-c2ccc(Cl)cc2OCc2ccccc2)o1]

5-(2-(Benzyloxy)-4-chlorophenyl)-1,3,4-oxadiazol-2-thiol $^1$H NMR (400 MHz, DMSO-d$_6$) δ ppm 12.41 (br. s., 1H) 7.77 (d, J=8.4 Hz, 1H) 7.52 (d, J=1.9 Hz, 1H) 7.47-7.27 (m, 5H) 7.20 (dd, J=8.4, 1.9 Hz, 1H) 5.33 (s, 2H); TOF ES+ MS: (M+Na) 341.0; HPLC Ret: 7.64 min.

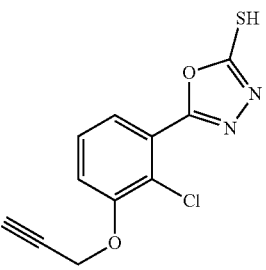 [SMILES: C#CCOc1cccc(-c2nnc(S)o2)c1Cl]

5-(2-Chloro-3-(prop-2-yn-1-yloxy)phenyl)-1,3,4-oxadiazole-2-thiol $^1$H NMR (400 MHz, DMSO-$d_6$) δ ppm 7.51-7.22 (m, 3H) 5.02 (d, J=2.4 Hz, 2H) 3.68 (t, J=2.4 Hz, 1H); HPLC Ret: 6.39 min.

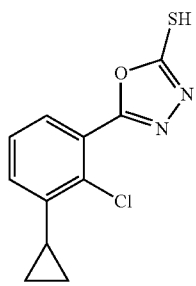 [SMILES: Sc1nnc(-c2cccc(C3CC3)c2Cl)o1]

5-(2-Chloro-3-cyclopropylphenyl)-1,3,4-oxadiazole-2-thiol $^1$H NMR (500 MHz, CDCl$_3$-d) δ ppm 10.56 (br. s., 1H) 7.69 (dd, J=7.8, 1.6 Hz, 1H) 7.32 (t, J=7.8 Hz, 1H) 7.19 (dd, J=7.8, 1.6 Hz, 1H) 2.27 (ddd, J=13.9, 8.6, 5.4 Hz, 1H) 1.15-1.03 (m, 2H) 0.77-0.65 (m, 2H); TOF ES+ MS: (M+H) 251.0; HPLC Ret: 7.16 min.

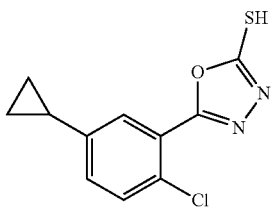 [SMILES: Sc1nnc(-c2cc(C3CC3)ccc2Cl)o1]

5-(2-Chloro-5-cyclopropylphenyl)-1,3,4-oxadiazole-2-thiol $^1$H NMR (500 MHz, CDCl$_3$-d) δ ppm 10.58 (br. s., 1H) 7.59 (d, J=2.3 Hz, 1H) 7.42 (d, J=8.3 Hz, 1H) 7.18 (dd, J=8.4, 2.3 Hz, 1H) 1.94 (ddd, J=13.4, 8.4, 5.1 Hz, 1H) 1.11-0.99 (m, 2H) 0.79-0.68 (m, 2H); TOF ES+ MS: (M+H) 251.0; HPLC Ret: 7.19 min.

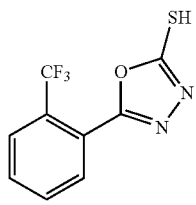 [SMILES: FC(F)(F)c1ccccc1-c1nnc(S)o1]

5-(2-(Trifluoromethyl)phenyl)-1,3,4-oxadiazole-2-thiol $^1$H NMR (500 MHz, CDCl$_3$-d) δ ppm 10.64 (br. s, 1H) 7.98-7.85 (m, 2H) 7.77-7.70 (m, 2H); TOF ES+ MS: (M+Na) 271.2; HPLC Ret: 6.49 min.

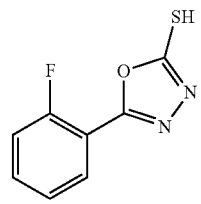 [SMILES: Fc1ccccc1-c1nnc(S)o1]

5-(2-Fluorophenyl)-1,3,4-oxadiazole-2-thiol $^1$H NMR (500 MHz, CDCl$_3$-d) δ ppm 10.78 (br. s, 1H) 7.92 (ddd, J=7.9, 7.0, 1.8 Hz, 1H) 7.58 (dddd, J=8.4, 7.5, 5.0, 1.8 Hz, 1H) 7.36-7.23 (m, 2H); TOF ES+ MS: (M+H) 195.1; HPLC Ret: 5.90 min.

5-(2-Chloro-4-(prop-2-yn-1-yloxy)phenyl)-1,3,4-oxadiazole-2-thiol $^1$H NMR (500 MHz, DMSO-$d_6$) δ ppm 7.92 (d, 8.8 Hz, 1H) 7.40 (d, J=2.5 Hz, 1H) 7.24 (dd, J=8.9, 2.6 Hz, 1H) 5.03 (d, J=2.4 Hz, 2H) 2.71 (t, J=2.4 Hz, 1H); TOF ES' MS: (M+H) 266.9; HPLC Ret: 6.58 min.

5-(2-Chloro-4-cyclopropoxyphenyl)-1,3,4-oxadiazole-2-thiol $^1$H NMR (500 MHz, CDCl$_3$-d) δ ppm 10.36 (br. s, 1H) 7.84 (d, 8.8 Hz, 1H) 7.24 (d, J=2.5 Hz, 1H) 7.06 (dd, J=8.8, 2.5 Hz, 1H) 3.85-3.77 (m, 1H) 0.92-0.79 (m, 4H); TOF ES' MS: (M+H) 269.01; HPLC Ret: 7.13 min.

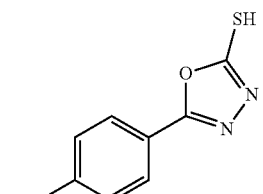

5-(4-(Trifluoromethyl)phenyl)-1,3,4-oxadiazole-2-thiol $^1$H NMR (500 MHz, CDCl$_3$-d) δ ppm 10.66 (br. s, 1H) 8.07 (d, J=8.1 Hz, 2H) 7.79 (d, J=8.1 Hz, 2H); HPLC Ret: 6.92 min.

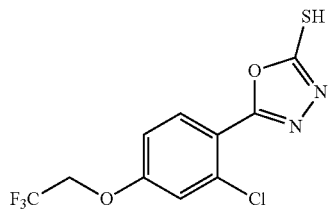 [SMILES: FC(F)(F)COc1ccc(-c2nnc(S)o2)c(Cl)c1]

5-(2-Chloro-4-(2,2,2-trifluoroethoxy)phenyl)-1,3,4

$^1$H NMR (500 MHz, CDCl$_3$-d) δ ppm 10.46 (br. s, 1H) 7.90 (d, J=8.9 Hz, 1H) 7.15 (d, J=1.9 Hz, 1H) 7.00 (dd, J=8.9, 2.0 Hz, 1H) 4.43 (q, J=7.8 Hz, 2H); HPLC Ret: 7.01 min.

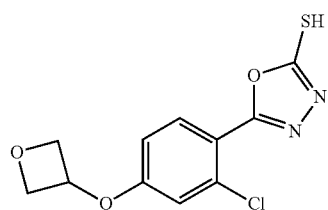 [SMILES: Sc1nnc(-c2ccc(OC3COC3)cc2Cl)o1]

5-(2-Chloro-4-(oxetan-3-yloxy)phenyl)-1,3,4-oxadiazole-2-thiol $^1$H NMR (500 MHz, CDCl$_3$-d) δ ppm 10.61 (br. s, 1H) 7.85 (d, 8.8 Hz, 1H) 6.87 (d, J=2.5 Hz, 1H) 6.74 (dd, J=8.9, 2.6 Hz, 1H) 5.27 (pd, 6.0, 1.0 Hz, 1H) 5.02 (t, J=7.1 Hz, 2H) 4.78 (dd, J=7.3, 5.1 Hz, 2H); TOF ES– MS: (M–H) 282.99; HPLC Ret: 6.03 min.

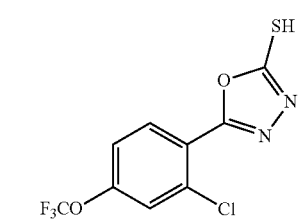

5-(2-Chloro-4-(trifluoromethoxy)phenyl)-1,3,4-oxadiazole-2-thiol $^1$H NMR (500 MHz, CDCl$_3$-d) δ ppm 10.33 (br. s, 1H) 7.97 (d, 8.7 Hz, 1H) 7.44 (d, J=2.1 Hz, 1H) 7.30 (dd, J=8.7, 2.1 Hz, 1H); TOF ES– MS: (M–H) 294.96; HPLC Ret: 7.30 min.

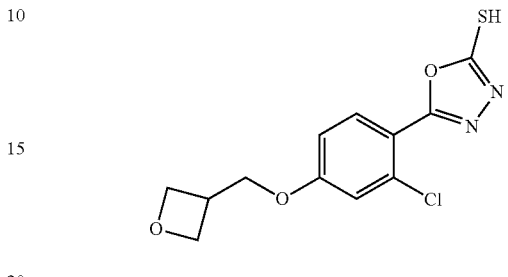

5-(2-Chloro-4-(oxetan-3-ylmethoxy)phenyl)-1,3,4-oxadiazole-2-thiol $^1$H NMR (500 MHz, DMSO-d$_6$) δ ppm 7.83 (d, 8.8 Hz, 1H) 7.32 (d, J=2.5 Hz, 1H) 7.15 (dd, J=8.9, 2.5 Hz, 1H) 4.71 (dd, J=7.9, 6.1 Hz, 2H) 4.43 (t, J=6.0 Hz, 2H) 4.35 (d, J=6.7 Hz, 2H) 3.41 (hept., 6.9 Hz, 1H); TOF ES– MS: (M–H) 297.01; HPLC Ret: 6.01 min.

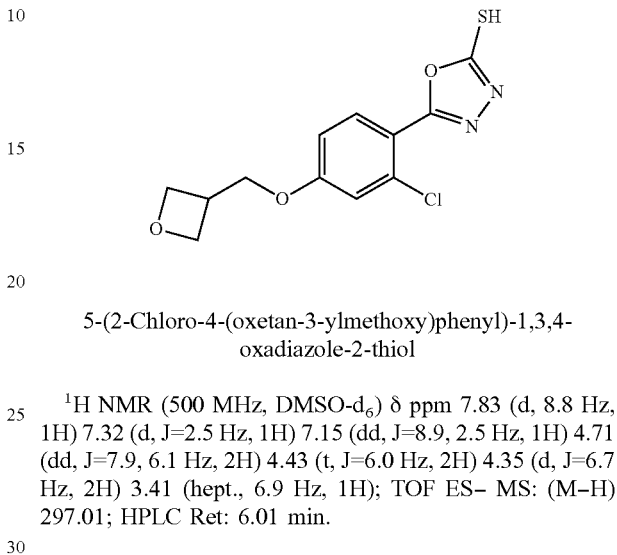

5-(2-Chloro-4-((3-methyloxetan-3-yl)methoxy)phenyl)-1,3,4-oxadiazole-2-thiol (DJK-6-88). $^1$H NMR (500 MHz, CDCl$_3$-d) δ ppm 10.43 (br. s, 1H) 7.86 (d, 8.9 Hz, 1H) 7.12 (d, J=2.5 Hz, 1H) 6.98 (dd, J=8.9, 2.5 Hz, 1H) 4.62 (d, J=6.1 Hz, 2H) 4.50 (d, J=6.1 Hz, 2H) 4.12 (s, 2H) 1.46 (s, 3H); TOF ES– MS: (M–H) 311.03; HPLC Ret: 6.46 min.

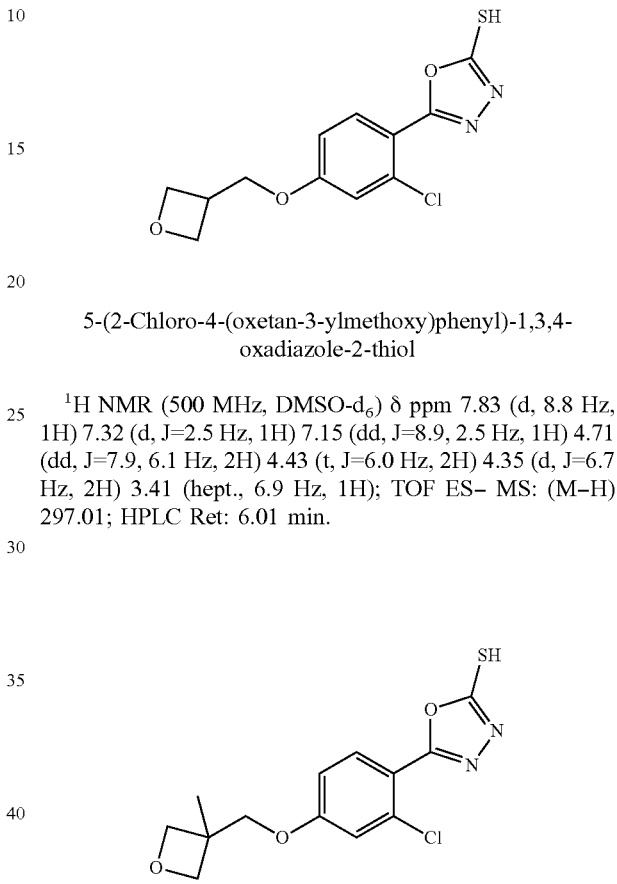

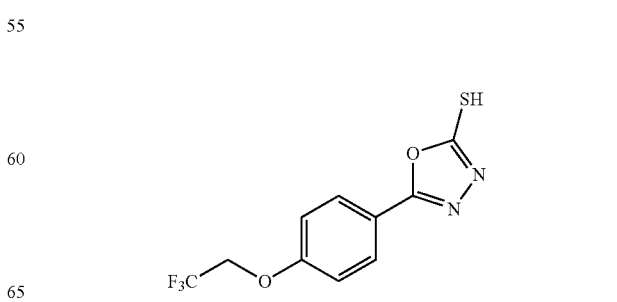

5-(4-(2,2-Trifluoroethoxy)phenyl)-1,3,4-oxadiazole-2-thiol

¹H NMR (500 MHz, CDCl₃-d) δ ppm 10.24 (br. s, 1H) 7.92 (d, J=8.9 Hz, 2H) 7.07 (d, J=8.8 Hz, 2H) 4.43 (q, J=7.9 Hz, 2H); TOF ES– MS: (M–H) 275.01; HPLC Ret: 6.83 min.

5-(2-Chloro-3-(trifluoromethyl)phenyl)-1,3,4-oxadiazole-2-thiol

¹H NMR (500 MHz, CDCl₃-d) δ ppm 10.49 (br. s, 1H) 8.08 (d, J=7.9 Hz, 1H) 7.93 (d, J=7.9 Hz, 1H) 7.57 (t, J=7.9 Hz, 1H); TOF ES– MS: (M–H) 278.96; HPLC Ret: 6.96 min.

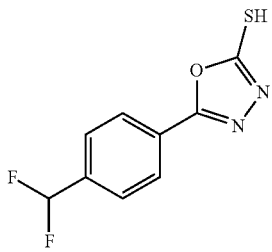 [SMILES: FC(F)c1ccc(-c2nnc(S)o2)cc1]

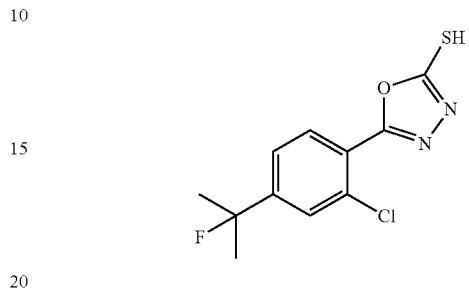

5-(4-(Difluoromethyl)phenyl)-1,3,4-oxadiazole-2-thiol (¹H NMR (500 MHz, CDCl₃-d) δ ppm 10.55 (br. s, 1H) 8.04 (d, J=8.0 Hz, 2H) 7.67 (d, J=8.0 Hz, 2H) 6.71 (t, J=56.0 Hz, 1H); TOF ES– MS: (M–H) 227.01; HPLC Ret: 6.39 min.

5-(2-Chloro-4-(2-fluoropropan-2-yl)phenyl)-1,3,4-oxadiazole-2-thiol

¹H NMR (500 MHz, CDCl₃-d) δ ppm 10.62 (br. s, 1H) 7.91 (d, 8.3 Hz, 1H) 7.59 (d, J=1.4 Hz, 1H) 7.41 (dd, J=8.3, 1.4 Hz, 1H) 1.73 (d, J=1.1 Hz, 3H) 1.68 (d, J=1.1 Hz, 3H); TOF ES– MS: (M–H) 271.01; HPLC Ret: 7.15 min.

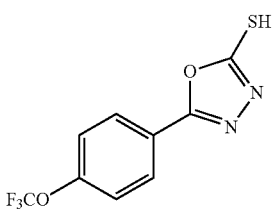

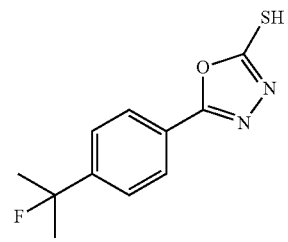

5-(4-(Trifluoromethoxy)phenyl)-1,3,4-oxadiazole-2-thiol

¹H NMR (500 MHz, CDCl₃-d) δ ppm 10.48 (br. s, 1H) 7.99 (d, J=9.0 Hz, 2H) 7.37 (d, J=9.0 Hz, 2H); TOF ES-MS: (M–H) 260.99; HPLC Ret: 7.05 min.

5-(4-(2-Fluoropropan-2-yl)phenyl)-1,3,4-oxadiazole-2-thiol

¹H NMR (500 MHz, CDCl₃-d) δ ppm 10.38 (br. s, 1H) 7.93 (d, J=8.8 Hz, 2H) 7.53 (d, J=8.8 Hz, 2H) 1.73 (d, J=0.8 Hz, 3H) 1.69 (d, J=0.8 Hz, 3H); TOF ES– MS: (M–H) 237.05; HPLC Ret: 6.87 min.

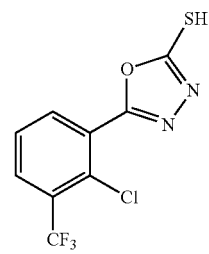 [SMILES: FC(F)(F)c1cccc(-c2nnc(S)o2)c1Cl]

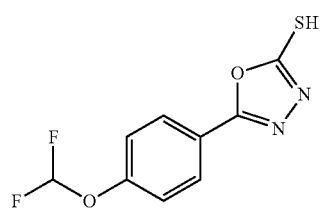 [SMILES: FC(F)Oc1ccc(-c2nnc(S)o2)cc1]

5-(4-(Difluoromethoxy)phenyl)-1,3,4-oxadiazole-2-thiol

¹H NMR (500 MHz, CDCl₃-d) δ ppm 10.59 (br. s, 1H) 7.96 (d, J=8.7 Hz, 2H) 7.26 (d, J=8.8 Hz, 2H) 6.61 (t, J=72.7 Hz, 1H); TOF ES– MS: (M–H) 243.00; HPLC Ret: 6.47 min.

Preparation 13: Synthesis of Methyl 4-((5-(2-chloro-4-cyclopropylphenyl)-1,3,4-oxadiazol-2-yl)thio)butanoate (A10)

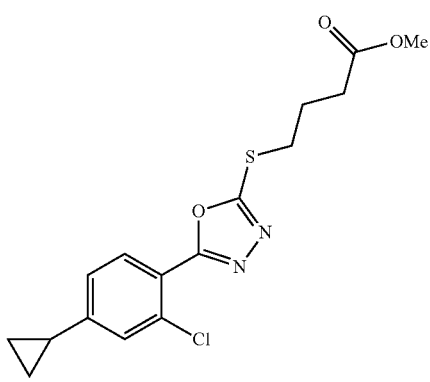 [SMILES: COC(=O)CCCSc1nnc(-c2ccc(C3CC3)cc2Cl)o1]

5-(2-chloro-4-cyclopropylphenyl)-1,3,4-oxadiazole-2-thiol (0.08 g, 0.33 mmol), acetone (2.0 mL), and potassium carbonate (0.06 g, 0.40 mmol) were combined in a 25 mL round-bottomed flask. methyl-4-bromobutanoate (0.07 g, 0.06 mL, 0.40 mmol) was added to the solution and the reaction was stirred 25° C. for 6 hr. The crude mixture was concentrated in vacuo, and the residue was partitioned between DCM (15 mL) and water (10 mL). The product was extracted with DCM (3×15 mL), washed with brine (30 mL), dried with magnesium sulfate, and concentrated in vacuo. The oil was subjected to silica gel chromatography eluting with 20% EtOAc: 80% Hex. The fractions containing product were concentrated to produce cloudy oil. Yield=64%. ¹H NMR (500 MHz, CDCl₃-d) δ ppm 7.81 (d, J=8.2 Hz, 1H) 7.19 (s, 1H) 7.05 (dd, J=8.2, 1.7 Hz, 1H) 3.69 (s, 3H) 2.37 (t, J=7.2 Hz, 2H) 2.58 (t, J=7.1 Hz, 2H) 2.20 (p, J=7.2 Hz, 2H) 1.96-1.91 (tt, J=8.4, 5.0 Hz, 1H) 1.08 (dt, J=6.9, 4.9 Hz, 2H) 0.78 (dt, J=6.9, 4.9 Hz, 2H); TOF ES+ MS: (M+H) 353.0; HPLC Ret: 8.01 min; 94% pure.

Other derivatives were made in an analogous fashion:

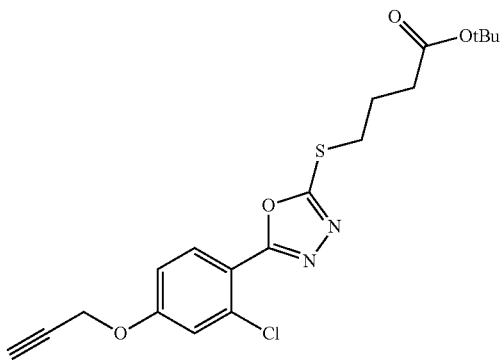 [SMILES: C#CCOc1ccc(-c2nnc(SCCCC(=O)OC(C)(C)C)o2)c(Cl)c1]

t-Butyl-4-((5-(2-chloro-4-(prop-2-yn-1-yloxy)phenyl)-1,3,4-oxadiazol-2-yl)thio)butanoate

* tert-butyl-4-bromobutanoate used as alkylating agent. Column: 20% EtOAc: 80% Hex. ¹H NMR (500 MHz, CDCl₃-d) δ ppm 7.90 (d, 8.8 Hz, 1H) 7.14 (d, J=2.5 Hz, 1H) 7.00 (dd, J=8.8, 2.6 Hz, 1H) 4.76 (d, J=2.4 Hz, 2H) 3.34 (t, J=7.2 Hz, 2H) 2.59 (t, J=2.4 Hz, 1H) 2.43 (t, J=7.2 Hz, 2H) 2.15 (p, J=7.2 Hz, 2H) 1.45 (s, 9H); TOF ES⁺ MS: (M+H) 409.9; HPLC Ret: 8.35 min.

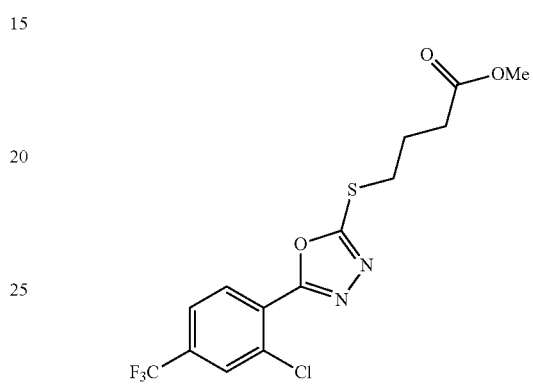

Methyl 4-((5-(2-chloro-4-(trifluoromethyl)phenyl)-1,3,4-oxadiazol-2-yl)thio)butanoate Column: 20% EtOAc: 80% Hex. HPLC Ret: 7.98 min.

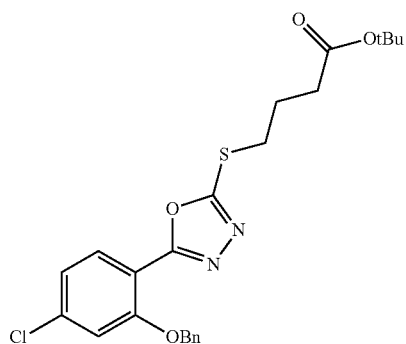 [SMILES: CC(C)(C)OC(=O)CCCSc1nnc(-c2ccc(Cl)cc2OCc2ccccc2)o1]

t-Butyl-4-((5-(2-(benzyl oxy)-4-chlorophenyl)-1,3,4-oxadiazol-2-yl)thio)butanoate

* tert-butyl-4-bromobutanoate used as alkylating agent. Column: 10% EtOAc: 90% Hex. ¹H NMR (500 MHz, CDCl₃-d) δ ppm 7.89 (d, J=8.3 Hz, 1H) 7.54-7.47 (m, 2H) 7.41 (t, J=7.5 Hz, 2H) 7.40-7.29 (m, 1H) 7.12-7.04 (m, 2H) 5.21 (s, 2H) 3.27 (t, J=7.1 Hz, 2H) 2.38 (t, J=7.2 Hz, 2H) 2.08 (p, J=7.4 Hz, 2H) 1.45 (s, 9H); TOF ES+ MS: (M+H) 461.1; HPLC Ret: 9.49 min.

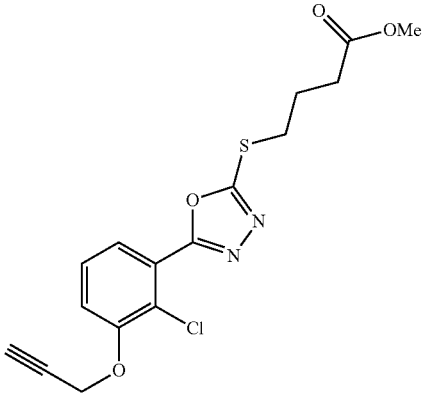 [SMILES: C#CCOc1cccc(-c2nnc(SCCCC(=O)OC)o2)c1Cl]

Methyl 4-((5-(2-chloro-3-(prop-2-yn-1-yloxy)phenyl)-1,3,4-oxadiazol-2-yl)thio)butanoate ¹H NMR (500 MHz, CDCl₃-d) δ ppm 7.58 (d, 8.4 Hz, 1H) 7.37 (d, J=1.9 Hz, 1H) 7.27 (dd, J=8.4, 1.9 Hz, 1H) 4.84 (d, J=2.4 Hz, 2H) 3.69 (s, 3H) 3.36 (t, J=7.2 Hz, 2H) 2.60 (t, J=2.4 Hz, 1H) 2.55 (t, J=7.2 Hz, 2H) 2.22 (p, J=7.2 Hz, 2H); TOF ES⁺ MS: (M+H) 367.1; HPLC Ret: 7.09 min.

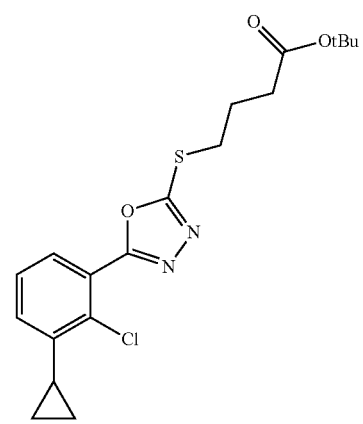 [SMILES: CC(C)(C)OC(=O)CCCSc1nnc(-c2cccc(C3CC3)c2Cl)o1]

tert-Butyl 4-((5-(2-chloro-3-cyclopropylphenyl)-1,3,4-oxadiazol-2-yl)thio)butanoate

* tert-butyl-4-bromobutanoate used as alkylating agent. Column: 5% EtOAc: 95% Hex. ¹H NMR (500 MHz, CDCl₃-d) δ ppm 7.69 (dd, J=7.7, 1.6 Hz, 1H) 7.29 (t, J=7.8 Hz, 1H) 7.15 (dd, J=7.9, 1.6 Hz, 1H) 3.35 (t, J=7.2 Hz, 2H) 2.43 (t, J=7.2 Hz, 2H) 2.26 (tt, J=8.6, 5.4 Hz, 1H) 2.16 (p, J=7.2 Hz, 2H) 1.46 (s, 9H) 1.13-1.02 (m, 2H) 0.77-0.66 (m, 2H); TOF ES+ MS: (M+H) 395.1; HPLC Ret: 9.19 min.

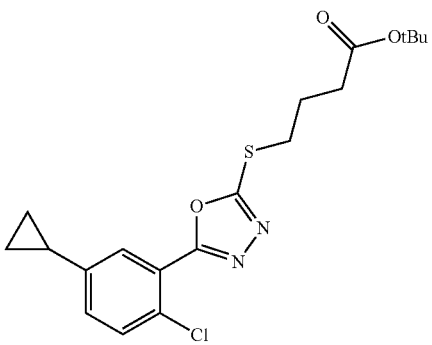 [SMILES: CC(C)(C)OC(=O)CCCSc1nnc(-c2cc(C3CC3)ccc2Cl)o1]

tert-Butyl 4-((5-(2-chloro-5-cyclopropylphenyl)-1,3,4-oxadiazol-2-yl)thio)butanoate

* tert-butyl-4-bromobutanoate used as alkylating agent. Column: 5% EtOAc: 95% Hex. ¹H NMR (500 MHz, CDCl₃-d) δ ppm 7.63 (d, J=2.3 Hz, 1H) 7.39 (d, J=8.4 Hz, 1H) 7.14 (dd, J=8.3, 2.3 Hz, 1H) 3.35 (t, J=7.2 Hz, 2H) 2.43 (t, J=7.2 Hz, 2H) 2.16 (p, J=7.2 Hz, 2H) 1.93 (ddd, J=13.5, 8.6, 5.1 Hz, 1H) 1.45 (s, 9H) 1.07-0.98 (m, 2H) 0.75-0.64 (m, 2H); TOF ES+ MS: (M+H) 395.1; HPLC Ret: 9.21 min.

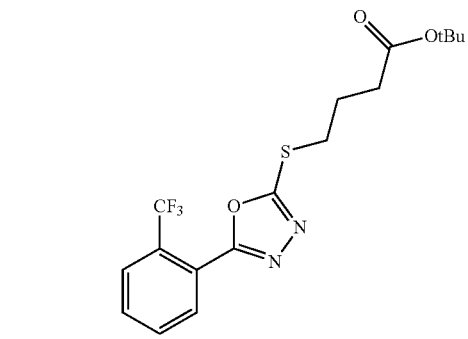 [SMILES: CC(C)(C)OC(=O)CCCSc1nnc(-c2ccccc2C(F)(F)F)o1]

tert-Butyl 4-((5-(2-(trifluoromethyl)phenyl)-1,3,4-oxadiazol-2-yl)thio)butanoate

* tert-butyl-4-bromobutanoate used as alkylating agent. Column: 15% EtOAc: 75% Hex. ¹H NMR (500 MHz, CDCl₃-d) δ ppm 8.06-8.00 (m, 1H) 7.85 (dd, J=7.1, 1.9 Hz, 1H) 7.74-7.64 (m, 2H) 3.34 (t, J=7.2 Hz, 2H) 2.43 (t, J=7.2 Hz, 2H) 2.15 (p, J=7.2 Hz, 2H) 1.45 (s, 9H); TOF ES+ MS: (M+H) 389.1; HPLC Ret: 8.46 min.

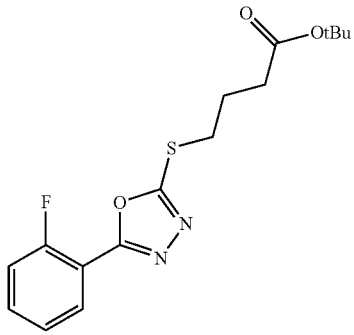 [SMILES: CC(C)(C)OC(=O)CCCSc1nnc(-c2ccccc2F)o1]

tert-Butyl 4-((5-(2-fluorophenyl)-1,3,4-oxadiazol-2-yl)thio)butanoate

* tert-butyl-4-bromobutanoate used as alkylating agent. Column: 15% EtOAc: 75% Hex. ¹H NMR (500 MHz, CDCl₃-d) δ ppm 8.02 (td, J=7.5, 1.8 Hz, 1H) 7.56-7.48 (m, 1H) 7.32-7.20 (m, 2H) 3.36 (t, J=7.2 Hz, 2H) 2.43 (t, J=7.2 Hz, 2H) 2.15 (p, J=7.2 Hz, 2H) 1.46 (s, 9H); TOF ES+ MS: (M+H) 339.1; HPLC Ret: 8.08 min.

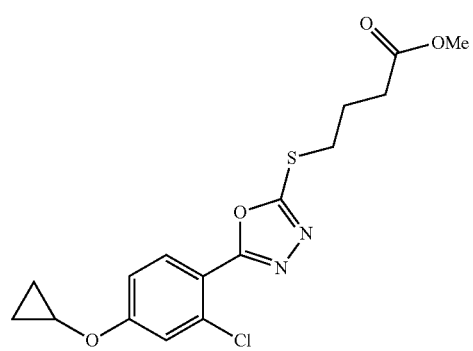 [SMILES: COC(=O)CCCSc1nnc(-c2ccc(OC3CC3)cc2Cl)o1]

Methyl 4-((5-(2-chloro-4-cyclopropoxyphenyl)-1,3,4-oxadiazol-2-yl)thio)butanoate Column: 20% EtOAc: 80% Hex. ¹H NMR (500 MHz, CDCl₃-d) δ ppm 7.86 (d, 8.8 Hz, 1H) 7.24 (d, J=2.5 Hz, 1H) 7.04 (dd, J=8.8, 2.5 Hz, 1H) 3.83-3.76 (m, 1H) 3.69 (s, 3H) 3.35 (t, J=7.2 Hz, 2H) 2.53 (t, J=7.2 Hz, 2H) 2.20 (p, J=7.2 Hz, 2H) 0.90-0.78 (m, 4H); TOF ES⁺ MS: (M+H) 368.06; HPLC Ret: 7.94 min.

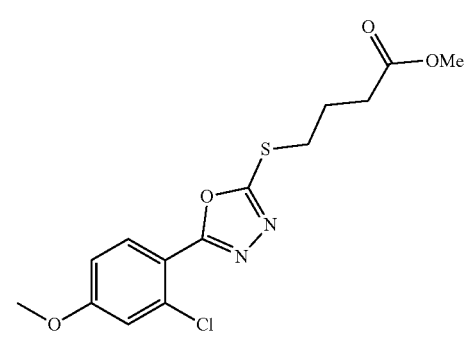 [SMILES: COC(=O)CCCSc1nnc(-c2ccc(OC)cc2Cl)o1]

Methyl 4-((5-(2-chloro-4-methoxyphenyl)-1,3,4-oxadiazol-2-yl)thio)butanoate

Column: 25% EtOAc: 75% Hex to 45% EtOAc: 55% Hex. ¹H NMR (500 MHz, CDCl₃-d) δ ppm 7.88 (d, 8.8 Hz, 1H) 7.05 (d, J=2.5 Hz, 1H) 6.92 (dd, J=8.8, 2.5 Hz, 1H) 3.87 (s, 3H) 3.69 (s, 3H) 3.35 (t, J=7.2 Hz, 2H) 2.53 (t, J=7.2 Hz, 2H) 2.20 (p, J=7.2 Hz, 2H); TOF ES⁺ MS: (M+H) 343.05; HPLC Ret: 7.31 min.

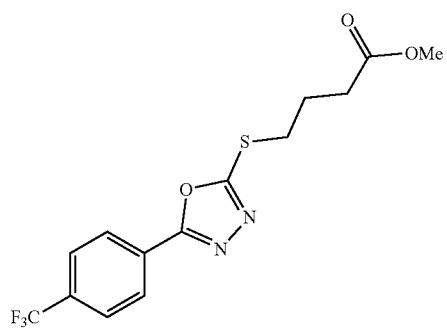 [SMILES: COC(=O)CCCSc1nnc(-c2ccc(C(F)(F)F)cc2)o1]

Methyl 4-((5-(4-(trifluoromethyl)phenyl)-1,3,4-oxadiazol-2-yl)thio)butanoate (DJK-6-97). Column: 15% EtOAc: 75% Hex to 20% EtOAc: 80% Hex. ¹H NMR (500 MHz, CDCl₃-d) δ ppm 8.14 (d, J=8.2 Hz, 2H) 7.77 (d, J=8.2 Hz, 2H) 3.70 (s, 3H) 3.39 (t, J=7.2 Hz, 2H) 2.54 (t, J=7.1 Hz, 2H) 2.22 (p, J=7.1 Hz, 2H); TOF ES⁺ MS: (M+H) 347.07; HPLC Ret: 7.75 min.

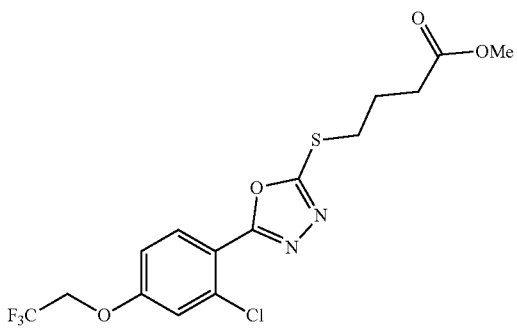 [SMILES: COC(=O)CCCSc1nnc(-c2ccc(OCC(F)(F)F)cc2Cl)o1]

Methyl 4-((5-(2-chloro-4-(2,2,2-trifluoroethoxy)phenyl)-1,3,4-oxadiazol-2-yl)thio)butanoate Column: 25% EtOAc: 75% Hex to 30% EtOAc: 70% Hex. ¹H NMR (500 MHz, CDCl₃-d) δ ppm 7.94 (d, J=8.8 Hz, 1H) 7.12 (d, J=1.1 Hz, 1H) 6.98 (dd, J=8.8, 1.1 Hz, 1H) 4.42 (q, J=8.5 Hz, 2H) 3.70 (s, 3H) 3.36 (t, J=7.1 Hz, 2H) 2.53 (t, J=7.1 Hz, 2H) 2.21 (p, J=7.0 Hz, 2H); TOF ES⁺ MS: (M+H) 411.04; HPLC Ret: 7.78 min.

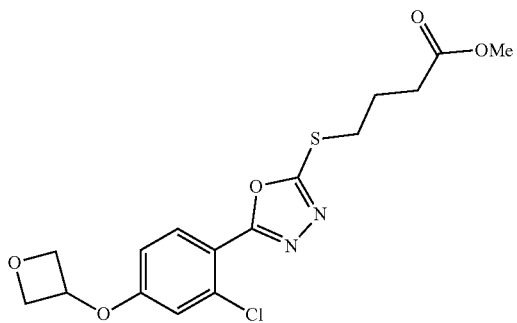 [SMILES: COC(=O)CCCSc1nnc(-c2ccc(OC3COC3)cc2Cl)o1]

Methyl 4-((5-(2-chloro-4-(oxetan-3-yloxy)phenyl)-1,3,4-oxadiazol-2-yl)thio)butanoate Column: 40% EtOAc: 60% Hex to 80% EtOAc: 20% Hex. $^1$H NMR (500 MHz, CDCl$_3$-d) δ ppm 7.88 (d, 8.8 Hz, 1H) 6.85 (d, J=2.6 Hz, 1H) 6.73 (dd, J=8.8, 2.6 Hz, 1H) 5.26 (pd, 6.0, 1.0 Hz, 1H) 5.01 (t, J=7.1 Hz, 2H) 4.77 (dd, J=7.3, 5.1 Hz, 2H) 3.69 (s, 3H) 3.35 (t, J=7.2 Hz, 2H) 2.53 (t, J=7.2 Hz, 2H) 2.20 (p, J=7.2 Hz, 2H); TOF ES+ MS: (M+H) 285.06; HPLC Ret: 6.03 min.

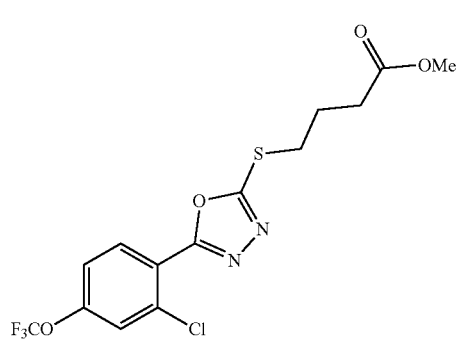

Methyl 4-((5-(2-chloro-4-(trifluoromethoxy)phenyl)-1,3,4-oxadiazol-2-yl)thio)butanoate Column: 15% EtOAc: 85% Hex. $^1$H NMR (500 MHz, CDCl$_3$-d) δ ppm 8.02 (d, J=8.7 Hz, 1H) 7.42 (d, J=2.1 Hz, 1H) 7.27 (dd, J=8.8, 2.1 Hz, 1H) 3.70 (s, 3H) 3.37 (t, J=7.1 Hz, 2H) 2.53 (t, J=7.2 Hz, 2H) 2.22 (p, J=7.2 Hz, 2H); TOF ES$^+$ MS: (M+H) 397.02; HPLC Ret: 8.15 min.

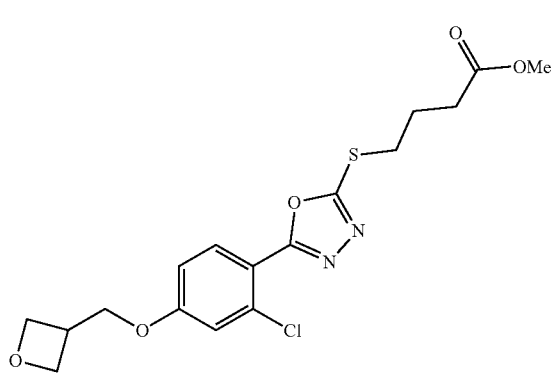 [SMILES: COC(=O)CCCSc1nnc(-c2ccc(OCC3COC3)cc2Cl)o1]

Methyl 4-((5-(2-chloro-4-(oxetan-3-ylmethoxy)phenyl)-1,3,4-oxadiazol-2-yl)thio)butanoate Column: 60% EtOAc: 40% Hex to 80% EtOAc: 20% Hex. $^1$H NMR (500 MHz, CDCl$_3$-d) δ ppm 7.89 (d, 8.8 Hz, 1H) 7.08 (d, J=2.6 Hz, 1H) 6.93 (dd, J=8.8, 2.6 Hz, 1H) 4.90 (dd, J=7.7, 6.4 Hz, 2H) 4.57 (t, J=6.0 Hz, 2H) 4.26 (dd, J=6.6, 1.1 Hz, 2H) 3.69 (s, 3H) 3.47 (hept., 7.2 Hz, 1H) 3.35 (t, J=7.2 Hz, 2H) 2.53 (t, J=7.2 Hz, 2H) 2.21 (p, J=7.2 Hz, 2H); TOF ES+ MS: (M+H) 399.08; HPLC Ret: 6.78 min.

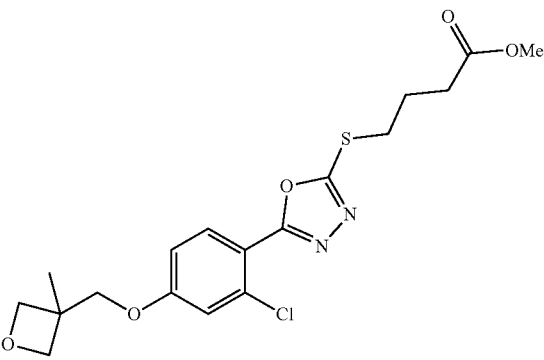 [SMILES: COC(=O)CCCSc1nnc(-c2ccc(OCC3(C)COC3)cc2Cl)o1]

Methyl 4-((5-(2-chloro-4-((3-methyloxetan-3-yl)methoxy)phenyl)-1,3,4-oxadiazol-2-yl)thio)butanoate Column: 70% EtOAc: 30% Hex. $^1$H NMR (500 MHz, CDCl$_3$-d) δ ppm 7.90 (d, 8.8 Hz, 1H) 7.10 (d, J=2.6 Hz, 1H) 6.96 (dd, J=8.8, 2.5 Hz, 1H) 4.64 (d, J=6.1 Hz, 2H) 4.48 (d, J=6.1 Hz, 2H) 4.10 (s, 2H) 3.70 (s, 3H) 3.36 (t, J=7.1 Hz, 2H) 2.53 (t, J=7.1 Hz, 2H) 2.22 (p, J=7.1 Hz, 2H) 1.46 (s, 3H); TOF ES+ MS: (M+H) 413.10; HPLC Ret: 7.25 min.

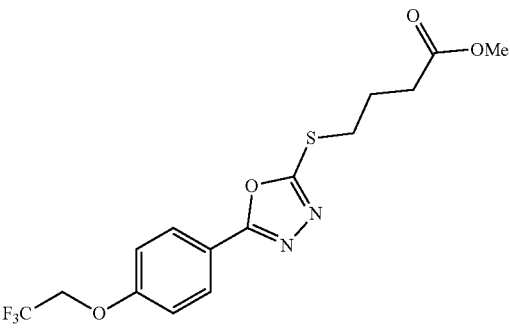 [SMILES: COC(=O)CCCSc1nnc(-c2ccc(OCC(F)(F)F)cc2)o1]

Methyl 4-((5-(4-(2,2,2-trifluoroethoxy)phenyl)-1,3,4-oxadiazol-2-yl)thio)butanoate Column: 30% EtOAc: 70% Hex to 40% EtOAc: 60% Hex. $^1$H NMR (500 MHz, CDCl$_3$-d) δ ppm 7.98 (d, J=8.0 Hz, 2H) 7.05 (d, J=8.0 Hz, 2H) 4.42 (q, J=8.0 Hz, 2H) 3.69 (s, 3H) 3.35 (t, J=7.1 Hz, 2H) 2.53 (t, J=7.2 Hz, 2H) 2.20 (p, J=7.2 Hz, 2H); TOF ES' MS: (M+H) 377.08; HPLC Ret: 7.48 min.

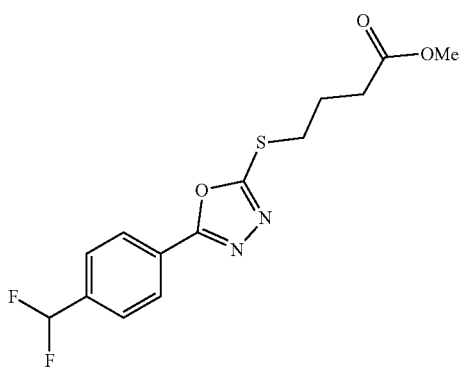 [SMILES: COC(=O)CCCSc1nnc(-c2ccc(C(F)F)cc2)o1]

Methyl 4-((5-(4-(difluoromethyl)phenyl)-1,3,4-oxadiazol-2-yl)thio)butanoate (DJK-7-4). Column: 30% EtOAc: 70% Hex to 35% EtOAc: 65% Hex. $^1$H NMR (500 MHz, CDCl$_3$-d) δ ppm 8.11 (d, J=8.0 Hz, 2H) 7.65 (d, J=8.0 Hz, 2H) 6.70 (t, J=56.2 Hz, 1H) 3.70 (s, 3H) 3.38 (t, J=7.2 Hz, 2H) 2.54 (t, J=7.2 Hz, 2H) 2.22 (p, J=7.2 Hz, 2H); TOF ES$^+$ MS: (M+H) 329.08; HPLC Ret: 7.14 min.

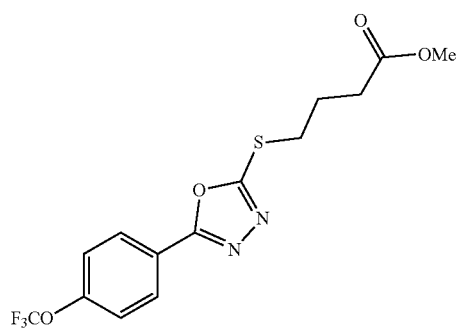 [SMILES: COC(=O)CCCSc1nnc(-c2ccc(OC(F)(F)F)cc2)o1]

Methyl 4-((5-(4-(trifluoromethoxy)phenyl)-1,3,4-oxadiazol-2-yl)thio)butanoate Column: 15% EtOAc: 85% Hex to 25% EtOAc: 75% Hex. $^1$H NMR (500 MHz, CDCl$_3$-d) δ ppm 8.06 (d, J=8.1 Hz, 2H) 7.34 (d, J=8.1 Hz, 2H) 3.70 (s, 3H) 3.37 (t, J=7.2 Hz, 2H) 2.53 (t, J=7.2 Hz, 2H) 2.21 (p, J=7.2 Hz, 2H); TOF ES$^+$ MS: (M+H) 363.06; HPLC Ret: 7.85 min.

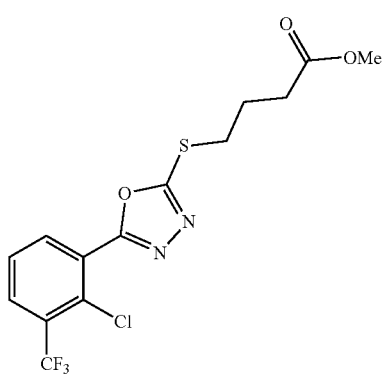 [SMILES: COC(=O)CCCSc1nnc(-c2cccc(C(F)(F)F)c2Cl)o1]

Methyl 4-((5-(2-chloro-3-(trifluoromethyl)phenyl)-1,3,4-oxadiazol-2-yl)thio)butanoate Column: 30% EtOAc: 70% Hex to 35% EtOAc: 65% Hex. $^1$H NMR (500 MHz, CDCl$_3$-d) δ ppm 8.10 (d, J=7.9 Hz, 1H) 7.89 (d, J=7.9 Hz, 1H) 7.53 (t, J=8.0 Hz, 1H) 3.70 (s, 3H) 3.39 (t, J=7.1 Hz, 2H) 2.54 (t, J=7.2 Hz, 2H) 2.22 (p, J=7.1 Hz, 2H); TOF ES$^+$ MS: (M+H) 381.03; HPLC Ret: 7.81 min.

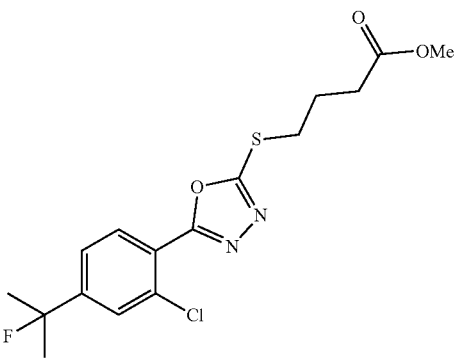 [SMILES: COC(=O)CCCSc1nnc(-c2ccc(C(C)(C)F)cc2Cl)o1]

Methyl 4-((5-(2-chloro-4-(2-fluoropropan-2-yl)phenyl)-1,3,4-oxadiazol-2-yl)thio)butanoate Column: 25% EtOAc: 75% Hex to 35% EtOAc: 65% Hex. $^1$H NMR (500 MHz, CDCl$_3$-d) δ ppm 7.94 (d, J=8.2 Hz, 1H) 7.56 (d, J=1.7 Hz, 1H) 7.38 (dd, J=8.3, 1.8 Hz, 1H) 3.70 (s, 3H) 3.37 (t, J=7.1 Hz, 2H) 2.54 (t, J=7.2 Hz, 2H) 2.22 (p, J=7.2 Hz, 2H) 1.72 (s, 3H) 1.68 (s, 3H); TOF ES' MS: (M+H) 373.08; HPLC Ret: 7.96 min.

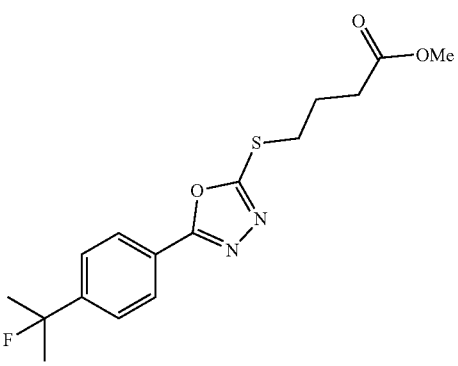 [SMILES: COC(=O)CCCSc1nnc(-c2ccc(C(C)(C)F)cc2)o1]

Methyl 4-((5-(4-(2-fluoropropan-2-yl)phenyl)-1,3,4-oxadiazol-2-yl)thio)butanoate Column: 25% EtOAc: 75% Hex to 35% EtOAc: 65% Hex. $^1$H NMR (500 MHz, CDCl$_3$-d) δ ppm 8.00 (d, J=8.1 Hz, 2H) 7.51 (d, J=8.2 Hz, 2H) 3.70 (s, 3H) 3.37 (t, J=7.2 Hz, 2H) 2.54 (t, J=7.2 Hz, 2H) 2.22 (p, J=7.2 Hz, 2H) 1.74 (s, 3H) 1.69 (s, 3H); TOF ES$^+$ MS: (M+H) 339.12; HPLC Ret: 7.65 min.

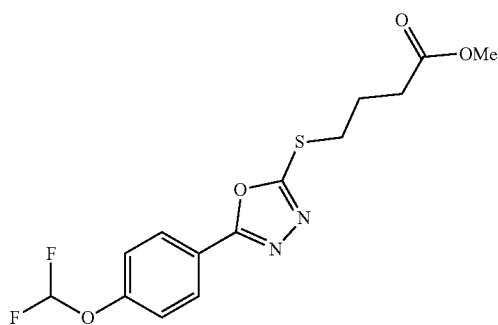 [SMILES: COC(=O)CCCSc1nnc(-c2ccc(OC(F)F)cc2)o1]

Methyl 4-((5-(4-(difluoromethoxy)phenyl)-1,3,4-oxadiazol-2-yl)thio)butanoate

Column: 30% EtOAc: 70% Hex to 35% EtOAc: 65% Hex. ¹H NMR (500 MHz, CDCl₃-d) δ ppm 8.02 (d, J=8.8 Hz, 2H) 7.25 (d, J=8.8 Hz, 2H) 6.59 (t, J=73.1 Hz, 1H) 3.69 (s, 3H) 3.36 (t, J=7.2 Hz, 2H) 2.53 (t, J=7.2 Hz, 2H) 2.20 (p, J=7.2 Hz, 2H); TOF ES⁺ MS: (M+H) 345.07; HPLC Ret: 7.20 min.

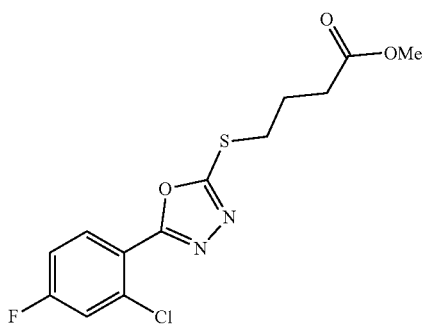 [SMILES: COC(=O)CCCSc1nnc(-c2ccc(F)cc2Cl)o1]

Methyl 4-((5-(2-chloro-4-fluorophenyl)-1,3,4-oxadiazol-2-yl)thio)butanoate

Column: 25% EtOAc: 75% Hex. ¹H NMR (500 MHz, CDCl₃-d) δ ppm 7.96 (ddd, J=9.4, 6.1, 3.3 Hz, 1H) 7.29 (dt, J=8.5, 2.8 Hz, 1H) 7.13 (dd, J=8.8, 2.1 Hz, 1H) 3.69 (s, 3H) 3.36 (t, J=7.1 Hz, 2H) 2.53 (t, J=7.2 Hz, 2H) 2.21 (p, J=7.2 Hz, 2H); TOF ES' MS: (M+H) 331.03; HPLC Ret: 7.30 min.

Preparation 14: trans-methyl 3-((5-(2,4-dichlorophenyl)-1,3,4-oxadiazol-2-yl)thio)cyclobutanecarboxylate & cis-methyl 3-((5-(2,4-dichlorophenyl)-1,3,4-oxadiazol-2-yl)thio)cyclobutanecarboxylate

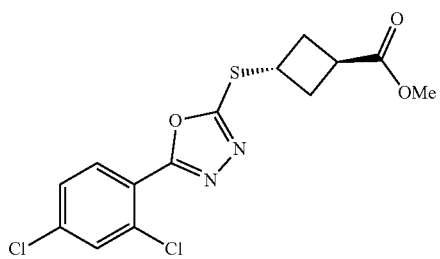

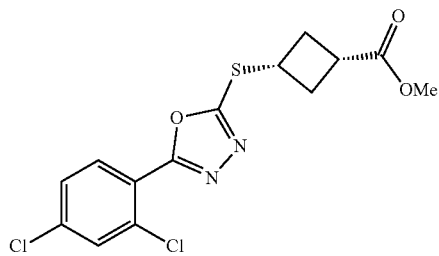

5-(2,4-dichlorophenyl)-1,3,4-oxadiazole-2-thiol (0.1 g, 0.41 mmol), cesium carbonate (0.17 g, 0.51 mmol), and sodium iodide (0.006 g, 0.04 mmol) were dissolved in 2 mL DMSO. Methyl 3-chlorocyclobutanecarboxylate (0.09 g, 0.61 mmol, 0.08 mL) was added and the mixture was stirred at 100° C. for 40 hr. The reaction was diluted with EtOAc and H₂O, and product was extracted with EtOAc (3×15 mL). The organic layers were combined, washed with brine (2×15 mL), and evaporated in vacuo. The oil was subjected to silica gel chromatography eluting with 15% EtOAc: 75% Hex. The diastereomers were separated and fractions containing products were concentrated. Trans: ¹H NMR (500 MHz, CDCl₃-d) δ ppm 7.91 (d, J=8.5 Hz, 1H) 7.57 (d, J=2.0 Hz, 1H) 7.39 (dd, J=8.5, 2.0 Hz, 1H) 4.48-4.38 (m, 1H) 3.73 (s, 3H) 3.40 (tt, J=10.4, 5.7 Hz, 1H) 2.94 (tt, J=8.4, 5.8 Hz, 2H) 2.56 (dtd, J=13.3, 6.4, 2.4 Hz, 2H); ¹³C NMR (500 MHz, CDCl₃-d) δ ppm 174.87, 164.01, 163.34, 138.08, 133.74, 131.58, 131.19, 127.61, 121.39, 52.07, 37.62, 35.22, 32.73; TOF ES+ MS: (M+H) 359.0; HPLC Ret: 8.02 min. cis: ¹H NMR (500 MHz, CDCl₃-d) δ ppm 7.90 (d, J=8.5 Hz, 1H) 7.57 (d, J=2.0 Hz, 1H) 7.39 (dd, J=8.5, 2.0 Hz, 1H) 4.30 (p, J=8.6 Hz, 1H) 3.71 (s, 3H) 3.17 (p=8.9 Hz, 1H) 2.95-2.85 (m, 2H) 2.55 (qd, J=9.7, 2.9 Hz, 2H); ¹³C NMR (500 MHz, CDCl₃-d) δ ppm 173.80, 164.17, 163.30, 138.03, 133.72, 131.57, 131.16, 127.59, 121.39, 52.02, 35.45, 34.45, 33.77; TOF ES+ MS: (M+H) 359.0; HPLC Ret: 7.89 min.

Other derivatives were made in an analogous fashion:

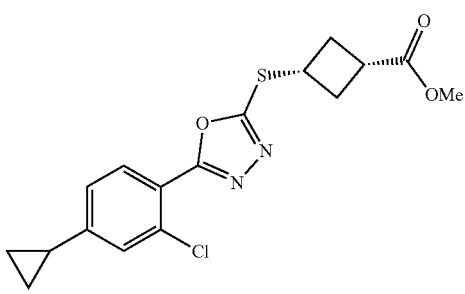

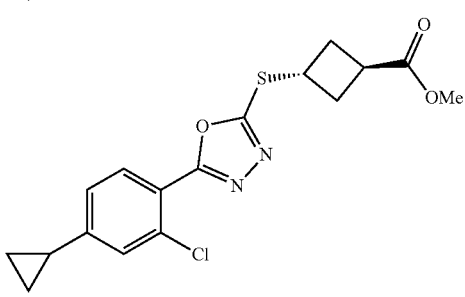

cis-methyl 3-((5-(2-chloro-4-cyclopropylphenyl)-1,3,4-oxadiazol-2-yl)thio)cyclobutanecarboxylate & trans-methyl 3-((5-(2-chloro-4-cyclopropylphenyl)-1,3,4-oxadiazol-2-yl)thio)cyclobutanecarboxylate Column: 15% EtOAc: 75% Hex. cis: ¹H NMR (500 MHz, CDCl₃-d) δ ppm 7.81 (d, J=8.2 Hz, 1H) 7.20 (d, J=1.7 Hz, 1H) 7.05 (dd, J=8.2, 1.7 Hz, 1H) 4.35-4.23 (m, 1H) 3.71 (s, 3H) 3.23-3.11 (m, 1H) 2.98-2.84 (m, 2H) 2.61-2.49 (m, 2H) 1.98-1.87 (m, 1H) 1.09 (tdd, J=6.6, 5.6, 3.8 Hz, 2H) 0.79 (tdd, J=6.4, 4.8, 2.5 Hz, 2H); TOF ES+ MS: (M+H) 365.1; HPLC Ret: 8.26 min. trans: ¹H NMR (500 MHz, CDCl₃-d) δ ppm 7.82 (d, J=7.8 Hz, 1H) 7.20 (d, J=1.8 Hz, 1H) 7.05 (dd, J=7.4, 2.0 Hz, 1H) 4.41 (tddd, J=10.0, 8.5, 5.9, 2.2 Hz, 1H) 3.73 (s, 3H) 3.45-3.34 (m, 1H) 2.99-2.90 (m, 2H) 2.60-2.50 (m, 2H) 1.97-1.87 (m, 1H) 1.09 (tdd, J=6.6, 3.8, 2.0 Hz, 2H) 0.79 (tdd, J=6.5, 4.9, 2.4 Hz, 2H); TOF ES+ MS: (M+H) 365.1; HPLC Ret: 8.40 min.

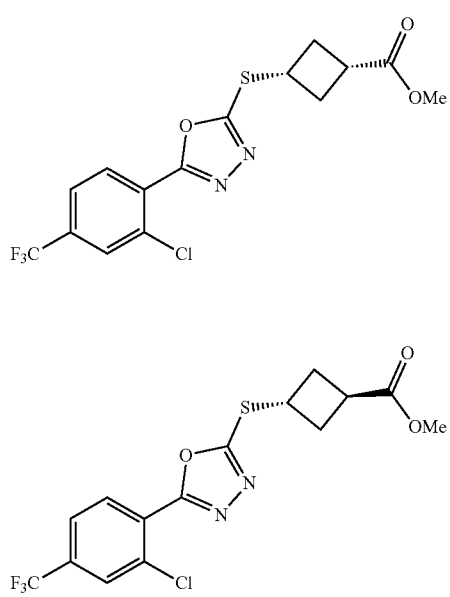

cis-methyl 3-((5-(2-chloro-4-(trifluoromethyl)phenyl)-1,3,4-oxadiazol-2-yl)thio)cyclobutanecarboxylate & trans-methyl 3-((5-(2-chloro-4-(trifluoromethyl)phenyl)-1,3,4-oxadiazol-2-yl)thio)cyclobutanecarboxylate Column: 15% EtOAc: 75% Hex. cis-isomer yield=34% & trans-isomer yield=18%. cis: ¹H NMR (500 MHz, CDCl₃-d) δ ppm 8.11 (d, J=8.2 Hz, 1H) 7.80 (d, J=1.7 Hz, 1H) 7.66 (dd, J=8.5, 1.8 Hz, 1H) 4.33 (td, J=7.7, 1.5 Hz, 1H) 3.71 (s, 3H) 3.25-3.13 (m, 1H) 3.02-2.81 (m, 2H) 2.62-2.50 (m, 2H); NOSEY attached; TOF ES+ MS: (M+H) 393.0; HPLC Ret: 8.21 min. trans: ¹H NMR (500 MHz, CDCl₃-d) δ ppm 8.12 (d, J=8.2 Hz, 1H) 7.82 (d, J=1.7 Hz, 1H) 7.67 (dd, J=8.7, 1.8 Hz, 1H) 4.51-4.41 (m, 1H) 3.74 (s, 3H) 3.45-3.37 (m, 1H) 3.00-2.91 (m, 2H) 2.62-2.51 (m, 2H); NOSEY attached; TOF ES+ MS: (M+H) 393.0; HPLC Ret: 8.31 min.

Preparation 15: cis/trans-Methyl 3-hydroxycyclopentanecarboxylate

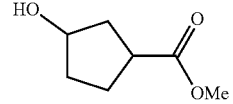

US20160151375

In a 25 mL round-bottomed flask, methyl 3-oxocyclopentanecarboxylate (0.25 g, 0.22 mL, 1.76 mmol) was dissolved in 5 mL MeOH and cooled to 0° C. NaBH₄ (0.07 g, 1.76 mmol) was added and the reaction was stirred at 0° C. for 1 hr. The reaction was quenched with 1 N HCl and the product was extracted with EtOAc (3×20 mL). The organic layers were combined, washed with brine (2×15 mL), and evaporated in ¹H NMR (500 MHz, CDCl₃-d) δ ppm 4.46 (tt, J=5.3, 2.7 Hz, 0.34H) 4.33 (tt, J=5.5, 3.0 Hz, 1H) 3.71 (s, 3H) 3.68 (s, 1.3H) 3.12-3.05 (m, 0.3H) 2.89 (tdd, J=9.2, 6.5, 4.5 Hz, 1H) 2.18-1.60 (m, 8H). 3:1 diastereomer ratio.

Preparation 16: cis/trans-methyl 3-((methylsulfonyl)oxy)cyclopentanecarboxylate

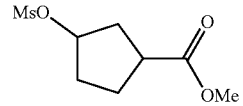

In a 25 mL round-bottomed flask, methyl 3-hydroxycyclopentanecarboxylate (0.22 g, 1.5 mmol) was dissolved in 2 mL DCM and cooled to 0° C. Et₃N (0.39 g, 0.54 mL, 3.9 mmol) was added followed by a slow addition of MsCl (0.2 g, 0.14 mL, 1.8 mmol). The solution was warmed to 25° C. and stirred for 2 hr. The reaction was quenched with sat. NaHCO₃ and extracted with DCM (3×20 mL). The organic layers were combined, washed with brine (2×15 mL), and concentrated in vacuo. ¹H NMR (500 MHz, CDCl₃-d) δ ppm 5.29-5.23 (m, 0.32H) 5.16 (tt, J=5.9, 4.0 Hz, 1H) 3.70 (s, 3H) 3.68 (s, 1.3H) 3.13-3.02 (m, 0.3H) 3.01 (s, 3H) 2.99 (s, 1.2H) 2.90-2.78 (m, 1H) 2.40-1.85 (m, 8H). 3:1 diastereomer ratio.

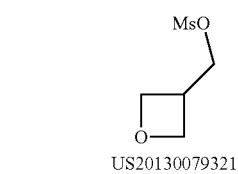

US20130079321

Oxetan-3-ylmethyl methanesulfonate

¹H NMR (500 MHz, CDCl₃-d) δ ppm 4.78-4.76 (m, 2H) 4.51-4.44 (m, 4H) 3.45-3.33 (m, 1H) 3.06 (s, 3H).

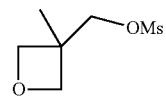

(3-Methyloxetan-3-yl)methyl methanesulfonate

<sup>1</sup>H NMR (500 MHz, CDCl<sub>3</sub>-d) δ ppm 4.52 (d, J=6.2 Hz, 2H) 4.43 (d, J=6.2 Hz, 2H) 4.32 (s, 2H) 3.07 (s, 3H) 1.40 (s, 3H).

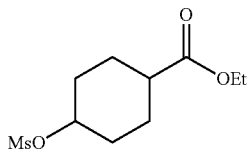 [SMILES: CCOC(=O)C1CCC(OS(C)(=O)=O)CC1]

cis/trans-ethyl 4-((methylsulfonyl)oxy)cyclohexanecarboxylate

<sup>1</sup>H NMR (500 MHz, CDCl<sub>3</sub>-d) δ ppm 4.97-4.90 (m, 0.5H) 4.69-4.61 (m, 0.5H) 4.14 (m, 2H) 3.17-3.07 (m, 1H) 3.03 (s, 1.5H) 2.99 (s, 1.5H) 2.43-2.28 (m, 1H) 2.23-1.90 (m, 4H) 1.84-1.56 (m, 5H) 1.44-1.40 (m, 1.5H) 1.29-1.23 (m, 3H). 1:1 diastereomer ratio.

cis-ethyl 4-((5-(2,4-dichlorophenyl)-1,3,4-oxadiazol-2-yl)thio)cyclohexanecarboxylate & trans-ethyl 4-((5-(2,4-dichlorophenyl)-1,3,4-oxadiazol-2-yl)thio)cyclohexanecarboxylate

*Sodium iodide not used and ethyl 4-((methylsulfonyl)oxy)cyclohexanecarboxylate used as alkylating agent. Column: 15% EtOAc: 85% Hex. cis-isomer yield=47% & trans-isomer yield=25%. cis: <sup>1</sup>H NMR (500 MHz, CDCl<sub>3</sub>-d) δ ppm 7.91 (d, J=8.5 Hz, 1H) 7.57 (d, J=1.9 Hz, 1H) 7.39 (dd, J=8.5, 1.9 Hz, 1H) 4.21-4.10 (m, 3H) 2.57-2.47 (m, 1H) 2.13-1.95 (m, 6H) 1.90-1.79 (m, 2H) 1.27 (t, J=7.2 Hz, 3H); <sup>13</sup>C NMR (500 MHz, CDCl<sub>3</sub>-d) δ ppm 174.62, 165.01, 163.15, 137.94, 133.70, 131.54, 131.14, 127.57, 121.47, 60.43, 45.63, 40.79, 30.17, 25.51, 14.23; TOF ES+ MS: (M+H) 373.02; TOF ES+ MS: (M+H) 401.05; HPLC Ret: 9.18 min. trans: <sup>1</sup>H NMR (500 MHz, CDCl<sub>3</sub>-d) δ ppm 7.92 (dd, J=8.5, 3.6 Hz, 1H) 7.57 (q, J=2.0 Hz, 1H) 7.39 (dq, J=8.5, 2.1 Hz, 1H) 4.14 (q, J=7.1 Hz, 2H) 3.78-3.68 (m, 1H) 2.42-2.31 (m, 3H) 2.18-2.09 (m, 2H) 1.69-1.55 (m, 4H) 1.26 (t, J=7.1 Hz, 3H); <sup>13</sup>C NMR (500 MHz, CDCl<sub>3</sub>-d) δ ppm 174.87, 164.44, 163.23, 138.00, 133.68, 131.56, 131.16, 127.59, 121.44, 60.43, 45.61, 42.04, 32.26, 28.71, 14.19; TOF ES+ MS: (M+H) 401.05; HPLC Ret: 9.33 min.

Preparation 17: cis-methyl 3-((5-(2,4-dichlorophenyl)-1,3,4-oxadiazol-2-yl)thio)cyclopentanecarboxylate trans-methyl 3-((5-(2,4-dichlorophenyl)-1,3,4-oxadiazol-2-yl)thio)cyclopentanecarboxylate

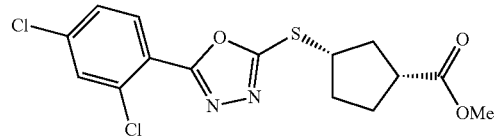

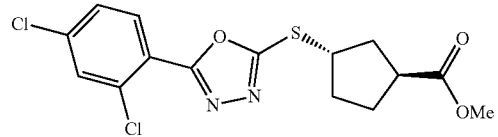

In a 50 mL round-bottomed flask, 5-(2,4-dichlorophenyl)-1,3,4-oxadiazole-2-thiol (0.2 g, 0.81 mmol) was dissolved in 2 mL THF. 95% NaH (0.07 g, 0.85 mmol) was added and the reaction proceeded at 25° C. for 30 min. methyl 3-((methylsulfonyl)oxy)cyclopentanecarboxylate (0.33 g, 1.50 mmol) in THF (2 mL) was added dropwise and the solution was stirred at 50° C. for 16 hr. The reaction was partitioned between sat. NaHCO<sub>3</sub> and EtOAc, and the product was extracted with EtOAc (3×20 mL). The organic layers were combined, dried with MgSO<sub>4</sub>, and concentrated in vacuo. The oil was subjected to silica gel chromatography eluting with 10% EtOAc: 90% Hex to 20% EtOAc: 80% Hex. The diastereomers were separated and fractions containing products were concentrated. cis: <sup>1</sup>H NMR (500 MHz, CDCl<sub>3</sub>-d) δ ppm 7.91 (d, J=8.4 Hz, 1H) 7.57 (d, J=2.1 Hz, 1H) 7.39 (dd, J=8.5, 2.1 Hz, 1H) 4.27-4.17 (m, 1H) 3.70 (s, 3H) 3.14-3.03 (m, 1H) 2.59-2.55 (m, 1H) 2.50-2.32 (m, 1H) 2.24-2.14 (m, 1H) 2.00-1.95 (m, 1H) 1.91-1.80 (m, 1H); <sup>13</sup>C NMR (500 MHz, CDCl<sub>3</sub>-d) δ ppm 175.58, 164.72, 163.24, 138.01, 133.70, 131.57, 131.55, 127.59, 121.41, 51.96, 45.56, 42.45, 37.02, 33.20, 28.84; TOF ES+ MS: (M+H) 373.02; HPLC Ret: 8.50 min. trans: <sup>1</sup>H NMR (500 MHz, CDCl<sub>3</sub>-d) δ ppm 7.86 (d, J=8.5 Hz, 1H) 7.58 (d, J=2.0 Hz, 1H) 7.41 (dd, J=8.6, 1.5 Hz, 1H) 5.30-5.24 (m, 1H) 3.72 (s, 3H) 3.22 (p, J=8.0 Hz, 1H) 2.49-2.42 (m, 1H) 2.38-2.10 (m, 3H) 2.12-1.92 (m, 2H); <sup>13</sup>C NMR (500 MHz, CDCl<sub>3</sub>-d) δ ppm 175.60, 175.08, 156.30, 138.59, 133.79, 131.50, 130.84, 127.71, 119.86, 59.63, 51.99, 42.44, 34.45, 31.02, 28.65; TOF ES+ MS: (M+H) 373.02; HPLC Ret: 8.69 min.

Preparation 18: t-butyl-4-((5-(2-chloro-4-hydroxy-phenyl)-1,3,4-oxadiazol-2-yl)thio)butanoate

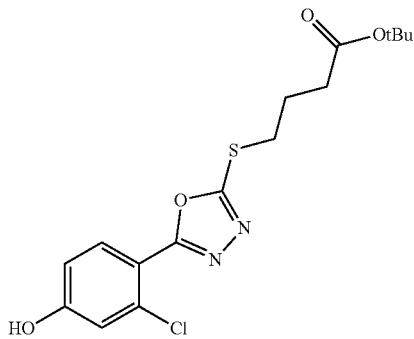 [SMILES: CC(C)(C)OC(=O)CCCSc1nnc(-c2ccc(O)cc2Cl)o1]

t-butyl-4-((5-(2-chloro-4-(prop-2-yn-1-yloxy)phenyl)-1,3,4-oxadiazol-2-yl)thio)butanoate (0.1 g, 0.25 mmol) was dissolved in 2 mL:1 mL DMF/H$_2$O solution. Bis(triphenylphosphine)palladium(II) chloride (0.01 g, 0.015 mmol) and trimethylamine (0.2 g, 1.96 mmol, 0.27 mL) were added and the reaction was stirred under nitrogen at 80° C. for 5 hr. The reaction was quenched with H$_2$O (5 mL) and acidified to pH 1 with 1N HCl (2 mL). The product was extracted with EtOAc (3×15 mL), and the resulting organic layer was washed with brine (20 mL), dried with MgSO$_4$, and evaporated. The oil was subjected to silica gel chromatography eluting with 40% EtOAc: 60% Hex. The fractions containing product were concentrated in vacuo. $^1$H NMR (500 MHz, CDCl$_3$-d) δ ppm 7.80 (d, 8.6 Hz, 1H) 7.07 (d, J=2.5 Hz, 1H) 6.89 (dd, J=8.6, 2.5 Hz, 1H) 3.33 (t, J=2.4 Hz, 1H) 2.43 (t, J=7.2 Hz, 2H) 2.15 (p, J=7.2 Hz, 2H) 1.46 (s, 9H); TOF ES$^+$ MS: (M+Na) 393.0; HPLC Ret: 7.37 min.

Other derivatives were made in an analogous fashion:

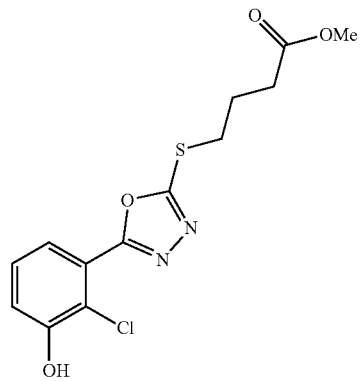

Methyl 4-((5-(2-chloro-3-hydroxyphenyl)-1,3,4-oxadiazol-2-yl)thio)butanoate

*note: methyl 4-((5-(2-chloro-3-(prop-2-yn-1-yloxy)phenyl)-1,3,4-oxadiazol-2-yl)thio)butanoate used as starting material; silica gel chromatography eluting with 35% EtOAc to 50% EtOAc: 65% Hex to 50% Hex: 0.01% AcOH. $^1$H NMR (500 MHz, CDCl$_3$-d) δ ppm 7.37 (dt, 7.8, 1.2 Hz, 1H) 7.30 (t, J=8.1 Hz, 1H) 7.15 (dd, J=8.2, 1.4 Hz, 1H) 3.67 (s, 3H) 3.37 (t, J=7.2 Hz, 2H) 2.54 (t, J=7.2 Hz, 2H) 2.16 (p, J=7.2 Hz, 2H); TOF ES+ MS: (M+H) 329.0; HPLC Ret: 6.02 min.

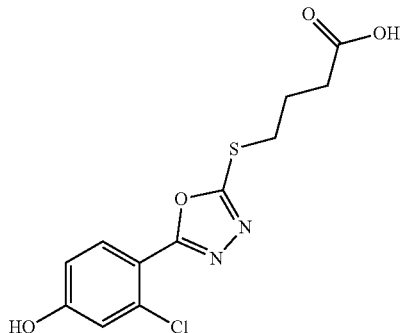 [SMILES: O=C(O)CCCSc1nnc(-c2ccc(O)cc2Cl)o1]

4-((5-(2-chloro-4-hydroxyphenyl)-1,3,4-oxadiazol-2-yl)thio)butanoic acid (A27)

*note: 4-((5-(2-chloro-4-(prop-2-yn-1-yloxy)phenyl)-1,3,4-oxadiazol-2-yl)thio)butanoic acid used as starting material; silica gel chromatography eluting with 70% EtOAc: 30% Hex: 0.01% AcOH. $^1$H NMR (500 MHz, MeOD-d$_4$) δ ppm 7.76 (dd, J=8.7, 1.3 Hz, 1H) 6.99 (dd, J=2.4, 1.3 Hz, 1H) 6.87 (ddd, J=8.6, 2.4, 1.3 Hz, 1H) 3.36 (t, J=7.1 Hz, 2H) 2.50 (t, J=7.1 Hz, 2H) 2.13 (p, J=7.1 Hz, 2H); $^{13}$C NMR (500 MHz, CDCl$_3$-) δ ppm 174.86, 164.42, 164.38, 161.35, 133.61, 131.97, 117.35, 114.52, 113.08, 31.84, 31.31, 24.65; TOF ES+ MS: (M+H) 315.02; HPLC Ret: 5.31 min; 98% pure.

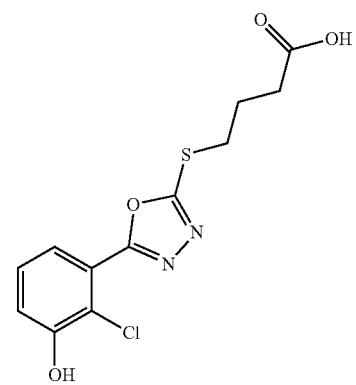 [SMILES: O=C(O)CCCSc1nnc(-c2cccc(O)c2Cl)o1]

4-((5-(2-chloro-3-hydroxyphenyl)-1,3,4-oxadiazol-2-yl)thio)butanoic acid (A26)

*note: 4-((5-(2-chloro-3-(prop-2-yn-1-yloxy)phenyl)-1,3,4-oxadiazol-2-yl)thio)butanoic acid used as starting material; silica gel chromatography eluting with 70% EtOAc: 30% Hex: 0.01% AcOH. White powder. Yield=25%. $^1$H NMR (500 MHz, MeOD-d$_4$) δ ppm 7.37 (dt, 7.8, 1.4 Hz, 1H) 7.29 (dt, J=8.0, 1.2 Hz, 1H) 7.14 (dt, J=8.2, 1.4 Hz, 1H) 3.37 (t, J=7.1 Hz, 2H) 2.51 (d, J=7.1 Hz, 2H) 2.14 (p, J=7.1 Hz, 2H); $^{13}$C NMR (500 MHz, CDCl$_3$-d) δ ppm 174.86, 165.19, 164.34, 154.45, 127.62, 123.52, 121.38, 119.37, 119.19, 31.86, 31.33, 24.63; TOF ES' MS: (M+H) 315.02; HPLC Ret: 5.05 min; 94% pure.

Preparation 18: tert-Butyl 4-((5-(2-chloro-4-(cyclopropylmethoxy)phenyl)-1,3,4-oxadiazol-2-yl)thio)butanoate

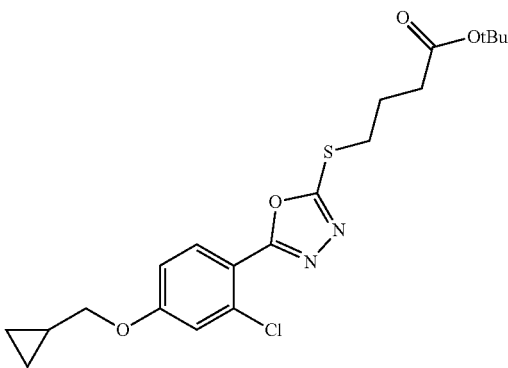 [SMILES: CC(C)(C)OC(=O)CCCSc1nnc(-c2ccc(OCC3CC3)cc2Cl)o1]

tert-Butyl 4-((5-(2-chloro-4-hydroxyphenyl)-1,3,4-oxadiazol-2-yl)thio)butanoate (0.05 g, 0.14 mmol) was dissolved in 1.0 mL DMF. 1-bromomethylcyclopropane (0.02 g, 0.02 mL, 0.16 mmol) along with $Cs_2CO_3$ (0.22 g, 0.67 mmol) were added and the reaction was stirred at 75° C. for 1 hr. The reaction was diluted with 10 mL brine and the product was extracted with EtOAc (3×10 mL). The organic layers were combined, dried with $MgSO_4$, and evaporated in vacuo. The subsequent oil was subjected to silica gel chromatography eluting with 20% EtOAc: 80% Hex. The fractions containing product were concentrated in vacuo. H NMR (500 MHz, $CDCl_3$-d) δ ppm 7.86 (d, 8.8 Hz, 1H) 7.04 (d, J=2.4 Hz, 1H) 6.90 (dd, J=8.8, 2.6 Hz, 1H) 3.86 (d, J=6.9 Hz, 2H) 3.33 (t, J=7.2 Hz, 2H) 2.42 (t, J=7.2 Hz, 2H) 2.15 (p, J=7.2 Hz, 2H) 1.45 (s, 9H) 1.33-1.22 (m, 1H) 0.73-0.63 (m, 2H) 0.43-0.34 (m, 2H); TOF $ES^+$ MS: (M+H) 425.13; HPLC Ret: 9.24 min.

Preparation 19: 4-((5-(4-chloro-2-hydroxyphenyl)-1,3,4-oxadiazol-2-yl)thio)butanoic acid (Compound C)

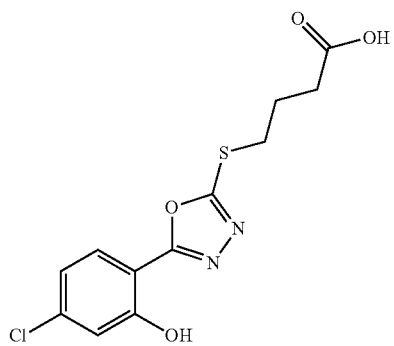

J. Org. Chem. 1979, 1661 tert-Butyl 4-((5-(2-(benzyloxy)-4-chlorophenyl)-1,3,4-oxadiazol-2-yl)thio)butanoate (0.085 g, 0.195 mmol) was dissolved in 0.5 mL ethane thiol. Boron trifluoride etherate (0.18 g, 1.29 mmol, 0.06 mL) was added and the reaction was stirred at 25° C. for 1 hr. The reaction was quenched with 5 mL $H_2O$ and the product was extracted with $Et_2O$ (3×20 mL). The organic layers were combined, washed with brine (2×15 mL), dried with $MgSO_4$, and evaporated in vacuo. $^1H$ NMR (500 MHz, DMSO-$d_6$) δ ppm 12.18 (br. s., 1H) 8.03 (d, J=1.9 Hz, 1H) 7.90 (d, J=8.4 Hz, 1H) 7.78 (dd, J=8.4, 1.9 Hz, 1H) 3.33 (t, J=2.4 Hz, 1H) 2.39 (t, J=7.3 Hz, 2H) 2.00 (p, J=7.3 Hz, 2H); HPLC Ret: 6.90 min.

Preparation 20: 4-((5-(2-chloro-3-cyclopropylphenyl)-1,3,4-oxadiazol-2-yl)thio)butanoic acid (A3)

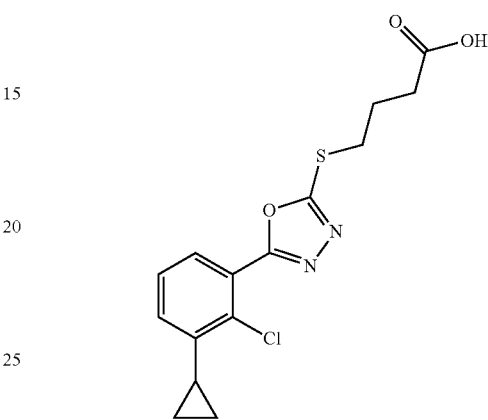

In a 10 mL round-bottomed flask tert-butyl-4-((5-(2-chloro-3-cyclopropylphenyl)-1,3,4-oxadiazol-2-yl)thio)butanoate (0.06 g, 0.15 mmol) was dissolved in DCM (0.5 mL). Trifluoroacetic acid (0.5 mL) was added and reaction was stirred at 25° C. for 1 hr. The crude mixture was concentrated in vacuo, and the subsequent oil was subjected to silica gel chromatography eluting with 0% MeOH: 100% DCM to 5% MeOH: 95% DCM. The fractions containing product were concentrated in vacuo. $^1H$ NMR (500 MHz, $CDCl_3$-d) δ ppm 7.68 (dd, J=7.7, 1.6 Hz, 1H) 7.29 (t, J=7.8 Hz, 1H) 7.15 (dd, J=7.8, 1.6 Hz, 1H) 3.39 (t, J=7.2 Hz, 2H) 2.59 (t, J=7.1 Hz, 2H) 2.31-2.18 (m, 3H) 1.13-0.98 (m, 2H) 0.77-0.66 (m, 2H); $^{13}C$ NMR (500 MHz, $CDCl_3$-d) δ ppm 175.45, 164.64, 143.05, 134.30, 129.45, 128.56, 126.72, 123.34, 109.99, 32.30, 31.60, 24.37, 14.02, 8.05; TOF ES+ MS: (M+H) 339.0; HPLC Ret: 6.94 min; 95% pure Other derivatives were made in an analogous fashion:

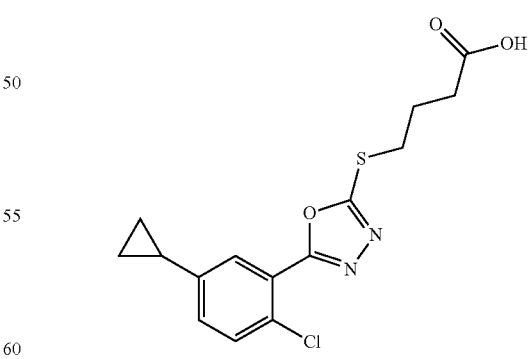

4-((5-(2-chloro-5-cyclopropylphenyl)-1,3,4-oxadiazol-2-yl)thio)butanoic acid. (A4)

$^1H$ NMR (500 MHz, $CDCl_3$-d) δ ppm 8.90 (br. s, 1H) 7.63 (d, J=2.2 Hz, 1H) 7.39 (d, J=8.3 Hz, 1H) 7.14 (dd, J=8.4, 2.3

Hz, 1H) 3.38 (t, J=7.1 Hz, 2H) 2.59 (t, J=7.1 Hz, 2H) 2.22 (p, J=7.1 Hz, 2H) 1.93 (tt, J=8.4, 5.0 Hz, 1H) 1.08-0.98 (m, 2H) 0.73 (dt, 6.8, 4.9 Hz, 2H); $^{13}$C NMR (500 MHz, CDCl$_3$-d) δ ppm 177.92, 164.64, 164.35, 143.59, 130.93, 129.86, 129.51, 128.16, 122.37, 32.32, 31.62, 24.35, 14.89, 9.56; TOF ES+ MS: (M+H) 339.1; HPLC Ret: 6.98 min; 97% pure.

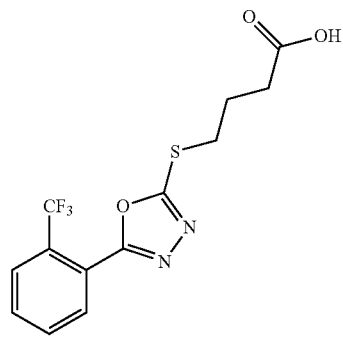 [SMILES: O=C(O)CCCSc1nnc(-c2ccccc2C(F)(F)F)o1]

4-((5-(2-(trifluoromethyl)phenyl)-1,3,4-oxadiazol-2-yl)thio)butanoic acid. (A5)

Column: 45% EtOAc: 55% Hex: 0.1% AcOH. $^1$H NMR (500 MHz, CDCl$_3$-d) δ ppm 10.45 (br. s, 1H) 8.07-8.00 (m, 1H) 7.85 (dd, J=7.1, 2.0 Hz, 1H) 7.75-7.65 (m, 2H) 3.37 (t, J=7.2 Hz, 2H) 2.59 (t, J=7.1 Hz, 2H) 2.21 (p, J=7.1 Hz, 2H); $^{13}$C NMR (500 MHz, CDCl$_3$-) δ ppm 178.29, 165.45, 164.05, 132.18, 131.65, 128.78, 127.06, 126.98, 124.19, 122.01, 32.28, 31.55, 24.34; TOF ES+ MS: (M+H) 333.1; HPLC Ret: 6.31 min; 97% pure.

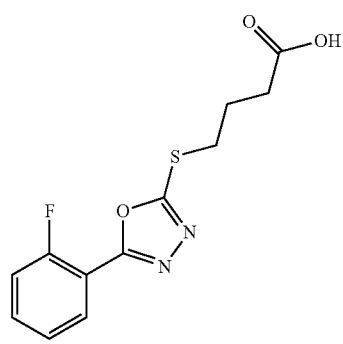 [SMILES: O=C(O)CCCSc1nnc(-c2ccccc2F)o1]

4-((5-(2-fluorophenyl)-1,3,4-oxadiazol-2-yl)thio)butanoic acid. (A6)

No column-crystallize from EtOAc/Hex. $^1$H NMR (500 MHz, CDCl$_3$-d) δ ppm 10.76 (br. s, 1H) 8.07-8.00 (td, J=7.5, 1.7 Hz, 1H) 7.53 (dd, J=7.6, 1.7 Hz, 1H) 7.31-7.20 (m, 2H) 3.39 (t, J=7.1 Hz, 2H) 2.59 (t, J=7.1 Hz, 2H) 2.21 (p, J=7.1 Hz, 2H); $^{13}$C NMR (500 MHz, CDCl$_3$-d) δ ppm 178.02, 164.64, 162.49, 158.77, 133.48, 129.47, 124.64, 116.64, 111.93, 32.32, 31.59, 24.30; TOF ES+ MS: (M+H) 283.1; HPLC Ret: 5.75 min; 96.6% pure.

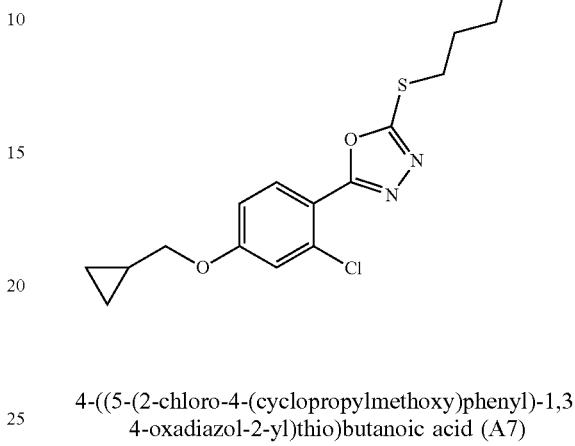

4-((5-(2-chloro-4-(cyclopropylmethoxy)phenyl)-1,3,4-oxadiazol-2-yl)thio)butanoic acid (A7)

Column: 45% EtOAc: 55% Hex: 0.1% AcOH. White powder. Yield=76%. $^1$H NMR (500 MHz, CDCl$_3$-d) δ ppm 10.24 (br. s, 1H) 7.85 (d, 8.8 Hz, 1H) 7.04 (d, J=2.4 Hz, 1H) 6.91 (dd, J=8.9, 2.5 Hz, 1H) 3.86 (t, J=7.0 Hz, 2H) 3.37 (t, J=7.1 Hz, 2H) 2.58 (t, J=7.1 Hz, 2H) 2.21 (p, J=7.1 Hz, 2H) 1.33-1.22 (m, 1H) 0.73-0.63 (m, 2H) 0.43-0.32 (m, 2H); $^{13}$C NMR (500 MHz, CDCl$_3$-d) δ ppm 177.98, 164.23, 164.02, 161.68, 134.07, 131.92, 116.88, 114.88, 113.86, 73.34, 32.31, 31.59, 24.34, 9.95, 3.28; TOF ES$^+$ MS: (M+H) 369.07; HPLC Ret: 7.14 min; 97% pure.

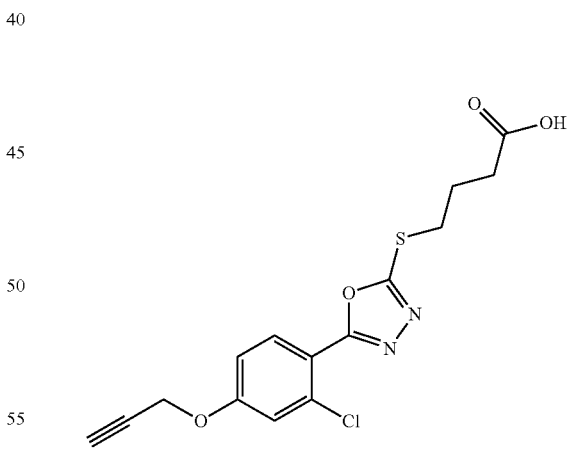

4-((5-(2-chloro-4-(prop-2-yn-1-yloxy)phenyl)-1,3,4-oxadiazol-2-yl)thio)butanoic acid $^1$H NMR (500 MHz, CDCl$_3$-d) δ ppm 9.99 (br. s., 1H) 7.90 (d, 8.8 Hz, 1H) 7.14 (d, J=2.5 Hz, 1H) 7.00 (dd, J=8.8, 2.6 Hz, 1H) 4.76 (d, J=2.4 Hz, 2H) 3.37 (t, J=7.1 Hz, 2H) 2.59 (m, 3H) 2.22 (p, J=7.1 Hz, 2H); TOF ES' MS: (M+H) 353.0; HPLC Ret: 6.35 min.

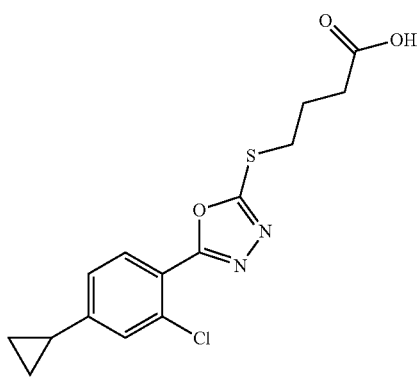 [SMILES: O=C(O)CCCSc1nnc(-c2ccc(C3CC3)cc2Cl)o1]

Preparation 21: 4-((5-(2-chloro-4-cyclopropylphenyl)-1,3,4-oxadiazol-2-yl)thio)butanoic acid (A1)

In a 25 mL round-bottomed flask methyl-4-((5-(2-chloro-4-cyclopropylphenyl)-1,3,4-oxadiazol-2-yl)thio)butanoate (0.07 g, 0.21 mmol) was dissolved in THF (2 mL). 1 M NaOH (2 mL) was added to the solution and the reaction was stirred at 25° C. for 1 hr. The THF was evaporated in vacuo and then uncharged organics were extracted with DCM (3×10 mL). The aqueous layer was acidified with 1 N HCl (7 mL) and the product was extracted with EtOAc (3×10 mL), washed with brine (3×10 mL), dried with MgSO$_4$, and concentrated in vacuo. The subsequent oil was subjected to silica gel chromatography eluting with 0% MeOH: 100% DCM to 5% MeOH: 95% DCM. The fractions containing product were concentrated in vacuo. $^1$H NMR (500 MHz, CDCl$_3$-d) δ ppm 8.11 (br. s., 1H) 7.81 (d, J=8.2 Hz, 1H) 7.19 (s, 1H) 7.05 (dd, J=8.2, 1.7 Hz, 1H) 2.58 (t, J=7.1 Hz, 2H) 2.37 (t, J=7.2 Hz, 2H) 2.20 (p, J=7.2 Hz, 2H) 1.96-1.91 (tt, J=8.4, 5.0 Hz, 1H) 1.08 (dt, J=6.9, 4.9 Hz, 2H) 0.78 (dt, J=6.9, 4.9 Hz, 2H); $^{13}$C NMR (500 MHz, CDCl$_3$-d) δ ppm 177.84, 164.36, 164.26, 150.10, 132.77, 130.66, 128.12, 124.27, 119.43, 32.36, 31.61, 24.37, 15.40, 10.41; TOF ES+ MS: (M+H) 339.0; HPLC Ret: 6.93 min; 97% pure.

Other derivatives were made in an analogous fashion:

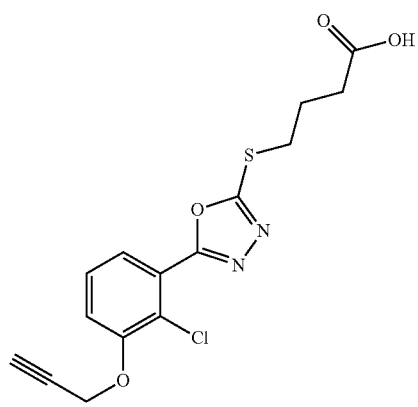 [SMILES: C#CCOc1cccc(-c2nnc(SCCCC(=O)O)o2)c1Cl]

4-((5-(2-chloro-3-(prop-2-yn-1-yloxy)phenyl)-1,3,4-oxadiazol-2-yl)thio)butanoic acid $^1$H NMR (500 MHz, CDCl$_3$-d) δ ppm 7.58 (dd, 7.8, 1.4 Hz, 1H) 7.37 (t, J=8.1 Hz, 1H) 7.28 (dd, J=8.1, 1.4 Hz, 1H) 4.85 (d, J=2.4 Hz, 2H) 3.39 (t, J=7.1 Hz, 2H) 2.61-2.59 (m, 3H) 2.23 (p, J=7.1 Hz, 2H); TOF ES' MS: (M+H) 353.0; HPLC Ret: 6.20 min.

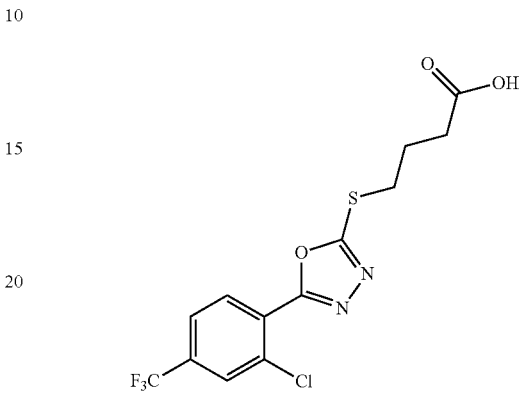

Methyl 4-((5-(2-chloro-4-(trifluoromethyl)phenyl)-1,3,4-oxadiazol-2-yl)thio)butanoate (A2)

No column—triturated with EtOAc/Hex. $^1$H NMR (500 MHz, CDCl$_3$-d) δ ppm 8.12 (d, J=8.2 Hz, 1H) 7.82 (d, J=1.6 Hz, 1H) 7.66 (dd, J=8.3, 1.8 Hz, 1H) 3.41 (t, J=7.2 Hz, 2H) 2.60 (t, J=7.1 Hz, 2H) 2.24 (p, J=7.1 Hz, 2H); $^{19}$F NMR (500 MHz, CDCl$_3$-d) δ ppm 63.24; $^{13}$C NMR (500 MHz, CDCl$_3$-d) δ ppm 177.45, 165.54, 163.05, 133.60, 131.35, 128.38, 125.99, 123.94, 123.91, 32.16, 31.62, 24.28; TOF ES+ MS: (M+H) 367.0; HPLC Ret: 6.99 min; 97% pure.

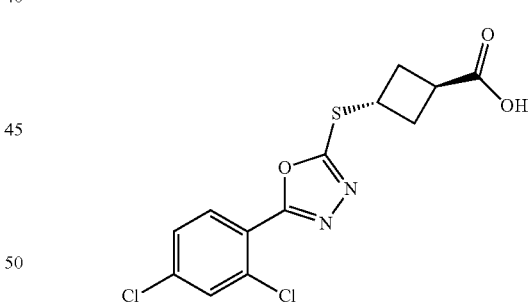

trans-3-((5-(2,4-dichlorophenyl)-1,3,4-oxadiazol-2-yl)thio)cyclobutanecarboxylic acid (B1)

Column: 40% EtOAc: 60% Hex: 0.01% AcOH. $^1$H NMR (500 MHz, CDCl$_3$-d) δ ppm 9.41 (br. s, 1H) 7.91 (d, J=8.5 Hz, 1H) 7.57 (d, J=2.0 Hz, 1H) 7.39 (dd, J=8.5, 2.0 Hz, 1H) 4.48 (p, J=7.5 Hz, 1H) 3.44 (tt, J=9.9, 5.5 Hz, 1H) 2.99 (ddd, J=13.9, 8.3, 5.8 Hz, 2H) 2.61 (dtd, J=13.3, 6.6, 2.2 Hz, 2H); $^{13}$C NMR (500 MHz, CDCl$_3$-d) δ ppm 179.91, 164.00, 163.37, 138.15, 133.76, 131.61, 131.20, 127.63, 121.31, 37.48, 35.22, 32.70, 29.68; TOF ES+ MS: (M+H) 344.99; HPLC Ret: 7.03 min; 95% pure.

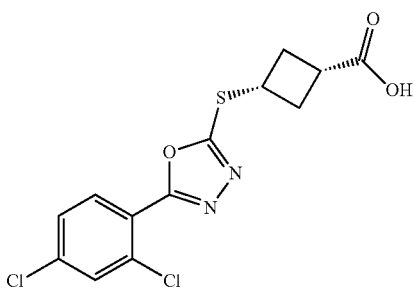 [SMILES: O=C(O)[C@H]1C[C@@H](Sc2nnc(-c3ccc(Cl)cc3Cl)o2)C1]

cis-3-((5-(2,4-Dichlorophenyl)-1,3,4-oxadiazol-2-yl)thio)cyclobutanecarboxylic acid (B2)

No column—crystallized from EtOAc/Hex. $^1$H NMR (500 MHz, CDCl$_3$-d) δ ppm 10.08 (br. s, 1H) 7.90 (d, J=8.4 Hz, 1H) 7.56 (d, J=2.1 Hz, 1H) 7.39 (dd, J=8.3, 2.1 Hz, 1H) 4.32 (p, J=8.6 Hz, 1H) 3.23 (p, J=8.9 Hz, 1H) 2.94 (dtt, J=10.8, 8.1, 4.6 Hz, 2H) 2.60 (qd, J=9.5, 2.7 Hz, 2H); $^{13}$C NMR (500 MHz, CDCl$_3$-d) δ ppm 178.94, 164.09, 163.37, 138.13, 133.75, 131.60, 131.18, 127.62, 121.30, 35.35, 34.62, 33.56; TOF ES+ MS: (M+H) 344.99; HPLC Ret: 6.90 min; 95% pure.

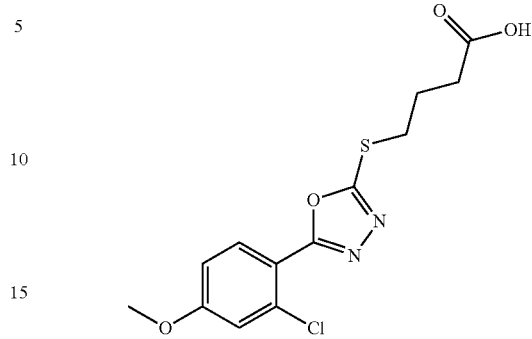

4-((5-(2-chloro-4-methoxyphenyl)-1,3,4-oxadiazol-2-yl)thio)butanoic acid. (A9)

$^1$H NMR (500 MHz, CDCl$_3$-d) δ ppm 10.78 (br. s, 1H) 7.87 (d, J=8.8 Hz, 1H) 7.04 (d, J=2.5 Hz, 1H) 6.91 (dd, J=8.8, 2.5 Hz, 1H) 3.87 (s, 3H) 3.37 (t, J=7.2 Hz, 2H) 2.59 (t, J=7.1 Hz, 2H) 2.21 (p, J=7.1 Hz, 2H); $^{13}$C NMR (500 MHz, CDCl$_3$-d) δ ppm 178.05, 164.18, 164.03, 162.21, 134.12, 131.96, 116.34, 115.12, 113.38, 55.76, 32.32, 31.60, 24.34; TOF ES' MS: (M+H) 329.0; HPLC Ret: 6.27 min; 99% pure.

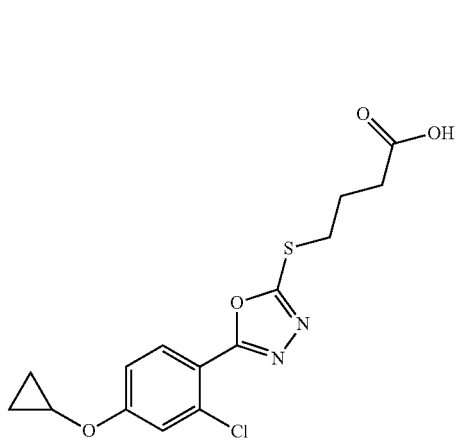 [SMILES: O=C(O)CCCSc1nnc(-c2ccc(OC3CC3)cc2Cl)o1]

4-((5-(2-chloro-4-cyclopropoxyphenyl)-1,3,4-oxadiazol-2-yl)thio)butanoic acid (A8)

No column—crystallized from EtOAc/Hex. $^1$H NMR (500 MHz, CDCl$_3$-d) δ ppm 11.07 (br. s, 1H) 7.86 (d, J=8.8 Hz, 1H) 7.22 (d, J=2.4 Hz, 1H) 7.04 (dd, J=8.8, 2.5 Hz, 1H) 3.80 (tt, J=6.2, 3.0 Hz, 1H) 3.37 (t, J=7.1 Hz, 2H) 2.59 (t, J=7.1 Hz, 2H) 2.21 (p, J=7.1 Hz, 2H) 0.92-0.77 (m, 4H); $^{13}$C NMR (500 MHz, CDCl$_3$-d) δ ppm 177.72, 164.22, 164.01, 133.99, 131.86, 131.78, 117.37, 115.47, 114.41, 51.62, 32.22, 31.60, 24.35, 6.28; TOF ES+MS: (M+H) 369.07; HPLC Ret: 6.90 min; 98% pure.

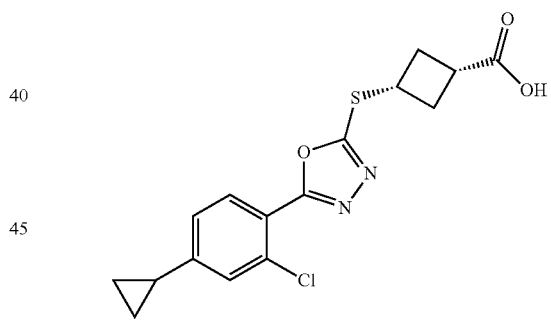

cis-3-((5-(2-chloro-4-cyclopropylphenyl)-1,3,4-oxadiazol-2-yl)thio)cyclobutanecarboxylic acid (B3)

Column: 30% EtOAc: 70% Hex to 35% EtOAc: 65% Hex: 0.1% AcOH followed by trituration with EtOAc/Hex. $^1$H NMR (500 MHz, CDCl$_3$-d) δ ppm 9.96 (br. s, 1H) 7.81 (d, J=8.2 Hz, 1H) 7.20 (d, J=1.7 Hz, 1H) 7.05 (dd, J=8.2, 1.7 Hz, 1H) 4.30 (p, J=8.7 Hz, 1H) 3.22 (p, J=8.9 Hz, 1H) 2.99-2.88 (m, 2H) 2.59 (qd, J=9.5, 2.8 Hz, 2H) 1.92 (tt, J=8.7, 5.0 Hz, 1H) 1.08 (dt, J=6.9, 4.9 Hz, 2H) 0.78 (dt, J=6.7, 4.8 Hz, 2H); $^{13}$C NMR (500 MHz, CDCl$_3$-d) δ ppm 178.92, 164.24, 163.46, 150.10, 132.79, 130.68, 128.12, 124.27, 119.46, 35.30, 34.66, 32.71, 15.40, 10.40; TOF ES+ MS: (M+H) 351.04; HPLC Ret: 7.00 min.

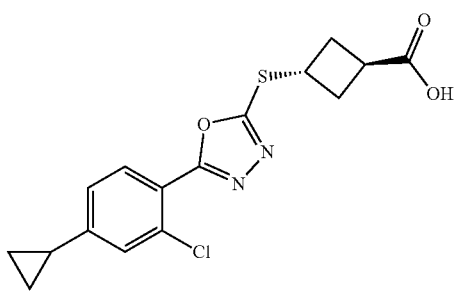 [SMILES: O=C(O)[C@H]1C[C@H](Sc2nnc(-c3ccc(C4CC4)cc3Cl)o2)C1]

trans-3-((5-(2-chloro-4-cyclopropylphenyl)-1,3,4-oxadiazol-2-yl)thio)cyclobutanecarboxylic acid (B4)

(DJK-7-12). Column: 40% EtOAc: 60% Hex: 0.1% AcOH followed by trituration with EtOAc/Hex. $^1$H NMR (500 MHz, CDCl$_3$-d) δ ppm 10.03 (br. s, 1H) 7.82 (d, J=8.2 Hz, 1H) 7.20 (d, J=1.7 Hz, 1H) 7.05 (dd, J=8.2, 1.7 Hz, 1H) 4.46 (p, J=8.7 Hz, 1H) 3.43 (p, J=4.8 Hz, 1H) 2.98 (ddd, J=13.7, 8.1, 5.4 Hz, 2H) 2.60 (ddd, J=13.4, 9.6, 6.5 Hz, 2H) 1.92 (tt, J=8.5, 5.4 Hz, 1H) 1.09 (dt, J=6.9, 4.9 Hz, 2H) 0.79 (dt, J=6.8, 4.9 Hz, 2H); $^{13}$C NMR (500 MHz, CDCl$_3$-d) δ ppm 180.08, 164.27, 163.36, 150.12, 132.80, 130.69, 128.14, 124.29, 119.46, 37.43, 35.23, 32.70, 15.41, 10.40; TOF ES+ MS: (M+H) 351.04; HPLC Ret: 7.21 min.

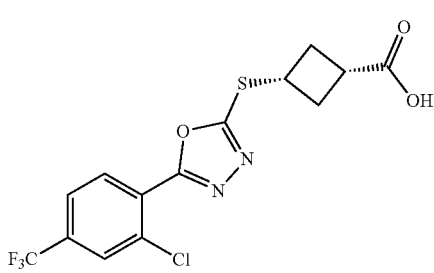

cis-3-((5-(2-chloro-4-(trifluoromethyl)phenyl)-1,3,4-oxadiazol-2-yl)thio)cyclobutanecarboxylic acid (B5)

Column: 40% EtOAc: 60% Hex: 0.1% AcOH followed by trituration with EtOAc/Hex. $^1$H NMR (500 MHz, CDCl$_3$-d) δ ppm 9.69 (br. s, 1H) 8.12 (d, J=8.2 Hz, 1H) 7.82 (d, J=1.7 Hz, 1H) 7.66 (dd, J=8.3, 1.7 Hz, 1H) 4.34 (p, J=8.6 Hz, 1H) 3.24 (p, J=8.9 Hz, 1H) 3.04-2.91 (m, 2H) 2.61 (qd, J=9.4, 2.8 Hz, 2H); $^{13}$C NMR (500 MHz, CDCl$_3$-d) δ ppm 178.97, 164.68, 162.99, 134.31, 133.60, 131.60, 128.41, 125.94, 123.95, 121.59, 35.35, 34.63, 33.53; TOF ES+ MS: (M+H) 379.00; HPLC Ret: 7.14 min; 94.5% pure.

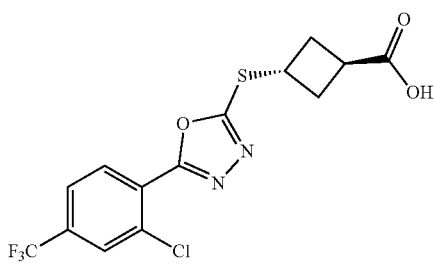 [SMILES: O=C(O)[C@H]1C[C@H](Sc2nnc(-c3ccc(C(F)(F)F)cc3Cl)o2)C1]

trans-3-((5-(2-chloro-4-(trifluoromethyl)phenyl)-1,3,4-oxadiazol-2-yl)thio)cyclobutanecarboxylic acid (B6)

Column: 40% EtOAc: 60% Hex: 0.1% AcOH followed by trituration with EtOAc/Hex. $^1$H NMR (500 MHz, CDCl$_3$-d) δ ppm 9.43 (br. s, 1H) 8.12 (d, J=8.2 Hz, 1H) 7.82 (d, J=1.7 Hz, 1H) 7.66 (dd, J=8.3, 1.7 Hz, 1H) 4.51 (p, J=7.5 Hz, 1H) 3.45 (p, J=5.5 Hz, 1H) 3.01 (ddd, J=13.7, 8.1, 5.3 Hz, 2H) 2.62 (ddd, J=13.8, 9.5, 6.5 Hz, 2H); $^{13}$C NMR (500 MHz, CDCl$_3$-d) δ ppm 180.10, 164.62, 162.98, 134.33, 133.60, 131.38, 128.39, 125.94, 123.93, 121.70, 37.49, 35.26, 32.68; TOF ES+ MS: (M+H) 379.00; HPLC Ret: 7.25 min; 98% pure.

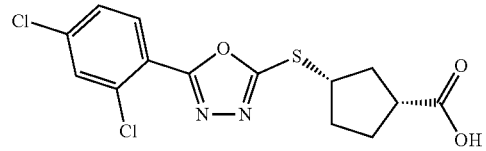 [SMILES: O=C(O)[C@@H]1CC[C@H](Sc2nnc(-c3ccc(Cl)cc3Cl)o2)C1]

cis-3-((5-(2,4-dichlorophenyl)-1,3,4-oxadiazol-2-yl)thio)cyclopentanecarboxylic acid (B7)

Column: 40% EtOAc: 60% Hex: 0.1% AcOH followed by trituration with EtOAc/Hex. $^1$H NMR (500 MHz, CDCl$_3$-d) δ ppm 10.61 (br. s, 1H) 7.92 (d, J=8.5 Hz, 1H) 7.57 (d, J=1.7 Hz, 1H) 7.39 (dd, J=8.5, 1.8 Hz, 1H) 4.28-4.20 (m, 1H) 3.18-3.08 (m, 1H) 2.67-2.57 (m, 1H) 2.51-2.41 (m, 1H) 2.29-1.99 (m, 3H) 1.92-1.83 (m, 1H); $^{13}$C NMR (500 MHz, CDCl$_3$-d) δ ppm 181.03, 164.71, 163.29, 138.08, 133.73, 131.60, 131.18, 127.62, 121.35, 45.04, 42.42, 36.87, 33.18, 28.77; TOF ES+ MS: (M+H) 358.99; HPLC Ret: 7.33 min.

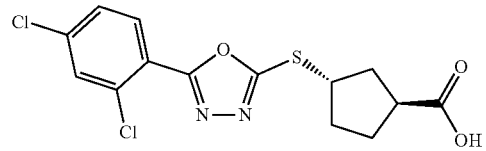 [SMILES: O=C(O)[C@H]1CC[C@H](Sc2nnc(-c3ccc(Cl)cc3Cl)o2)C1]

trans-3-((5-(2,4-dichlorophenyl)-1,3,4-oxadiazol-2-yl)thio)cyclopentanecarboxylic acid (B8)

No column—trituration with EtOAc/Hex. $^1$H NMR (500 MHz, CDCl$_3$-d) δ ppm 11.54 (br. s, 1H) 7.87 (d, J=8.5 Hz, 1H) 7.58 (d, J=1.9 Hz, 1H) 7.42 (dd, J=8.5, 1.9 Hz, 1H) 5.32-5.24 (m, 1H) 3.31-3.23 (m, 1H) 2.53-2.45 (m, 1H) 2.38-2.28 (m, 3H) 2.14-2.00 (m, 2H); $^{13}$C NMR (500 MHz, CDCl$_3$-d) δ ppm 181.40, 175.08, 156.36, 138.64, 133.80, 131.56, 130.85, 127.73, 119.81, 59.55, 42.40, 34.24, 31.02, 28.56; TOF ES+ MS: (M+H) 358.99; HPLC Ret: 7.58 min; 95% pure.

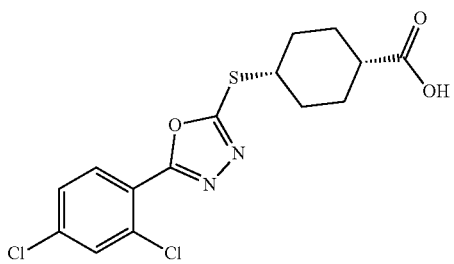 [SMILES: O=C(O)[C@H]1CC[C@@H](Sc2nnc(-c3ccc(Cl)cc3Cl)o2)CC1]

cis-4-((5-(2,4-dichlorophenyl)-1,3,4-oxadiazol-2-yl)thio)cyclohexanecarboxylic acid (B9)

Rxn time=24 hr. Column: 40% EtOAc: 60% Hex: 0.1% AcOH followed by trituration with EtOH/H$_2$O. $^1$H NMR (500 MHz, CDCl$_3$-d) δ ppm 10.66 (br. s, 1H) 7.91 (d, J=8.5 Hz, 1H) 7.56 (d, J=1.8 Hz, 1H) 7.39 (dd, J=8.5, 1.6 Hz, 1H) 4.15-4.10 (m, 1H) 2.62-2.55 (m, 1H) 2.11-1.98 (m, 6H) 1.93-1.83 (m, 2H); $^{13}$C NMR (500 MHz, CDCl$_3$-d) δ ppm 180.77, 164.93, 163.21, 138.01, 133.71, 131.57, 131.16, 127.59, 121.40, 45.46, 40.46, 30.08, 25.32; TOF ES+ MS: (M+H) 373.00; HPLC Ret: 7.40 min.

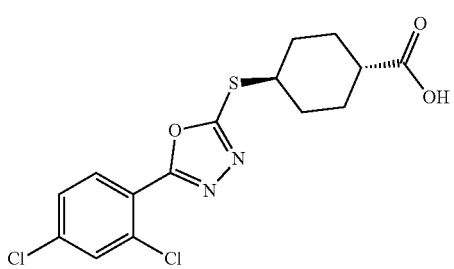 [SMILES: O=C(O)[C@H]1CC[C@H](Sc2nnc(-c3ccc(Cl)cc3Cl)o2)CC1]

trans-4-((5-(2,4-dichlorophenyl)-1,3,4-oxadiazol-2-yl)thio)cyclohexanecarboxylic acid (B10)

Rxn time=24 hr. Column: 40% EtOAc: 60% Hex: 0.1% AcOH followed by trituration with EtOAc/Hex. $^1$H NMR (500 MHz, CDCl$_3$-d) δ ppm 9.67 (br. s, 1H) 7.92 (d, J=8.5 Hz, 1H) 7.57 (d, J=2.0 Hz, 1H) 7.39 (dd, J=8.5, 2.0 Hz, 1H) 3.75-3.69 (m, 1H) 2.44-2.38 (m, 3H) 2.21-2.09 (m, 2H) 1.73-1.57 (m, 4H); $^{13}$C NMR (500 MHz, CDCl$_3$-d) δ ppm 180.73, 164.43, 163.27, 138.07, 133.70, 131.58, 131.18, 127.62, 121.38, 45.43, 41.70, 32.10, 28.45; TOF ES+ MS: (M+H) 373.00; HPLC Ret: 7.55 min; 98% pure.

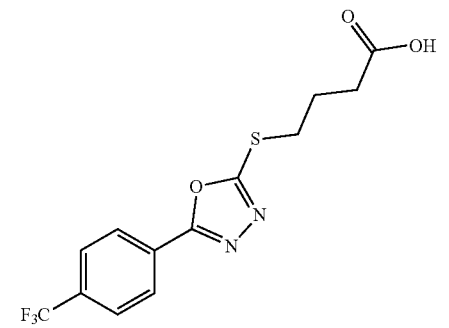 [SMILES: O=C(O)CCCSc1nnc(-c2ccc(C(F)(F)F)cc2)o1]

4-((5-(4-(trifluoromethyl)phenyl)-1,3,4-oxadiazol-2-yl)thio)butanoic acid (A11)

No column—crystallization with EtOAc/Hex. $^1$H NMR (500 MHz, CDCl$_3$-d) δ ppm 10.41 (br. s., 1H) 8.14 (d, J=8.2 Hz, 2H) 7.77 (d, J=8.2 Hz, 2H) 3.41 (t, J=7.2 Hz, 2H) 2.60 (t, J=7.1 Hz, 2H) 2.22 (p, J=7.1 Hz, 2H); $^{19}$F NMR (500 MHz, CDCl$_3$-d) δ ppm −63.16 (s, 3H); $^{13}$C NMR (500 MHz, CDCl$_3$-d) δ ppm 177.97, 165.00, 164.64, 133.41, 126.97, 126.13, 124.59, 121.90, 32.22, 31.57, 24.22; TOF ES+ MS: (M+H) 333.04; HPLC Ret: 6.76 min; 98.5% pure.

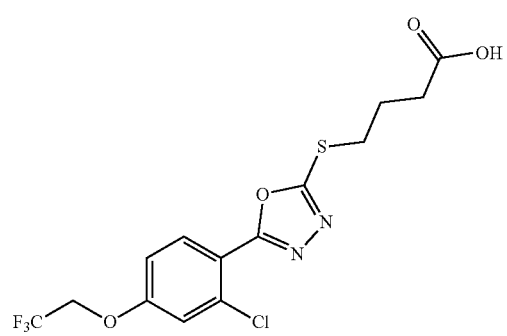 [SMILES: O=C(O)CCCSc1nnc(-c2ccc(OCC(F)(F)F)cc2Cl)o1]

4-((5-(2-chloro-4-(2,2,2-trifluoroethoxy)phenyl)-1,3,4-oxadiazol-2-yl)thio)butanoic acid (A12)

No column—crystallization with EtOAc/Hex. $^1$H NMR (500 MHz, CDCl$_3$-d) δ ppm 10.85 (br. s., 1H) 7.93 (d, J=8.8 Hz, 1H) 7.12 (d, J=2.5 Hz, 1H) 6.98 (dd, J=8.9, 2.6 Hz, 1H) 4.42 (q, J=7.9 Hz, 2H) 3.38 (t, J=7.1 Hz, 2H) 2.59 (t, J=7.1 Hz, 2H) 2.22 (p, J=7.1 Hz, 2H); $^{19}$F NMR (500 MHz, CDCl$_3$-d) δ ppm −73.76 (t, 3H); $^{13}$C NMR (500 MHz, CDCl$_3$-d) δ ppm 177.80, 164.41, 163.71, 159.47, 134.41, 132.23, 123.89, 117.40, 117.14, 113.78, 65.58, 32.22, 31.59, 24.30; TOF ES+ MS: (M+H) 397.01; HPLC Ret: 6.88 min; 97% pure.

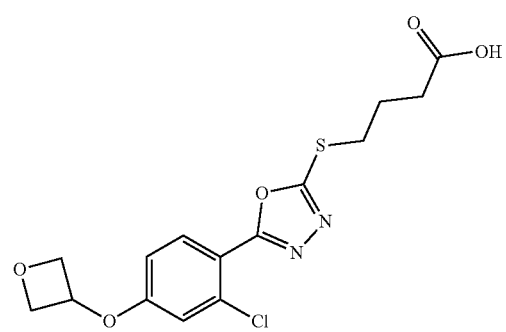 [SMILES: O=C(O)CCCSc1nnc(-c2ccc(OC3COC3)cc2Cl)o1]

4-((5-(2-chloro-4-(oxetan-3-yloxy)phenyl)-1,3,4-oxadiazol-2-yl)thio)butanoic acid (A13)

No column—crystallization with EtOAc/Hex. $^1$H NMR (500 MHz, CDCl$_3$-d) δ ppm 7.88 (d, 8.8 Hz, 1H) 6.85 (d, J=2.5 Hz, 1H) 6.73 (dd, J=8.8, 2.5 Hz, 1H) 5.27 (p, 6.0 Hz, 1H) 5.02 (t, J=7.1 Hz, 2H) 4.78 (dd, J=7.3, 5.1 Hz, 2H) 3.37 (t, J=7.1 Hz, 2H) 2.58 (t, J=7.1 Hz, 2H) 2.21 (p, J=7.1 Hz, 2H); $^{13}$C NMR (500 MHz, CDCl$_3$-d) δ ppm 177.64, 164.26, 163.89, 159.11, 134.38, 132.27, 117.00, 116.16, 113.67, 77.44, 70.69, 32.25, 31.60, 24.33; TOF ES+ MS: (M+H) 371.03; HPLC Ret: 5.85 min; 98% pure.

31.62, 24.37; TOF ES+ MS: (M+H) 385.05; HPLC Ret: 5.83 min; 94% pure.

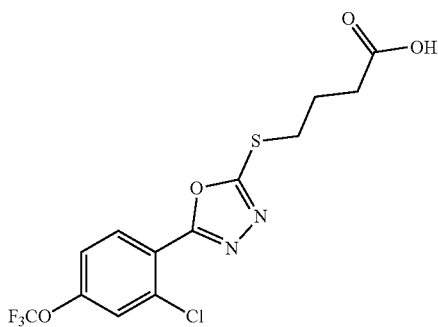 [SMILES: O=C(O)CCCSc1nnc(-c2ccc(OC(F)(F)F)cc2Cl)o1]

4-((5-(2-chloro-4-(trifluoromethoxy)phenyl)-1,3,4-oxadiazol-2-yl)thio)butanoic acid (A14)

No column—crystallization with EtOAc/Hex. $^1$H NMR (500 MHz, CDCl$_3$-d) δ ppm 8.02 (d, J=8.8 Hz, 1H) 7.42 (d, J=2.3 Hz, 1H) 7.27 (dd, J=8.8, 2.3 Hz, 1H) 3.39 (t, J=7.1 Hz, 2H) 2.60 (t, J=7.1 Hz, 2H) 2.24 (p, J=7.1 Hz, 2H); $^{19}$F NMR (500 MHz, CDCl$_3$-d) δ ppm −57.88 (s, 3H); $^{13}$C NMR (500 MHz, CDCl$_3$-d) δ ppm 177.82, 165.06, 163.15, 151.14, 134.28, 132.15, 123.89, 123.27, 121.36, 119.17, 32.21, 31.60, 24.27; TOF ES+ MS: (M+H) 382.99; HPLC Ret: 7.14 min; 98% pure.

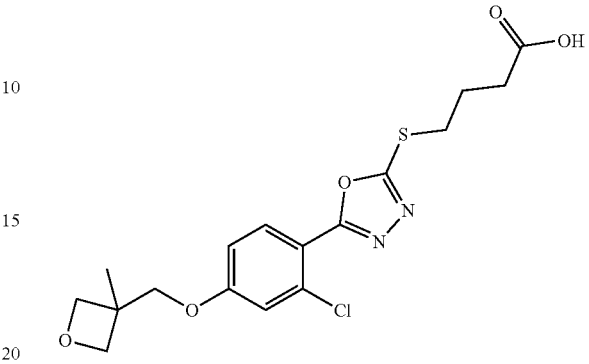

4-((5-(2-chloro-4-((3-methyloxetan-3-yl)methoxy)phenyl)-1,3,4-oxadiazol-2-yl)thio)butanoic acid (A16)

No column—crystallization with EtOAc/Hex. $^1$H NMR (500 MHz, CDCl$_3$-d) δ ppm 7.89 (d, 8.8 Hz, 1H) 7.10 (d, J=2.5 Hz, 1H) 6.96 (dd, J=8.8, 2.5 Hz, 1H) 4.63 (d, J=6.1 Hz, 2H) 4.50 (d, J=6.0 Hz, 2H) 4.10 (s, 2H) 3.38 (t, J=7.1 Hz, 2H) 2.59 (t, J=7.1 Hz, 2H) 2.21 (p, J=7.1 Hz, 2H) 1.46 (s, 3H); $^{13}$C NMR (500 MHz, CDCl$_3$-d) δ ppm 177.32, 164.09, 161.50, 134.17, 132.01, 116.94, 115.54, 113.72, 79.54, 73.17, 39.54, 32.22, 31.61, 24.36, 21.12; TOF ES+ MS: (M+H) 399.06; HPLC Ret: 6.24 min; 98% pure.

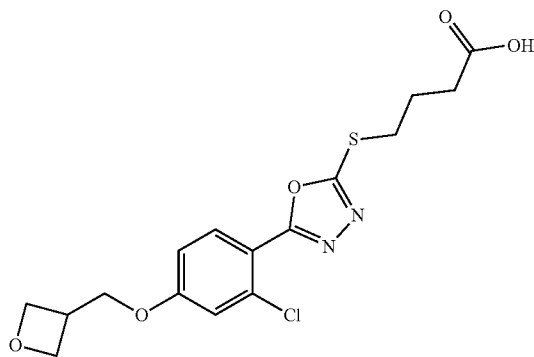 [SMILES: O=C(O)CCCSc1nnc(-c2ccc(OCC3COC3)cc2Cl)o1]

4-((5-(2-chloro-4-(oxetan-3-ylmethoxy)phenyl)-1,3,4-oxadiazol-2-yl)thio)butanoic acid (A15)

No column—crystallization with EtOAc/Hex. $^1$H NMR (500 MHz, CDCl$_3$-d) δ ppm 7.89 (d, 8.8 Hz, 1H) 7.08 (d, J=2.5 Hz, 1H) 6.94 (dd, J=8.8, 2.5 Hz, 1H) 4.91 (p, 6.0 Hz, 1H) 4.59 (t, J=6.1 Hz, 2H) 4.26 (d, J=6.6 Hz, 2H) 3.47 (hept., J=6.6 Hz, 1H) 3.37 (t, J=7.1 Hz, 2H) 2.58 (t, J=7.1 Hz, 2H) 2.21 (p, J=7.1 Hz, 2H); $^{13}$C NMR (500 MHz, CDCl$_3$-d) δ ppm 177.35, 164.11, 164.07, 161.27, 134.18, 132.02, 116.88, 115.56, 113.70, 73.99, 69.44, 34.28, 32.23,

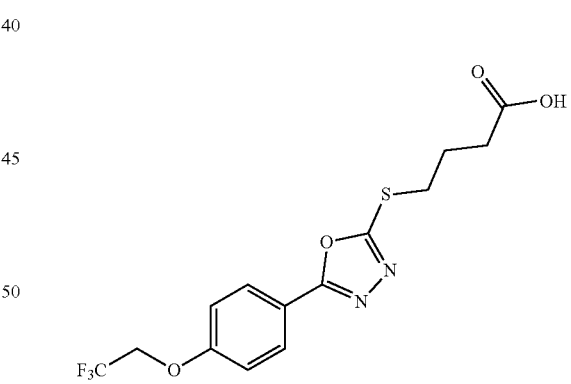

4-((5-(4-(2,2,2-trifluoroethoxy)phenyl)-1,3,4-oxadiazol-2-yl)thio)butanoic acid (A17)

No column—crystallization with EtOAc/Hex. $^1$H NMR (500 MHz, DMSO-d$_6$) δ ppm 12.20 (br. s., 1H) 7.96 (d, J=8.0 Hz, 2H) 7.27 (d, J=8.0 Hz, 2H) 4.90 (q, J=7.9 Hz, 2H) 3.32 (t, J=7.2 Hz, 2H) 2.40 (t, J=7.3 Hz, 2H) 2.00 (p, J=7.2 Hz, 2H); $^{19}$F NMR (500 MHz, DMSO-d$_6$) δ ppm −72.55 (t, 3H); $^{13}$C NMR (500 MHz, DMSO-d$_6$) δ ppm 174.15, 165.20, 135.31, 130.88, 128.77, 117.45, 116.15, 113.69, 64.91, 32.61, 31.95, 24.99; TOF ES+ MS: (M+H) 363.06; HPLC Ret: 6.59 min; 99% pure.

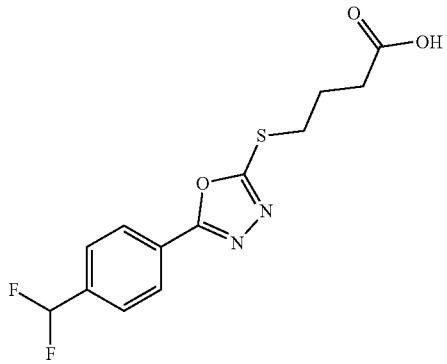 [SMILES: O=C(O)CCCSc1nnc(-c2ccc(C(F)F)cc2)o1]

4-((5-(4-(difluoromethyl)phenyl)-1,3,4-oxadiazol-2-yl)thio)butanoic acid (A18)

No column—crystallization with EtOAc/Hex. ¹H NMR (500 MHz, CDCl₃-d) δ ppm 11.13 (br. s., 1H) 8.10 (d, J=8.0 Hz, 2H) 7.65 (d, J=8.0 Hz, 2H) 6.70 (t, J=56.1 Hz, 1H) 3.40 (t, J=7.1 Hz, 2H) 2.60 (t, J=7.1 Hz, 2H) 2.23 (p, J=7.1 Hz, 2H); ¹⁹F NMR (500 MHz, CDCl₃-d) δ ppm −112.20 (d, 2H); ¹³C NMR (500 MHz, CDCl₃-d) δ ppm 178.10, 164.99, 164.69, 137.31, 126.97, 126.35, 125.64, 113.86, 111.95, 32.27, 31.57, 24.23; TOF ES+ MS: (M+H) 315.06; HPLC Ret: 6.20 min; 99% pure.

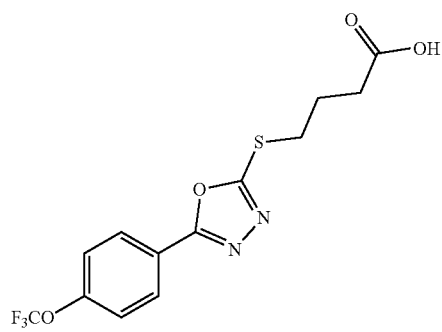 [SMILES: O=C(O)CCCSc1nnc(-c2ccc(OC(F)(F)F)cc2)o1]

4-((5-(4-(trifluoromethoxy)phenyl)-1,3,4-oxadiazol-2-yl)thio)butanoic acid (A19)

No column—crystallization with EtOAc/Hex. ¹H NMR (500 MHz, CDCl₃-d) δ ppm 10.88 (br. s., 1H) 8.06 (d, J=8.6 Hz, 2H) 7.34 (d, J=8.4 Hz, 2H) 3.39 (t, J=7.2 Hz, 2H) 2.60 (t, J=7.1 Hz, 2H) 2.22 (p, J=7.1 Hz, 2H); ¹⁹F NMR (500 MHz, CDCl₃-d) δ ppm −57.72 (s, 3H); ¹³C NMR (500 MHz, CDCl₃-d) δ ppm 178.08, 164.72, 164.47, 151.51, 128.47, 122.01, 121.23, 119.25, 32.26, 31.57, 24.23; TOF ES+ MS: (M+H) 349.05; HPLC Ret: 6.86 min; 98% pure.

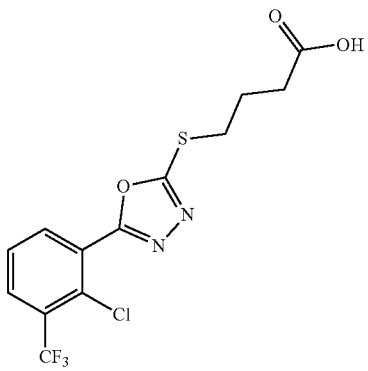 [SMILES: O=C(O)CCCSc1nnc(-c2cccc(C(F)(F)F)c2Cl)o1]

4-((5-(2-chloro-3-(trifluoromethyl)phenyl)-1,3,4-oxadiazol-2-yl)thio)butanoic acid (A20)

(DJK-7-28). No column—crystallization with EtOAc/Hex. ¹H NMR (500 MHz, CDCl₃-d) δ ppm 10.88 (br. s., 1H) 8.10 (dd, J=7.9, 1.6 Hz, 1H) 7.89 (dd, J=7.9, 1.6 Hz, 1H) 7.54 (t, J=7.9 Hz, 1H) 3.41 (t, J=7.2 Hz, 2H) 2.60 (t, J=7.1 Hz, 2H) 2.24 (p, J=7.2 Hz, 2H); ¹⁹F NMR (500 MHz, CDCl₃-d) δ ppm −62.59 (s, 3H); ¹³C NMR (500 MHz, CDCl₃-d) δ ppm 178.11, 165.46, 163.33, 134.44, 130.31, 130.27, 127.03, 125.65, 123.52, 121.34, 32.26, 31.61, 24.24; TOF ES+ MS: (M+H) 367.01; HPLC Ret: 6.81 min; 98% pure.

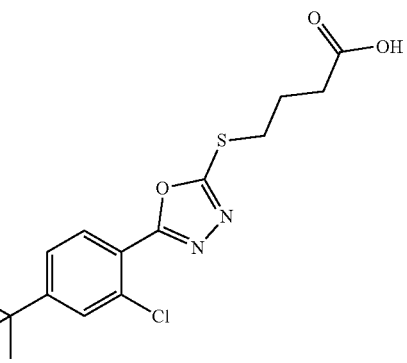

4-((5-(2-chloro-4-(2-fluoropropan-2-yl)phenyl)-1,3,4-oxadiazol-2-yl)thio)butanoic acid (A21)

Column: 30% EtOAc: 70% Hex to 60% EtOAc: 40% Hex: 0.1% AcOH. ¹H NMR (500 MHz, CDCl₃-d) δ ppm 9.58 (br. s, 1H) 7.94 (d, J=8.2 Hz, 1H) 7.56 (d, J=1.7 Hz, 1H) 7.38 (dd, J=8.3, 1.7 Hz, 1H) 3.39 (t, J=7.1 Hz, 2H) 2.60 (t, J=7.1 Hz, 2H) 2.23 (p, J=7.1 Hz, 2H) 1.72 (s, 3H) 1.68 (s, 3H); ¹⁹F NMR (500 MHz, CDCl₃-d) δ ppm −139.23 (hept, 1H); ¹³C NMR (500 MHz, CDCl₃-d) δ ppm 178.08, 164.73, 163.90, 150.88, 133.03, 130.94, 126.80, 122.72, 121.58, 32.30, 31.60, 29.05, 28.85, 24.31; TOF ES+ MS: (M+H) 359.06; HPLC Ret: 6.95 min; 98% pure.

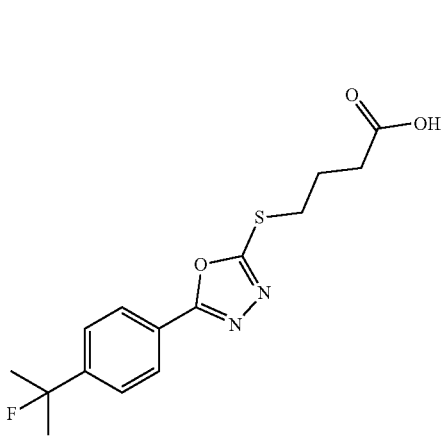 [SMILES: CC(C)(F)c1ccc(-c2nnc(SCCCC(=O)O)o2)cc1]

4-((5-(2-chloro-4-(2-fluoropropan-2-yl)phenyl)-1,3,4-oxadiazol-2-yl)thio)butanoic acid (A22)

No column—crystallization with EtOAc/Hex. ¹H NMR (500 MHz, CDCl₃-d) δ ppm 7.99 (d, J=8.4 Hz, 2H) 7.51 (d, J=8.4 Hz, 2H) 3.39 (t, J=7.1 Hz, 2H) 2.60 (t, J=7.1 Hz, 2H) 2.22 (p, J=7.1 Hz, 2H) 1.73 (s, 3H) 1.69 (s, 3H); ¹⁹F NMR (500 MHz, CDCl₃-d) δ ppm −138.73 (hept, 1H); ¹³C NMR (500 MHz, CDCl₃-d) δ ppm 177.78, 165.57, 164.03, 149.70, 126.72, 124.48, 122.44, 32.24, 31.57, 29.20, 29.00, 24.28; TOF ES+ MS: (M+H) 325.10; HPLC Ret: 6.64 min; 94% pure.

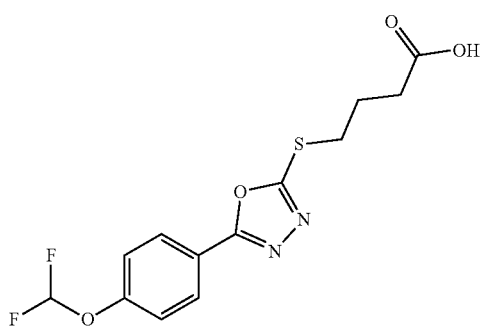 [SMILES: O=C(O)CCCSc1nnc(-c2ccc(OC(F)F)cc2)o1]

4-((5-(4-(difluoromethoxy)phenyl)-1,3,4-oxadiazol-2-yl)thio)butanoic acid (A23)

No column—crystallization with EtOAc/Hex. ¹H NMR (500 MHz, CDCl₃-d) δ ppm 10.81 (br. s., 1H) 8.02 (d, J=8.5 Hz, 2H) 7.24 (d, J=8.5 Hz, 2H) 6.60 (t, J=73.0 Hz, 1H) 3.39 (t, J=7.2 Hz, 2H) 2.59 (t, J=7.1 Hz, 2H) 2.22 (p, J=7.1 Hz, 2H); ¹⁹F NMR (500 MHz, CDCl₃-d) δ ppm −81.70 (d, 2H); ¹³C NMR (500 MHz, CDCl₃-d) δ ppm 178.00, 164.97, 164.18, 153.54, 128.53, 120.55, 119.70, 117.43, 115.35, 111.26, 32.26, 31.57, 24.25; TOF ES+ MS: (M+H) 331.06; HPLC Ret: 6.28 min; 99.7% pure.

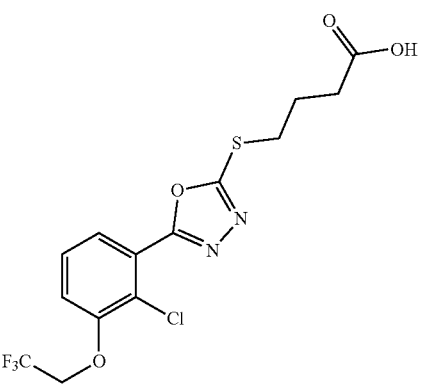 [SMILES: O=C(O)CCCSc1nnc(-c2cccc(OCC(F)(F)F)c2Cl)o1]

4-((5-(2-chloro-3-(2,2,2-trifluoroethoxy)phenyl)-1,3,4-oxadiazol-2-yl)thio)butanoic acid (A25)

Column: 55% EtOAc: 45% Hex to 60% EtOAc: 40% Hex: 0.1% AcOH. ¹H NMR (500 MHz, CDCl₃-d) δ ppm 7.67 (d, 7.9 Hz, 1H) 7.38 (t, J=8.1 Hz, 1H) 7.16 (d, J=8.2 Hz, 1H) 4.47 (q, J=8.0 Hz, 2H) 3.39 (t, J=7.2 Hz, 2H) 2.59 (t, J=7.2 Hz, 2H) 2.22 (p, J=7.2 Hz, 2H); ¹³C NMR (500 MHz, CDCl₃-d) δ ppm 177.76, 165.01, 163.76, 154.32, 127.78, 125.13, 124.84, 121.84, 118.05, 67.37, 32.27, 31.60, 29.70, 24.33; ¹⁹F NMR (500 MHz, CDCl₃-d) δ ppm −73.84 (t, 3H); TOF ES⁺ MS: (M+H) 397.02; HPLC Ret: 6.56 min; 95% pure.

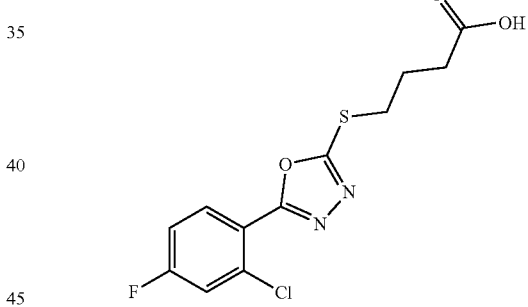

4-((5-(2-chloro-4-fluorophenyl)-1,3,4-oxadiazol-2-yl)thio)butanoic acid (A24)

Column: 45% EtOAc: 55% Hex. ¹H NMR (500 MHz, CDCl₃-d) δ ppm 7.96 (dd, J=8.8, 5.9 Hz, 1H) 7.30 (dd, J=8.4, 2.5 Hz, 1H) 7.13 (ddd, J=8.7, 7.5, 2.6 Hz, 1H) 3.39 (t, J=7.2 Hz, 2H) 2.59 (t, J=7.2 Hz, 2H) 2.23 (p, J=7.2 Hz, 2H); ¹³C NMR (500 MHz, CDCl₃-d) δ ppm 177.89, 164.93, 163.42, 162.89, 134.53, 132.59, 119.35, 118.87, 114.96, 32.25, 31.59, 24.29; ¹⁹F NMR (500 MHz, CDCl₃-d) δ ppm −105.46 (t, 1H) TOF ES⁺ MS: (M+H) 317.02; HPLC Ret: 6.23 min; 100% pure.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising"

will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A compound, or a pharmaceutically acceptable salt thereof, having a structure:

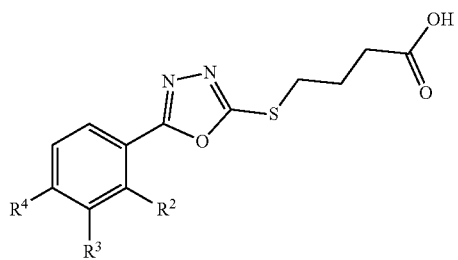

wherein:
$R^2$ is OH or Cl; and
$R^3$ and $R^4$ are each independently selected from the group consisting of H, $C_{1-5}$fluoroalkyl, $OCF(CH_3)_2$, $OCH_2CF_3$, $C_{0-3}$alkylene-$C_{3-5}$cycloalkyl, and $OC_{0-3}$alkylene-$C_{3-5}$cycloalkyl wherein the cycloalkyl is optionally substituted with one or more fluorine atoms, and;
at least one of $R^3$ and $R^4$ is not H.

2. The compound or salt of claim 1, wherein $R^2$ is OH.

3. The compound or salt of claim 1, wherein $R^2$ is Cl.

4. The compound or salt of claim 1, wherein $R^3$:
(a) is H; or
(b) is $CH_2F$, $CHF_2$, $CF_3$, $CF(CH_3)_2$, $CH_2CF_3$, $OCF(CH_3)_2$, or $OCH_2CF_3$; or
(c) comprises cyclopropyl.

5. The compound or salt of claim 1, wherein $R^4$:
(a) is H; or
(b) is $CH_2F$, $CHF_2$, $CF_3$, $CF(CH_3)_2$, $CH_2CF_3$, $OCF(CH_3)_2$, or $OCH_2CF_3$; or
(c) comprises cyclopropyl, optionally wherein $R^4$ is

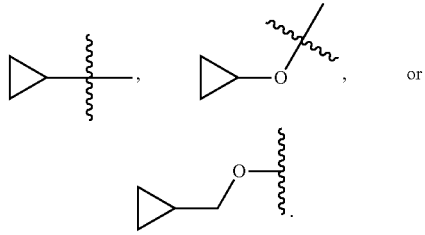

6. The compound or salt of claim 1, wherein:
$R^3$ is selected from the group consisting of H, $CF_3$, $OCH_2CF_3$, and cyclopropyl;
$R^4$ is selected from the group consisting of H, $CHF_2$, $CF_3$, $OCH_2CF_3$, $CF(CH_3)_2$,

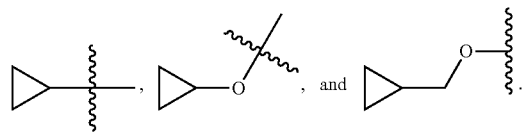

7. A compound, selected from the group consisting of:

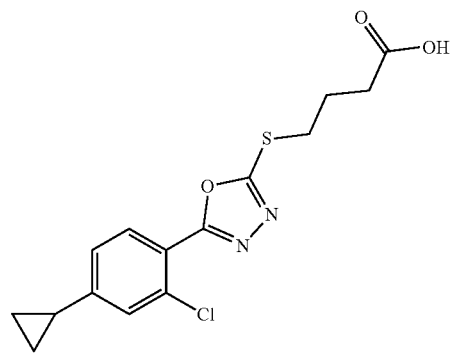 [SMILES: O=C(O)CCCSc1nnc(-c2ccc(C3CC3)cc2Cl)o1]

4-(5-(2-chloro-4-cyclopropylphenyl)-
1,3,4-oxadiazol-2-yl)thio)butanoic acid,

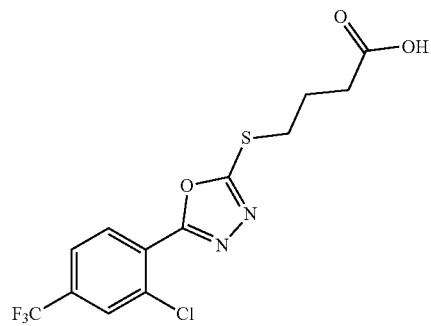 [SMILES: O=C(O)CCCSc1nnc(-c2ccc(C(F)(F)F)cc2Cl)o1]

4-((5-(2-chloro-4-(trifluoromethyl)phenyl)-
1,3,4-oxadiazol-2-yl)thio)butanoic acid, -continued

A3

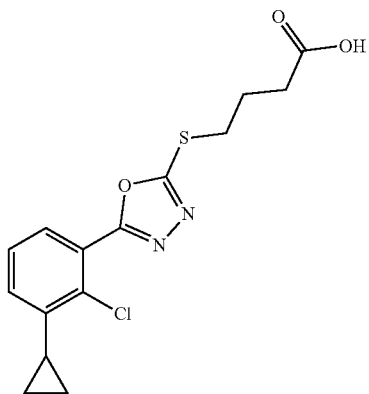 [SMILES: O=C(O)CCCSc1nnc(-c2cccc(C3CC3)c2Cl)o1]

4-((5-(2-chloro-3-cyclopropylphenyl)-
1,3,4-oxadiazol-2-yl)thio)butanoic acid,

A7

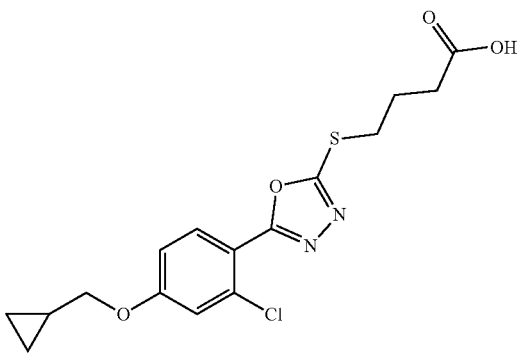 [SMILES: O=C(O)CCCSc1nnc(-c2ccc(OCC3CC3)cc2Cl)o1]

4-((5-(2-chloro-4-
(cyclopropylmethoxy)phenyl)-1,3,4-
oxadiazol-2-yl)thio)butanoic acid,

A8

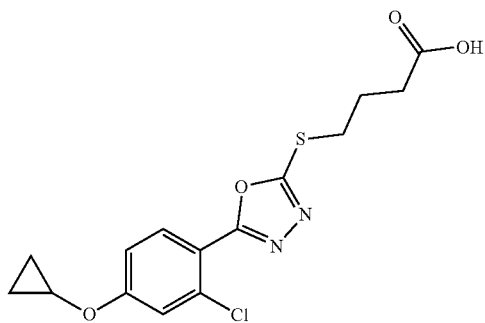 [SMILES: O=C(O)CCCSc1nnc(-c2ccc(OC3CC3)cc2Cl)o1]

4-((5-(2-chloro-4-cycloproboxyphenyl)-
1,3,4-oxadiazol-2-yl)thio)butanoic acid,

A12

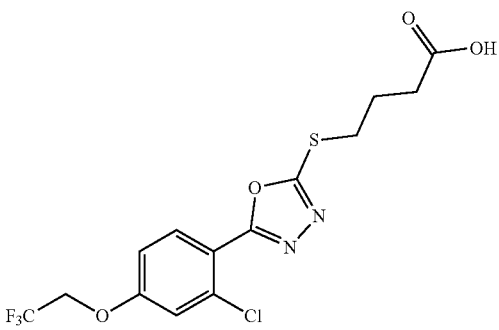 [SMILES: O=C(O)CCCSc1nnc(-c2ccc(OCC(F)(F)F)cc2Cl)o1]

4-((5-(2-chloro-4-(2,2,2-
trifluoroethoxy)phenyl)-1,3,4-oxadiazol-2-
yl)thio)butanoic acid,

A21

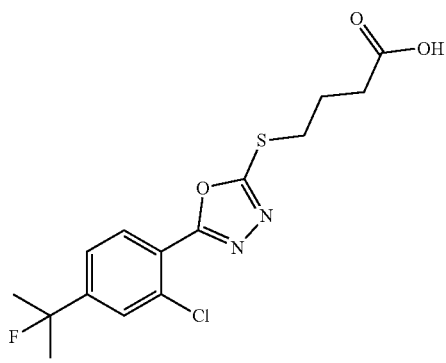 [SMILES: CC(C)(F)c1ccc(-c2nnc(SCCCC(=O)O)o2)c(Cl)c1]

4-((5-(2-chloro-4-(2-fluoroproban-2-
yl)phenyl)-1,3,4-oxadiazol-2-
yl)thio)butanoic acid,

A25

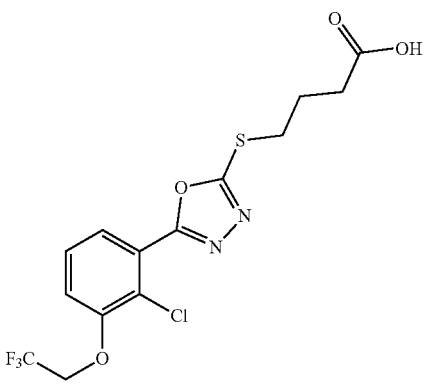 [SMILES: O=C(O)CCCSc1nnc(-c2cccc(OCC(F)(F)F)c2Cl)o1]

4-((5-(2-chloro-3-(2,2,2-
trifluoroethoxy)phenyl)-1,3,4-oxadiazol-2-
yl)thio)butanoic acid,

| A26 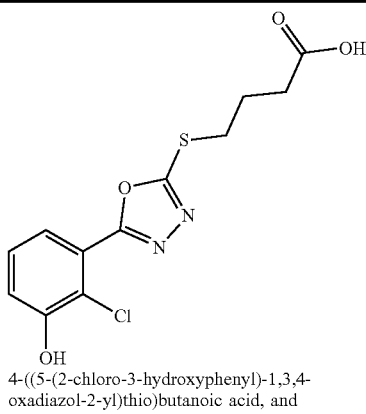 4-((5-(2-chloro-3-hydroxyphenyl)-1,3,4-oxadiazol-2-yl)thio)butanoic acid, and | A27 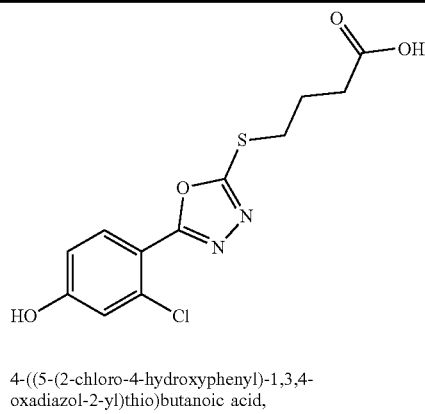 4-((5-(2-chloro-4-hydroxyphenyl)-1,3,4-oxadiazol-2-yl)thio)butanoic acid, |
|---|---| or a pharmaceutically acceptable salt thereof.

8. A compound of Formula (I), or a pharmaceutically acceptable salt thereof:

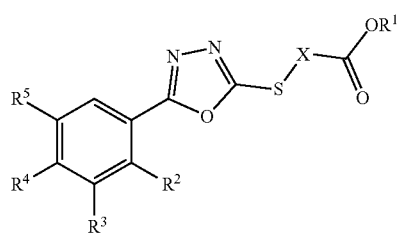

wherein:

X is $C_{3-6}$cycloalkylenyl;

$R^1$ is H or $C_{1-3}$alkyl;

$R^2$ is H, OH, Cl, F, or $CF_3$; and $R^3$, $R^4$, and $R^5$ are each independently selected from the group consisting of H, halo, $C_{1-7}$alkyl, $OC_{1-7}$alkyl, $C_{3-7}$cycloalkyl, $OC_{3-7}$cycloalkyl, $C_{2-4}$heterocycloalkyl, and $OC_{2-4}$heterocycloalkyl, wherein one or two carbon atoms of the alkyl group can optionally be replaced with oxygen, and the heterocycloalkyl group comprises one oxygen ring atom.

9. The compound or salt of claim 8, wherein $R^2$ is not H and two of $R^3$, $R^4$, and $R^5$ are H.

10. The compound or salt of claim 8, wherein the $C_{3-6}$cycloalkylenyl is selected from the group consisting of cyclobutyl, cyclopentyl, and cyclohexyl.

11. The compound or salt of claim 8, wherein $R^3$ is:
(a) H; or
(b) Cl; or
(c) $C_{3-7}$cycloalkyl, $OC_{3-7}$cycloalkyl, $C_{2-4}$heterocycloalkyl, or $OC_{2-4}$heterocycloalkyl, wherein the heterocycloalkyl group comprises one oxygen ring atom, optionally wherein $R^3$ comprises cyclopropyl, cyclobutyl, oxiranyl, or oxetanyl.

12. The compound or salt of claim 8, wherein $R^4$:
(a) is H; or
(b) is Cl; or
(c) is $CHF_2$, $CF_3$, $CH_2CF_3$, or $CF(CH_3)_2$; or
(d) comprises cyclopropyl, cyclobutyl, oxiranyl, or oxetanyl.

13. The compound or salt of claim 8, wherein $R^5$:
(a) is H; or
(b) is $CH_2F$, $CHF_2$, $CF_3$, $CF(CH_3)_2$, $CH_2CF_3$, $OCH_2F$, $OCHF_2$, $OCF_3$, $OCF(CH_3)_2$, or $OCH_2CF_3$; or
(c) comprises cyclopropyl or oxetanyl; optionally wherein $R^5$ is selected from the group consisting of

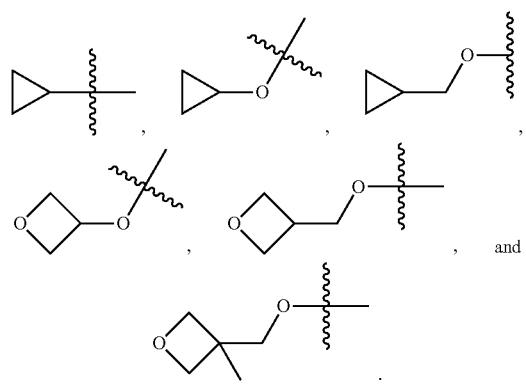

14. The compound or salt of claim 8, wherein:

$R^4$ is selected from the group consisting of Cl, $CF_3$, and cyclopropyl; and $R^5$ is selected from the group consisting of H, $CH_2F$, $CHF_2$, $CF_3$, $CF(CH_3)_2$, $CH_2CF_3$, $OCH_2F$, $OCHF_2$, $OCF_3$, $OCF(CH_3)_2$, $OCH_2CF_3$,

15. A compound selected from the group consisting of:

B1
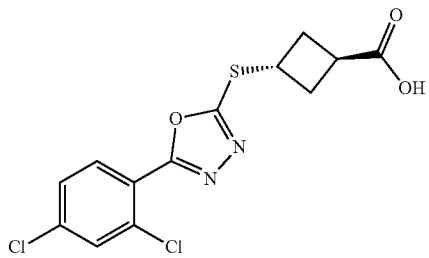 [SMILES: O=C(O)[C@H]1C[C@H](Sc2nnc(-c3ccc(Cl)cc3Cl)o2)C1]
trans-3-((5-(2,4-dichlorophenyl)-1,3,4-oxadiazol-2-yl)thio)cyclobutanecarboxylic acid, B2
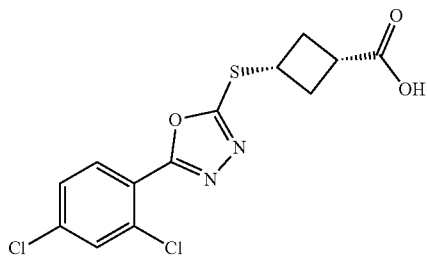 [SMILES: O=C(O)[C@H]1C[C@@H](Sc2nnc(-c3ccc(Cl)cc3Cl)o2)C1]
cis-3-((5-(2,4-dichlorophenyl)-1,3,4-oxadiazol-2-yl)thio)cyclobutanecarboxylic acid, B3
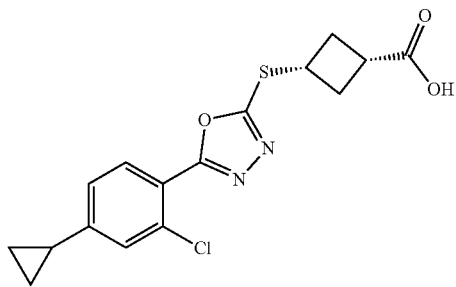 [SMILES: O=C(O)[C@H]1C[C@@H](Sc2nnc(-c3ccc(C4CC4)cc3Cl)o2)C1]
cis-3-((5-(2-chloro-4-cyclopropylphenyl)-1,3,4-oxadiazol-2-yl)thio)cyclobutanecarboxylic acid, B4
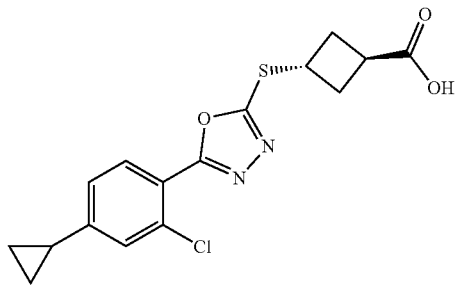 [SMILES: O=C(O)[C@H]1C[C@H](Sc2nnc(-c3ccc(C4CC4)cc3Cl)o2)C1]
trans-3-((5-(2-chloro-4-cyclopropylphenyl)-1,3,4-oxadiazol-2-yl)thio)cyclobutanecarboxylic acid, B5
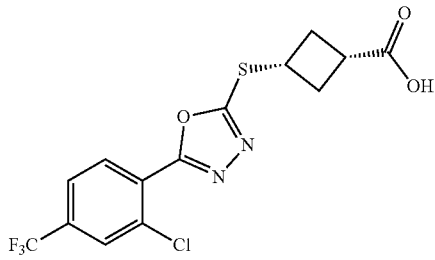 [SMILES: O=C(O)[C@H]1C[C@@H](Sc2nnc(-c3ccc(C(F)(F)F)cc3Cl)o2)C1]
cis-3-((5-(2-chloro-4-(trifluoromethyl)phenyl)-1,3,4-oxadiazol-2-yl)thio)cyclobutanecarboxylic acid, B6
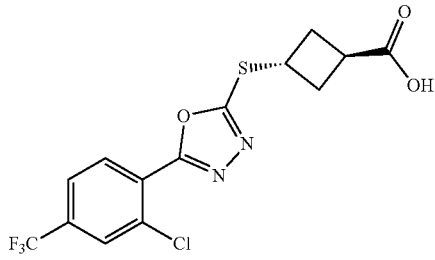 [SMILES: O=C(O)[C@H]1C[C@H](Sc2nnc(-c3ccc(C(F)(F)F)cc3Cl)o2)C1]
trans-3-((5-(2-chloro-4-(trifluoromethyl)phenyl)-1,3,4-oxadiazol-2-yl)thio)cyclobutanecarboxylic acid, B7
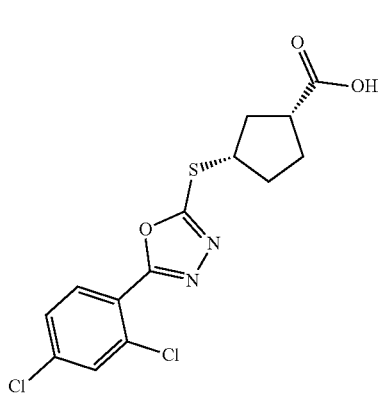 [SMILES: O=C(O)[C@@H]1CC[C@H](Sc2nnc(-c3ccc(Cl)cc3Cl)o2)C1]
cis-3-((5-(2,4-dichlorophenyl)-1,3,4-oxadiazol-2-yl)thio)cyclopentanecarboxylic acid, B8
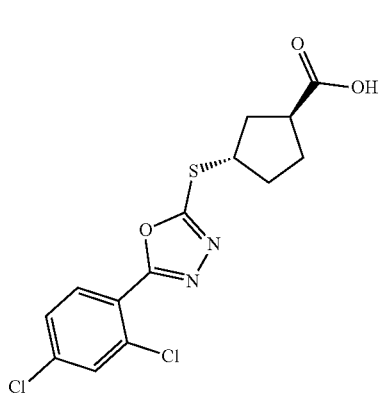 [SMILES: O=C(O)[C@H]1CC[C@H](Sc2nnc(-c3ccc(Cl)cc3Cl)o2)C1]
trans-3-((5-(2,4-dichlorophenyl)-1,3,4-oxadiazol-2-yl)thio)cyclopentanecarboxylic acid,

| B9 | B10 |
|---|---|
| 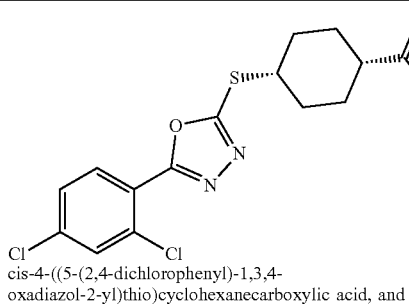 | 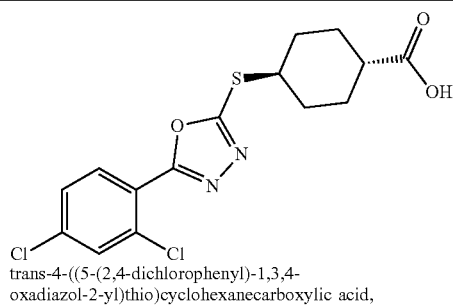 |
| cis-4-((5-(2,4-dichlorophenyl)-1,3,4-oxadiazol-2-yl)thio)cyclohexanecarboxylic acid, and | trans-4-((5-(2,4-dichlorophenyl)-1,3,4-oxadiazol-2-yl)thio)cyclohexanecarboxylic acid, | or a pharmaceutically acceptable salt thereof.

16. A pharmaceutical formulation comprising a compound or salt of claim 1 and a pharmaceutically acceptable excipient.

17. A pharmaceutical formulation comprising a compound or salt of claim 8 and a pharmaceutically acceptable excipient.

* * * * *

UNITED STATES PATENT AND TRADEMARK OFFICE
CERTIFICATE OF CORRECTION

PATENT NO. : 10,851,072 B2
APPLICATION NO. : 16/376349
DATED : December 1, 2020
INVENTOR(S) : Scott D. Larsen et al.

Page 1 of 1

It is certified that error appears in the above-identified patent and that said Letters Patent is hereby corrected as shown below:

In the Claims

At Column 101, Line 49, "4-(5-(2-chloro-4-cyclopropylphenyl)-" should be -- 4-((5-(2-chloro-4-cyclopropylphenyl)- --.

At Column 102, Line 6, "$OC_{0-3}$alkylene-$C_{3-5}$cycloalkyl" should be -- $OC_{0-3}$alkylene-$C_{3-5}$cycloalkyl, --.

At Column 103, Line 7, "4-((5-(2-chloro-4-cycloproboxyphenyl)-" should be -- 4-((5-(2-chloro-4-cyclopropoxyphenyl)- --.

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*